United States Patent [19]
Saaski et al.

[11] Patent Number: 5,697,153
[45] Date of Patent: Dec. 16, 1997

[54] METHOD FOR MANUFACTURING A FLUID FLOW REGULATOR

[75] Inventors: Elric W. Saaski, Bothell; Dale M. Lawrence, Lynnwood, both of Wash.

[73] Assignee: Research International, Inc., Woodinville, Wash.

[21] Appl. No.: 445,008

[22] Filed: May 19, 1995

Related U.S. Application Data

[62] Division of Ser. No. 131,762, Oct. 4, 1993.

[51] Int. Cl.$^6$ ................................................. B23P 15/00
[52] U.S. Cl. ................................. 29/890.128; 29/428
[58] Field of Search ........................... 137/498, 497, 137/500, 501, 503, 517, 859; 29/890.128, 428; 251/368

[56] References Cited

U.S. PATENT DOCUMENTS

| | | | |
|---|---|---|---|
| 942,112 | 12/1909 | Sprecher | 137/503 X |
| 2,192,042 | 2/1940 | Huffman | 137/153 |
| 2,219,408 | 10/1940 | Benz et al. | 137/498 |
| 2,377,227 | 5/1945 | Griswold | 137/503 X |
| 3,109,451 | 11/1963 | Mihalakis | 137/517 X |

(List continued on next page.)

FOREIGN PATENT DOCUMENTS

| | | | |
|---|---|---|---|
| 0112701 | 7/1984 | European Pat. Off. | B41J 3/04 |
| 0 134 614 | 3/1985 | European Pat. Off. | F04B 43/14 |
| 0164089 | 12/1985 | European Pat. Off. | B01D 46/00 |
| 0369997 | 5/1990 | European Pat. Off. | A61M 5/168 |
| 0546427 | 6/1993 | European Pat. Off. | F16K 15/14 |
| 3917423C1 | 5/1990 | Germany | F16K 1/00 |
| 4223067A1 | 1/1994 | Germany | F16K 7/00 |
| 63-164867 | 1/1990 | Japan | A61M 37/00 |
| 04019479 | 1/1993 | Japan | F16K 15/14 |
| 7507369 | 6/1975 | Netherlands | 137/498 |
| 1058453 | 2/1967 | United Kingdom . | |
| 2155152 | 9/1985 | United Kingdom | F16K 7/12 |
| WOA9101464 | 2/1991 | WIPO | F16K 15/14 |
| WOA9214199 | 8/1992 | WIPO | G05D 7/01 |

OTHER PUBLICATIONS

Piezoelectric Micropump With Three Valves Working Peristaltically, Sensors And Actuators, A21-A23, pp. 203-206, Feb., 1990, Jan G. Smits.

Silicon Micropump Replaces Bulky Insulin System, Gail M. Robinson, Design News, vol. 48, No. 20, Oct. 26, 1992, pp. 109-110.

A Piezoelectric Micropump Based On Micromachining Of Silicon, H.T.G. van Lintel et al., Sensors And Actuators, 15, (1988), pp. 153-167.

Fabrication Of A Micropump For Integrated Chemical Analyzing Systems, S. Shoji et al., Electronics And Communications In Japan, Part 2, vol. 72, No. 10 (1989), pp. 52-59.

A Micro Chemical Analyzing System Integrated On A Silicon Wafer, S. Nakagawa et al., 1990, Micromechanical Systems Conference, IEEE Publication No. CH2832-4/90/0000-0089.

(List continued on next page.)

*Primary Examiner*—Irene Cuda
*Attorney, Agent, or Firm*—Gregory W. Moravan

[57] ABSTRACT

The fluid handling devices are capable of accurately handling substantially continuous fluid flow rates as low as about 0.01 cc/day. The devices are so miniaturized, corrosion-resistant and non-toxic that they are suitable for being implanted in the human body; and are capable of being mass produced at costs so low, by using micromachining techniques, such as etching, that they may be considered to be disposable. The devices are either passive devices which consume no electrical energy at all, or are active devices which consume very small amounts of electrical energy. The devices are reliable because they may have as few as only two parts, only one which is a moving part; and because they may handle fluids at very low pressures. The fluid handling devices include active piezoelectrically driven membrane pumps; and passive fluid flow regulators, on-off valves, flow switches and filters.

8 Claims, 20 Drawing Sheets

U.S. PATENT DOCUMENTS

| | | |
|---|---|---|
| 3,520,641 | 7/1970 | Casey . |
| 3,718,152 | 2/1973 | Kraakman ................................ 137/517 |
| 3,773,073 | 11/1973 | Brown ..................................... 137/501 |
| 3,812,876 | 5/1974 | Kreiter .................................... 137/501 |
| 3,886,968 | 6/1975 | Murrell .................................... 137/501 |
| 3,963,380 | 6/1976 | Thomas, Jr. . |
| 3,973,410 | 8/1976 | Putman et al. ...................... 137/517 X |
| 4,016,231 | 4/1977 | Hawkins . |
| 4,022,244 | 5/1977 | Oman ..................................... 137/517 |
| 4,142,523 | 3/1979 | Stegeman . |
| 4,152,098 | 5/1979 | Moody et al. . |
| 4,159,954 | 7/1979 | Gangemi . |
| 4,250,915 | 2/1981 | Rikuta ..................................... 137/501 |
| 4,269,391 | 5/1981 | Saito et al. ......................... 251/315 SE |
| 4,299,220 | 11/1981 | Dorman . |
| 4,343,305 | 8/1982 | Bron . |
| 4,344,743 | 8/1982 | Bessman et al. . |
| 4,411,603 | 10/1983 | Kell . |
| 4,414,172 | 11/1983 | Leason . |
| 4,420,142 | 12/1983 | Dworak et al. ................. 137/625.14 X |
| 4,450,375 | 5/1984 | Seigal . |
| 4,678,904 | 7/1987 | Saaski et al. . |
| 4,692,147 | 9/1987 | Duggan . |
| 4,705,058 | 11/1987 | Marklew . |
| 4,712,583 | 12/1987 | Pelmulder et al. . |
| 4,715,852 | 12/1987 | Reinicke et al. . |
| 4,756,508 | 7/1988 | Giachino et al. . |
| 4,768,751 | 9/1988 | Giachino et al. . |
| 4,778,987 | 10/1988 | Saaski et al. . |
| 4,869,282 | 9/1989 | Sittler et al. . |
| 4,903,732 | 2/1990 | Allen . |
| 4,943,032 | 7/1990 | Zdeblick . |
| 4,963,260 | 10/1990 | Naoi et al. . |
| 4,990,256 | 2/1991 | Schmidt . |
| 5,019,047 | 5/1991 | Kriesel . |
| 5,085,562 | 2/1992 | van Lintel . |
| 5,142,781 | 9/1992 | Mettner et al. . |
| 5,219,278 | 6/1993 | van Lintel . |
| 5,224,843 | 7/1993 | van Lintel . |
| 5,246,031 | 9/1993 | Eichler et al. ........................... 137/859 |
| 5,269,917 | 12/1993 | Stankowski . |
| 5,304,487 | 4/1994 | Wilding et al. . |
| 5,368,060 | 11/1994 | Worral et al. . |
| 5,407,613 | 4/1995 | Schulte . |
| 5,441,597 | 8/1995 | Bonne et al. . |

OTHER PUBLICATIONS

Applications Of Silicon Microactuators Based On Bimorph Structures, W. Beneke et al., 1989, Micro Electromechanical Systems Conference, pp. 116–120.

Electrically–Activated, Micromachined Diaphragm Valves, Proceedings For IEEE Conference On Solid State Sensors And Actuators, Jun. 4–7, 1990, H. Jerman, pp. 65–69, IEEE Publication No. CH2783–9/90/0000–0065.

A Pressure–BalancedElectrostatically–Actuated Microvalve, M. Huff, et al., Jun., 1990, Solid State Sensors And Actuators Conference, pp. 123–127, IEEE Publication No. CH2783–9/90/0000–0123.

Micromachined Silicon Microvalve, Feb. 11–14, 1990, T. Ohnstein et al., Proceedings For IEEE Conference On Micro Electro Mechanical Systems, pp. 95–98, IEEE Publication No. CH2832–4/90/0000–0095.

A Constant Flow–Rate Microvalve Actuator Based On Silicon And Micromachining Technology, S. Park et al, Proceedings For 1988 Solid State Sensor And Actuator Workshop, Jun. 6–9, 1988, pp. 136–139, IEEE Publication No. TH0215–4/88/0000–0136.

METHOD FOR MANUFACTURING A FLUID FLOW REGULATOR

This application is a division of prior application Ser. No. 08/131,762, filed on Oct. 4, 1993, pending.

BACKGROUND OF THE INVENTION

The present invention relates to fluid handling devices. More particularly, it relates to reliable, accurate, fluid handling devices which are capable of handling fluid flow rates which are so low that they may be measured in hundredths of a cubic centimeter per day; which may have either a zero or an extremely small electrical energy consumption; and which may be economically mass produced by using micromachining processes.

SUMMARY OF THE INVENTION

In many medical situations, it is desirable to continually administer fluid medication to a patient over an extended period of time at a relatively low flow rate. Examples of such cases are the use of morphine for the treatment of malignant or non-malignant pain; the use of FUDR for cancer chemotherapy; and the use of baclofen for the treatment of intractable spasticity.

This manner of administering the medication is desirable because the level of the fluid medication in the patient's blood remains at a relatively constant, medically effective level. By way of contrast, if the medication was administered periodically in larger doses, such as in tablet form by mouth, the level of the medication in the patient's blood may tend to fluctuate markedly over time, from too little to too much, rather than staying at the desired medically effective level.

Accordingly, one general aspect of the present invention may be to provide fluid handling devices which are capable of continually handling fluids over an extended period of time at relatively low flow rates, which may be as low as about 0.01 cc/day.

In many medical situations it is desirable to have fluid handling devices which are extremely small, so that they may be implanted within a patient's body. Accordingly, another general aspect of the present invention may be to provide fluid handling devices which are so small that they may be easily implanted within a patient's body.

However, when making a fluid handling device which is so small, it becomes relatively easy to inadvertently clog any openings in the device (such as its ports, channels, cavities, or gaps) if a bonding material is used to bond the various parts of the fluid handling device together. Accordingly, another general aspect of the present invention is to provide fluid handling devices in which at least some of their parts are anodically bonded together, thereby eliminating the need to use a separate bonding material to bond those parts together.

If the fluid handling devices are intended to be implanted in a patient's body, it is preferable that they either be passive devices, which do not consume any electrical energy at all; or, if they are active devices, that they consume as little electrical energy as possible for the quantity of fluid which they are to handle. This is important for at least two reasons. First, the less electrical energy the fluid handling devices consume, the smaller the batteries within the implanted device may be, thereby enabling the implanted device to be made smaller than might otherwise be the case. Second, the less electrical energy the fluid handling devices consume, the longer any particular size of battery will last; thereby avoiding frequent surgical replacement of the implanted device, or its batteries. Accordingly, another general aspect of the present invention may be to provide fluid handling devices which, if they are passive devices, consume no electrical energy at all; or, if they are active devices, consume as little electrical energy as possible for the quantity of fluid which they are to handle.

In medical situations, the reliability of the devices which handle the fluid medication must be very high. In general, reliability may be enhanced by simplifying the fluid handling devices to have as few total parts as possible; to have as few moving parts as possible; and to have nominal operating pressures which are as low as possible. Accordingly, one general aspect of the present invention may be to provide fluid handling devices which are inherently highly reliable because they may have a total of as few as two parts, as few as one of which may be a moving part. Another general aspect of the present invention may be to provide fluid handling devices which may operate at pressures as low as about 25 millimeters of mercury.

In medical situations, it is desirable to have fluid handling devices which have a fail-safe design so that if they are subjected to overpressures in excess of their nominal design limits, they are very resistant to failure, so that they do not deliver excessive amounts of the medication to the patient. Accordingly, another general aspect of the present invention may be to provide fluid handling devices which, when subjected to an overpressure, may be resistant to being ruptured because their flexures or membranes may be at least partially supported by at least one other element of the fluid handling devices; and which may reduce the flow of the medication, or shut it off altogether.

In view of the generally high cost of medical care, it is desirable to provide high quality, accurate, reliable fluid handling devices at a price which is so economical that the fluid handling devices may be considered to be disposable. Accordingly, another general aspect of the present invention may be to achieve these goals by using micromachining processes to mass produce the fluid handling devices, or parts thereof.

Since many medications and body fluids are corrosive, particularly where the fluid handling device is used for an extended period of time, or is implanted in a human or an animal, it is important that the fluid handling device be corrosion-resistant. Accordingly, three further general aspects of the present invention may be to provide the fluid handling device having a layer of one or more corrosion-resistant substances; to bond such a corrosion-resistant layer to the fluid handling device by using anodic bonding; and to automatically perform such anodic bonding of the corrosion-resistant layer at the time certain other parts of the fluid handling device are being anodically bonded together.

In many medical situations, it may be desirable to maintain the flow rate of the liquid medication to a patient at a predetermined rate, despite any fluctuations (either increases or decreases) in the pressure of the supply of the medication. For example, if the supply of the medication comprises a reservoir in which the medication is pressurized with a gas, as the reservoir is emptied the gas expands, thereby reducing the pressure on the decreasing amount of medication remaining in the reservoir. Accordingly, in addition to one or more of the above general aspects of the present invention, a specific aspect of the present invention may be to provide a fluid handling device in the form of a flow regulator which will maintain the flow of the medication within predetermined parameters, despite fluctuations in the pressure of the medication which is received by the flow regulator, or fluctuations in the pressure at the medication outlet port.

Such a flow regulator may comprise a substrate having fluid inlet means, a regulator seat, and fluid outlet means. The flow regulating device may further comprise a flexure bonded to the substrate, and a regulator gap which is located between the flexure and the regulator seat.

During use, both the fluid inlet means and the outer surface of the flexure may be exposed to a source of liquid medication under pressure. The medication will flow sequentially through the fluid inlet means, the regulator gap and the fluid outlet means. As the medication flows through the regulator gap, the height of the regulator gap will tend to decrease as the driving pressure difference across the regulator increases, and will tend to increase as the driving pressure difference across the regulator decreases. As a result, the regulator will tend to hold the flow rate of the medication constant, despite any fluctuations in the driving pressure difference of the medication across the flow regulator.

Another specific aspect of the flow regulator of the present invention may be that its flow rate may be selectively increased or decreased by selectively increasing or decreasing the number, size, shape and length of its fluid inlet means.

A further specific aspect of the flow regulator of the present invention may be that its characteristic flow rate verses its applied driving pressure difference response may be chosen by selectively adjusting the fluid flow resistances of the fluid inlet means and the regulator gap with respect to each other.

Other specific aspects of the flow regulator of the present invention may be that it may be a radial flow regulator, in which at least a portion of its fluid inlet means extend at least substantially around its regulator seat's periphery; in which its flexure overlies its regulator seat and extends outwardly past its regulator seat's periphery; in which at least part of its fluid outlet means are located within its regulator seat; and in which the medication flows from its fluid inlet means radially inwardly across its regulator seat's top surface, from its regulator's periphery to its fluid outlet means.

Further specific aspects of the flow regulator of the present invention may be that it may be a linear flow regulator which may have an elongated regulator seat and an elongated flexure which extend between the inlet means and the outlet means.

Other specific aspects of the linear flow regulator of the present invention may be that it may have a length to width ratio (L/W) in the range of from about 5:1 to about 1000:1, and preferably about 20:1; that its flexure be unrestrained at its inlet means; and that its regulator seat and flexure may follow a straight course, a non-straight course (such as circular, spiral, or sinuous), or a combination thereof.

Two further specific aspects of the linear flow regulator of the present invention may be that its regulator seat may have a contoured shape, such as the shape its flexure would assume if its flexure was unsupported by its substrate, and was subjected to a certain driving pressure difference across the regulator; and that such a contoured shape may be imparted to its regulator seat by pressure deflecting the flexure down into the substrate while the substrate is in a softened state, maintaining such pressure while the substrate is hardened, and then releasing such pressure and permitting the flexure to return to its original, undeflected configuration.

Other aspects of the linear flow regulator of the present invention may be that its regulator seat may comprise a channel in its substrate; that its channel may not have a contoured shape; and that its channel may be micromachined into its substrate by being etched into its substrate.

As was mentioned above, in many medical situations, it is desirable to be able to administer a flow of fluid medication to a patient in an at least substantially continuous manner over an extended period of time at a relatively low flow rate, in order to maintain a relatively constant, medically effective level of the medication in the patient's blood.

Accordingly, in addition to one or more of the above general aspects of the present invention, one specific aspect of the present invention may be to provide a pump which is capable of producing such a flow of fluid medication; wherein the pump may have a displacement per pumping cycle from about 0.05 microliters to about 10 microliters of medication (and preferably about 1.0 microliters of medication); wherein the total flow rate of the pumping medication may be from about 0.01 cc/day to about 20.00 cc/day (and preferably about 0.1 cc/day to 2.0 cc/day); and wherein the pumping cycle frequency may be as high as about 25 cycles per second.

Another specific aspect of the pump of the present invention may be to provide a pump which, for any given quantity of the pumped liquid medication, utilizes as little electrical energy as possible, at driving voltages which are as low as possible. This goal may be achieved by providing a pump having a pumping flexure which may be driven by a piezoelectric motor; wherein there may be an elastomeric joint between the piezoelectric motor and the pumping flexure which reduces shear loads between the piezoelectric motor and the pumping flexure, thereby dramatically increasing the energy efficiency of the pump by as much as five times, and permitting driving voltages as low as about 50.0 volts to be used. This goal may also be achieved by providing a pump having a relatively low operating pressure, in the range of from about 1.0 mm Hg to about 200 mm Hg, for example.

A further specific aspect of the pump of the present invention may be to have its piezoelectric motor serve the dual functions of driving the pumping flexure, and protecting the pumping flexure from damage. This goal may be achieved by selecting the piezoelectric motor to have a diameter larger than that of the pumping flexure; by bonding the piezoelectric motor to the pumping flexure's outer surface; and by sizing the pump's substrate and the piezoelectric motor so that the periphery of the piezoelectric motor is supported by the substrate. In this way, the piezoelectric motor may shield, and thus help prevent the pumping flexure from being damaged.

A still further specific aspect of the pump of the present invention may be to protect its pumping flexure from damage which might otherwise be caused if the pumping flexure were driven into the pump's pumping cavity greater than a predetermined amount. This goal may be achieved by providing the pumping cavity with pumping flexure supports, which may support the pumping flexure, and which prevent the pumping flexure from being driven into the pump's pumping cavity greater than a predetermined amount.

Another specific aspect of the pump of the present invention may be that its internal features may be designed and arranged so that the possibility of trapping bubbles within the pump are minimized; and so that during operation of the pump, any bubbles within the pump may tend to be swept out of the pump by the flow of the medication through it.

Such bubbles within the pump may be undesirable, since they may interfere with the proper operation of the pump's valves, and since they may result the patient having a dangerous air embolism.

Further specific aspects of the pump of the present invention may be that it minimizes, or even eliminates, any reverse flow of the medication through the pump, in the event the pump is subjected to a negative pressure difference; and any high forward flow of the medication through the pump, in the event the medication which is supplied to the pump is overpressurized, and exceeds a predetermined nominal value. This goal may be achieved by arranging the pump so that when no voltage is supplied to the pump's piezoelectric motor, the weight and stiffness of the pumping flexure and the piezoelectric motor may tend to hold the pump's inlet valve closed. This goal may be further achieved by arranging the pump so that when a reversed polarity voltage is applied to the piezoelectric motor, the pumping flexure may be driven against the inlet valve, to thereby hold the inlet valve closed. Thus, in the present invention the piezoelectric motor and the pumping flexure may serve the dual functions of: (a) pumping the medication, and (b) minimizing, or even eliminating, reverse flows of the medication through the pump, and high forward flows of the medication through the pump in the event of an overpressurization situation.

Another specific aspect of the pump of the present invention may be that it may have a minimal amount of complexity and cost. This goal may be achieved by avoiding the deep etching of features into both faces of the pump's substrate; and by using, instead, the shallow etching of features into only one face of the pump's substrate. This goal may also be achieved by the pump using passive inlet and outlet valves.

A further specific aspect of the pump of the present invention may be that a residual amount of the medication is maintained in the pump's pumping cavity at all times during the pump's complete pumping cycle. This may permit the pump to be operated at a higher pumping cycle frequency, and may also increase the energy efficiency of the pump, since the residual medication in the pumping cavity may provide a low resistance path for the new medication which enters the pumping cavity during each pumping cycle.

Other specific aspects of the pump of the present invention may be that it may have integral inlet and outlet valves, whose valve seats are formed in the pump's substrate; wherein the inlet valve is wholly contained within the pump's pumping cavity; and wherein the outlet valve seat is wholly contained with the pump's outlet valve cavity. In addition, the pump may comprise as few as four basic components (namely a substrate, a one-way inlet valve, a membrane and a piezoelectric motor); and wherein the membrane may serve the quadruple functions of being the pump's pumping flexure, the outlet valve's flexure, the seal for the pump's pumping cavity, and the seal for the pump's outlet valve cavity.

Further specific aspects of the pump of the present invention may be that the pump's inlet valve may be located adjacent to an edge of the pump's pumping cavity; and wherein the pump's outlet valve may be located either in the center of the pumping cavity, or as far from the inlet valve as possible. This may enable the pump to automatically prime itself very reproducibly during operation, due to the surface tension between the medication and the pumping cavity's edge; and may enable the pump to avoid forming or trapping bubbles within the pumping cavity, by enabling the medication to sweep any bubbles out of the pumping cavity as the medication travels across the pumping cavity from the inlet valve to the outlet valve.

Other specific aspects of the pump of the present invention may be that the pump may be a modular pump. That is, the pump may comprise a pumping portion module, an inlet valve module, and an outlet valve module; wherein the completed pump may be made by assembling these three modular components together.

A further aspect of the modular pump of the present invention may be that it may be arranged to have an outlet valve seat located within its pumping cavity. This arrangement may have several advantages. First, when no voltage is supplied to the pump, the weight and stiffness of the pumping flexure and the piezoelectric motor may tend to hold the pumping flexure against the outlet valve seat; thereby minimizing, or even eliminating, high forward flows of the medication through the pump in the event of an overpressurization situation. Second, when a reversed polarity voltage is applied to the piezoelectric motor, the pumping flexure may be driven against the inlet valve, to thereby hold the inlet valve closed. Thus, here again, in the present invention the piezoelectric motor and the pumping flexure may serve the dual purposes of: (a) pumping the medication, and (b) minimizing, or even eliminating, high forward flows of the medication through the pump in the event of an overpressurization situation. Third, if the upper faces of the piezoelectric motor/pumping flexure combination is exposed to the medication at the pump's inlet pressure, then the pump may functionally behave as if it were a radial flow regulator; and may thereby reduce, or even stop, the flow of the medication through the pump in the event of an overpressurization situation.

Another specific aspect of the present invention may be that the maximum flow rate of the medication through the pump may be regulated by adjusting the size of the pump's inlet port, outlet port, and the height of the gap between the pump's substrate and the modular inlet valve's flexure.

In addition to one or more of the above general aspects of the present invention, one specific aspect of the present invention may be to provide a micromachined one-way valve which will permit the medication to flow through it in only one direction, with very low fluid flow resistance in the forward direction, and with very high fluid flow resistance in the reverse direction. The one-way valve may comprise a substrate defining an inlet port, and an inlet valve seat. A membrane may be secured to the substrate and comprise at least one outlet port, and a flexure which extends over the inlet valve seat. During operation, as medication under a positive pressure is applied to the substrate's inlet port, the medication flows in through the inlet port, lifts and unseats the membrane from the inlet valve seat, flows between the flexure and the inlet valve seat, and exits the one-way valve through the membrane's outlet port.

Another specific aspect of the one-way valve of the present invention may be that the inlet and outlet ports of the one-way valve may be located on opposite sides of the one-way valve, to enable the one-way valve to be used as both an inlet one-way valve, and as an outlet one-way valve, simply by turning the one-way valve over.

Other further specific aspects of the one-way valve of the present invention may be that the flexure may be elongated; that the flexure may have at least a portion of both of its ends anchored to the substrate; that the flexure's bottom surface and the inlet valve seat's top surface may be coplanar; and that the inlet valve seat may have any suitable shape, such as ring-shaped or rectangular.

A further specific aspect of the one-way valve of the present invention may be that the elongated flexure having anchored ends may not need to have a rigid center boss for sealing between the flexure and the valve's inlet valve seat. Such a flexure offers the advantage that it has a flexibility which is increased considerably as compared to the flexibility of a flexure which does have such a rigid center boss. It has also been discovered that such increased flexibility of the flexure may be translated into either a smaller one-way valve, or a one-way valve which has a lower forward pressure drop.

Another specific aspect of the one-way valve of the present invention may be that the elongated flexure having anchored ends may be prestressed (i.e., stretched), across the inlet valve seat, so that at a zero driving pressure difference across the one-way valve, the flexure is under a tension which may tend to hold it against the inlet valve seat, and prevent any flow of the medication across the inlet valve seat. Such prestressing of the flexure may offer numerous advantages. Among such advantages are that the one-way valve may have a great resistance to permitting any medication to "bleed" from its outlet when the one-way valve is subjected to a supposedly zero driving pressure difference (P) across the one-way valve; that the one-way valve may have a great resistance to permitting any medication to flow through it when the one-way valve is subjected to a negative driving pressure difference (P); that the one-way valve may offer a smoother change in its flow rate (Q) as a function of the driving pressure difference (P) across the one-way valve; that there may be a greater uniformity in the performance of the one-way valve when it is mass produced; that the forward opening characteristics of the one-way valve may be tuned; and that the edges of the flexure may have less tendency to curl, which curling might otherwise interfere with the proper operation of the one-way valve.

A further specific aspect of the one-way valve of the present invention may be that the elongated flexure having anchored ends may be prestressed by choosing the substrate and the flexure to be manufactured from materials having different coefficients of thermal expansion; securing the substrate and the flexure together at a temperature which is substantially different from the one-way valve's designed operating temperature range; and then returning the one-way valve to its designed operating temperature range, so that the flexure is automatically prestressed due to the difference in the coefficients of thermal expansion of the substrate and the flexure. In addition, the elevated bonding temperature may also help to conform the mating surfaces of the inlet valve seat and the flexure with each other, to help prevent back flow leakage of the medication therebetween.

Other specific aspects of the one-way valve of the present invention may be that the substrate may have etched into one of its faces a ring-shaped inlet cavity having a central, projecting inlet valve seat; wherein the inlet valve seat's top surface may be higher than the top surface of the rest of the substrate; wherein the flexure may be circular, may have its periphery secured to the substrate, and may have a centrally located outlet port located over the inlet valve seat; wherein the outlet port may be smaller than the inlet valve seat; and wherein the flexure may be prestressed, due to the height difference between the top surfaces of the inlet valve seat and the rest of the substrate, which may tension the flexure by causing an interference fit between the inlet valve seat and the flexure. A one-way valve having such a prestressed circular flexure offers most, if not all, of the advantages set forth above regarding the one-way valve having an elongated flexure with anchored ends.

Another specific aspect of the one-way valve of the present invention having a circular flexure may be that the membrane and the flexure may be secured to the substrate despite the interference fit between the inlet valve seat and the flexure by forming the membrane and flexure from a wafer of material; by choosing the wafer to comprise a material which may be relatively stiff at an elevated anodic bonding temperature; by choosing the substrate to comprise a material which may be relatively elastic at the elevated anodic bonding temperature; by using anodic bonding at the elevated anodic bonding temperature to bond the wafer to the substrate, wherein the relatively stiff wafer may compress the relatively elastic inlet valve seat and permit the wafer to be anodically bonded to the substrate; and by then reducing the wafer to the final thickness of the membrane and the flexure, thereby automatically freeing the inlet valve seat from its compressed configuration and permitting it to return to its original, uncompressed configuration. The elevated bonding temperature may also help to conform the mating surfaces of the inlet valve seat and the flexure with each other, to help prevent back flow leakage therebetween.

A further specific aspect of the one-way valve of the present invention may be that it may not need to have a separate stop for limiting the predetermined maximum travel of the flexure away from the inlet valve seat. Such a predetermined maximum travel of the flexure would, in turn, limit the predetermined maximum flow rate (Q) of the medication through the one-way valve, for the predetermined maximum driving pressure difference (P) across the one-way valve. This may be accomplished in at least three ways. First, the flexure may be elongated, and may have both of its ends secured to the substrate, so that, at a predetermined maximum driving pressure difference (P) across the one-way valve, the flexure may have a predetermined maximum deflection as it bows away from the inlet valve seat. Second, the flexure may be circular, the outlet port may be located in the flexure, and the flexure may have its outer periphery secured to the substrate, so that at a predetermined maximum driving pressure difference (P) across the one-way valve, the flexure may have a predetermined maximum deflection as it balloons away from the inlet valve seat. Third, the predetermined maximum deflection of the flexure may be limited by a stop portion of whatever object to which the one-way valve may be secured.

Another specific aspect of the one-way valve of the present invention may be that when it is mounted in its intended location of use on an object, the flexure may be located in close proximity to a surface on the object, and at least a portion of the medication which exits said one-way valve may pass through a gap between said flexure and said surface on said object. As a result, said flexure, said gap, and said surface on said object may form a fluid flow regulator, to regulate the flow rate (Q) of the medication from said one-way valve, and to hold it within, or below, a predetermined range of values. That is, if the driving pressure difference (P) decreases, then the flexure will tend to be deflected towards said surface on said object a decreased amount, thereby increasing the height of the gap. This, in turn, tends to maintain the flow rate (Q) at a relatively constant value, despite the reduced driving pressure difference (P). This is because the increased height of the gap will tend to compensate for the reduced driving pressure difference (P) by increasing the flow rate (Q) which would otherwise occur at that reduced driving pressure difference (P). On the other hand, if the driving pressure difference (P)

across the flexure increases, then the flexure will tend to be deflected towards said surface on said object an increased amount, thereby reducing the height of the gap. This, in turn, tends to maintain the flow rate (Q) at a relatively constant value, despite the increased driving pressure difference (P). This is because the reduced height of the gap will tend to compensate for the increased driving pressure difference (P) by reducing the flow rate (Q) which would otherwise occur at that increased driving pressure difference (P). Lastly, at still higher driving pressure differences (P) the flow rate (Q) is gradually reduced to zero, as the flexure is driven closer and closer to said surface on said object.

In many medical situations, it may be desirable to automatically switch off the flow of the medication to a patient if the medication exceeds a predetermined pressure or flow rate, in order to prevent the patient from receiving an overdose of the medication; and to automatically switch the flow of the medication back on, once the pressure of the medication falls below that predetermined pressure.

Accordingly, in addition to one or more of the above general aspects of the present invention, a specific aspect of the present invention may be to provide a fluid handling device in the form of a flow switch which will automatically switch off the flow of the medication through the flow switch in the event the medication exceeds a predetermined pressure or flow rate, and which will automatically switch the flow of the medication through the flow switch back on once the pressure of the medication falls below that predetermined pressure.

Such a flow switch may comprise a substrate having a inlet switch seat, and outlet means. The flow switch may further comprise a membrane secured to the substrate, wherein the membrane's mounting portion is secured to the substrate, the membrane's flexure extends partially over the inlet switch seat, and the flexure's inlet port is located over the inlet switch seat. A switch gap is located between the flexure and the switch seat.

During use, the flexure's top surface and the inlet port are exposed to a source of the medication under pressure. The medication will flow sequentially through the inlet port, radially outwardly across the switch seat's top surface in the switch gap, and out through the outlet. As the driving pressure difference (P) of the medication across the flow switch is increased from zero, the medication gradually forces the flexure closer to the switch seat, thereby gradually decreasing the height of the switch gap (and vice versa).

Then, at a predetermined overpressure of the medication, i.e., at a predetermined driving pressure difference switch point ($P_{SW}$), the flexure automatically begins an irreversible collapse that results in the flexure being forced by the medication against the inlet switch seat, and being held there by the medication, thereby automatically closing the switch gap, switching off the flow switch, and stopping the flow of the medication through the flow switch.

Then, when the driving pressure difference (P) across the flow switch is decreased to less than the predetermined overpressure, i.e., is decreased to less than the driving pressure difference switch point ($P_{SW}$), the resiliency and elasticity of the flexure cause it to automatically move away from the inlet switch seat, thereby automatically opening the switch gap, switching the flow switch back on, and permitting the medication to flow through the flow switch once again.

In many medical applications the fluid flow rates of the medication may be very low, such as from about 0.01 cc per day to about 10.00 cc per day. As a result, the fluid passages in the fluid handling devices which are capable of dealing with such very low flow rates have dimensions which may be as small as one or two microns, or less. Thus, the potential exists for such very small fluid passages to be clogged by even very small particles in the medication.

Accordingly, in addition to one or more of the above general aspects of the present invention, a specific aspect of the present invention may be to provide a fluid handling device in the form of a filter which will filter out from the medication particles which may have a size as small as about 0.02 micron, or less.

A further specific aspect of the filter of the present invention may be to provide a filter comprising as few as two basic components, namely a substrate and a membrane.

Another specific aspect of the filter of the present invention may be that the filter may share its substrate and membrane with at least one other fluid handling device, wherein such other fluid handling device also comprises the same substrate and membrane, and may receive filtered medication from the filter through fluid passages defined between the same substrate and membrane.

Further specific aspects of the filter of the present invention may be to provide a radial array filter having a ring-shaped radial array of filter slots which are manufactured in the substrate; wherein the membrane serves as the cover for the filter slots; and wherein another fluid handling device, which is to receive the filtered medication from the radial array filter, is located concentrically within the ring-shaped radial array of filter slots.

Another specific aspect of the radial array filter of the present invention may be that it further comprises a ring-shaped inlet cavity, for distributing the incoming medication substantially equally to all of the filter slots; and a ring-shaped outlet cavity, for collecting the filtered medication from the filter slots substantially equally. The inlet and outlet cavities may also serve to provide a relatively uniform pressure drop across all of the filter slots.

A further specific aspect of the present invention may be to provide a slab filter comprising a filter element suspended over an outlet cavity in the substrate; and an inlet port in the membrane for permitting the medication to reach the filter element.

Other specific aspects of the present invention may be to provide a slab filter in which the edges of the filter element may sandwiched between the substrate and the membrane; and which may have a filter element entrance through which the filter element may be inserted into place over the slab filter's outlet cavity.

Although all of the forgoing comments regarding the fluid handling devices of the present invention have been with reference to handling medicinal fluids in a medical context, it is understood that the fluid handling devices of the present invention may also be used to handle any type of non-medicinal fluid, in both medical and non-medical contexts. In addition, although the fluid handling devices which were mentioned above may be very small and may handle fluids at very low flow rates and at relatively low pressures, it is understood that, by applying scaling laws, the fluid handling devices of the present invention may, in general, be scaled up to any desired size; to handle any desired fluid flow rate and pressure. Further, the term "fluid" is used in its broad sense, and includes both liquids and gasses.

It should be understood that the foregoing summary of the present invention does not set forth all of its features, advantages, characteristics, structures, methods and/or processes; since these and further features, advantages, characteristics, structures, methods and/or processes of the present invention will be directly or inherently disclosed to those skilled in the art to which it pertains by the following, more detailed description of the present invention.

DESCRIPTION OF THE PREFERRED EMBODIMENTS

MICROMACHINED RADIAL FLOW REGULATOR 32 (FIGS. 1–6): STRUCTURE

Figure 1:
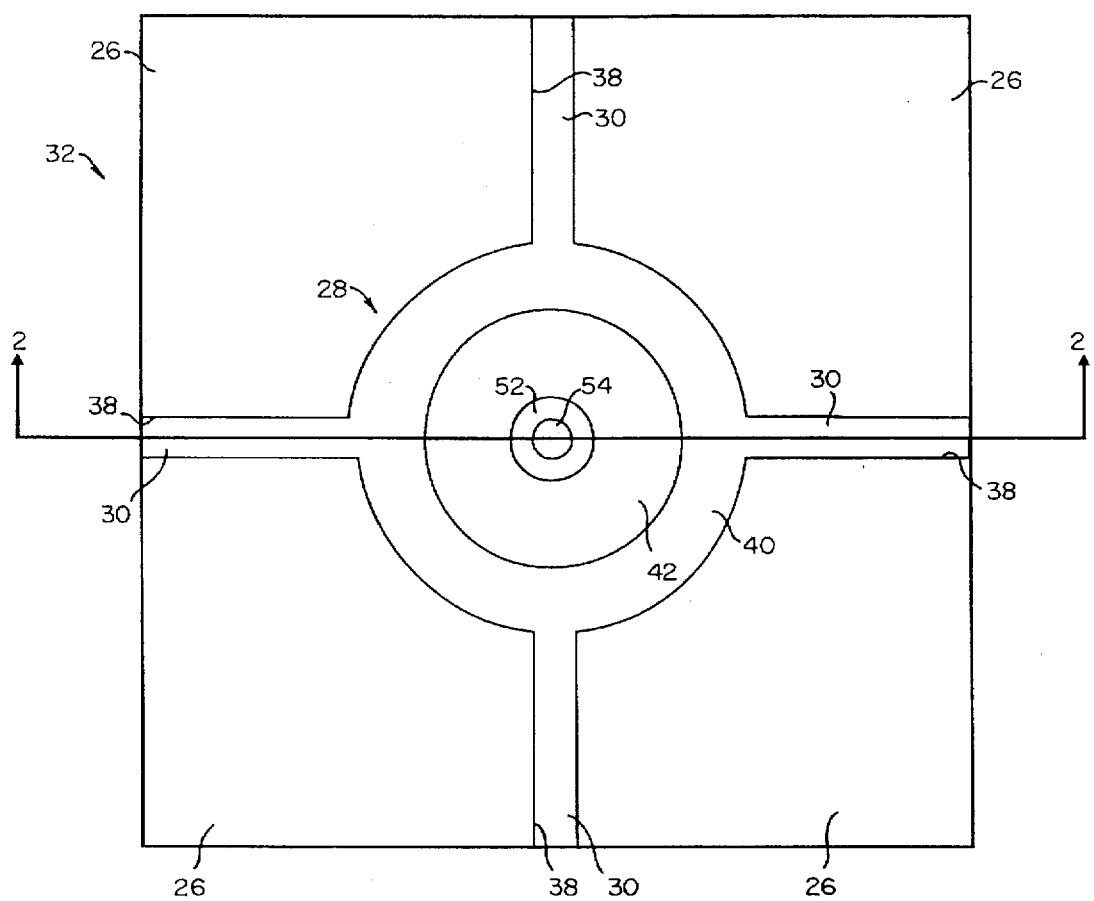
FIG. 1 is a top elevational view of a micromachined radial flow regulator of the present invention.
Figure 2:
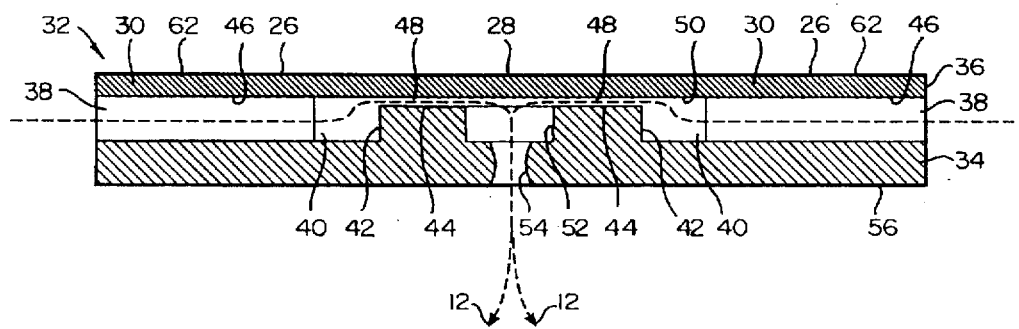
FIG. 2 is a cross-sectional view thereof, taken substantially along line 2—2 of FIG. 1.

Turning now to FIGS. 1–2, the micromachined radial flow regulator 32 of the present invention may be used to control the flow rate of a fluid medication 12 passing through it. The term "medication" is used in its broad sense throughout this document, and may be any fluid, whether or not the fluid is medicinal in nature; unless the context should indicate otherwise. Similarly, the term "fluid" is also used in its broad sense throughout this document, and may include both liquids and gasses; unless the context should indicate otherwise.

The radial flow regulator 32 may comprise a substrate 34 and a membrane 36. The substrate 34 may have four radially oriented inlet channels 38, a ring-shaped inlet cavity 40, a ring-shaped regulator seat 42, a cylindrical outlet cavity 52, and a venturi-shaped outlet port 54. In FIG. 1, the membrane 36 is depicted as being transparent, for clarity, so that the substrate 34's various features may be seen more easily.

The membrane 36 may have four mounting portions 26, which are mounted to respective portions of the substrate 34's top surface 46; a circular, flexible flexure 28, which lies over the inlet cavity 40 and the regulator seat 42; and four inlet channel cover portions 30, each of which lie over a respective inlet channel 38. Although the membrane 36 is illustrated as being of uniform thickness, and as having flat bottom and top surfaces 50, 62, the membrane 36 may not be of uniform thickness, and may have bottom and top surfaces 50, 62 which are not flat. Although the membrane 36 is illustrated as having four mounting portions 26, it may have fewer or more mounting portions 26.

A ring-shaped regulator gap 48 is provided between the regulator seat 42 and the flexure 28.

Figure 9:
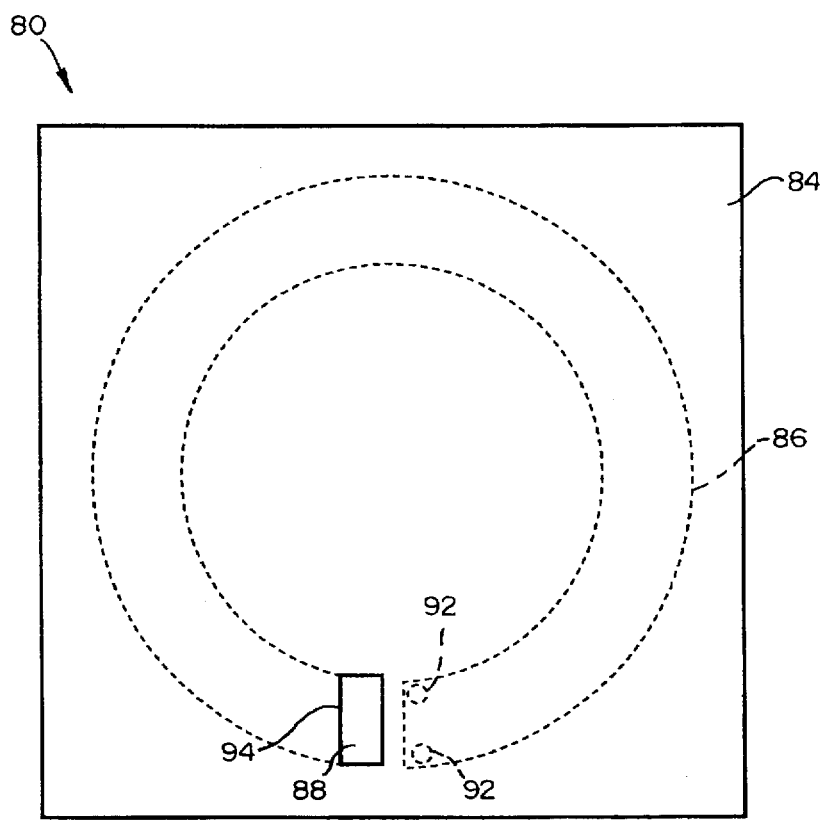
FIGS. 9–11 are top elevational views of three additional embodiments thereof.
Figure 10:
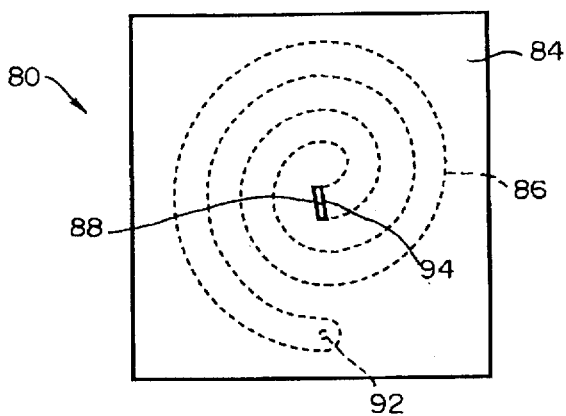
Figure 11:
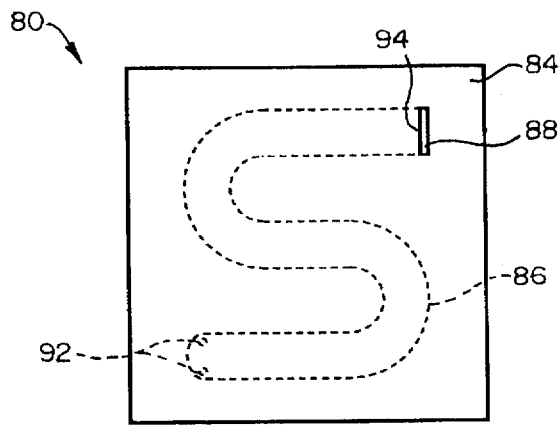

Although four, straight, radially oriented inlet channels 38 are illustrated, each having a rectangular cross-sectional configuration and a respective cover portion 30, there may be fewer or more inlet channels 38, each having a respective cover portion 30; any particular inlet channel 38 may size any other suitable size and cross-sectional configuration, such as square or rounded; the length of any particular inlet channel 38 may be varied; and any particular radial inlet channel 38 need not follow a straight, radially oriented course, but may follow a circular, spiral, serpentine, or other non-straight, non-radially oriented course, such as do the channels 86 of the regulators 80 of FIGS. 9–11. The use of one or more inlet channels 38 following a circular, spiral, serpentine, or other non-straight, non-radially oriented course may be desirable since it may permit the manufacture of a radial flow regulator 32 which is more compact, as compared to a radial flow regulator 32 having straight, radially oriented inlet channels 38.

Although the ring-shaped inlet cavity 40 is illustrated as having a circular or cylindrical configuration, and a uniform depth, it may have any other suitable size and configuration, and a non-uniform depth. In addition, although the inlet channels 38 and the inlet cavity 40 are illustrated as being separate elements, it is understood that these elements may be merged into each other so that they are no longer distinct elements. This may be done in any suitable way, such as by enlarging the inlet channels 38 until they perform most, if not all, of the functions of the inlet cavity 40; by enlarging the inlet cavity 40 until it performs most, if not all, of the functions of the inlet channels 38; or by any combination of the forgoing two ways.

Although the ring-shaped regulator seat 42 is illustrated as having a circular or cylindrical configuration, a flat top surface 44, and a uniform thickness, it may have any other suitable size and configuration, a top surface 44 which is not flat, and a non-uniform thickness.

Although the ring-shaped regulator gap 48 is illustrated as having a circular or cylindrical configuration, and a uniform height, it may have any other suitable size and configuration, and a non-uniform height. Although the regulator gap 48 is illustrated as being formed by selecting the regulator seat 42 to have a thickness such that its top surface 44 is lower than the portions of the substrate 34's top surface 46 to which the membrane 36's mounting portions 26 are secured, the regulator gap 48 may be formed in any other suitable way. For example, the regulator seat 42's top surface 44 and the substrate 34's top surface 46 may be selected to be co-planar, and the regulator gap 48 may be formed by reducing the thickness of the portion of the flexure 28 which overlies the regulator 42 by an amount equal to the desired height of the regulator gap 48. Alternatively, the regulator gap 48 may be formed by a combination of the two forgoing ways.

Although a single outlet cavity 52, and a single outlet port 54 are illustrated, there may be more than one of each of these elements.

Although an outlet cavity 52 having a circular or cylindrical configuration and a uniform depth is illustrated, it may have any other suitable size and configuration, and a non-uniform depth. The outlet cavity 52 may be used to define a clean outer perimeter for the outlet port 54, particularly if the outlet port 54 is drilled with a laser. However, the outlet cavity 52 may be eliminated, and the outlet port 54 may be extended upwardly so that it communicates directly with the regulator gap 48. Alternatively, the outlet port 54 may be eliminated, and the outlet cavity 52 may be extended downwardly so that it communicates directly with the regulator 32's bottom surface 56.

Although an outlet port 54 having a venturi-shaped configuration is illustrated, it may have any other suitable configuration, such as round or cylindrical.

Although the inlet cavity 40, the regulator seat 42, the regulator gap 48, the outlet cavity 52 and the outlet port 54 are illustrated as being uniformly arranged with respect to each other around a common center, they may be arranged with respect to each other in any other suitable way, and may not have a common center.

The regulator 32 may have a flow rate for medical applications in the range of from about 0.01 cc/day to about 20 cc/day; and preferably in the range of from about 0.1 cc/day to about 2.0 cc/day. However, it is understood that, in view of all of the disclosures contained in this document, the radial flow regulator 32 may be scaled up or down in size to regulate higher or lower flow rates of the medication 12.

Figure 5:
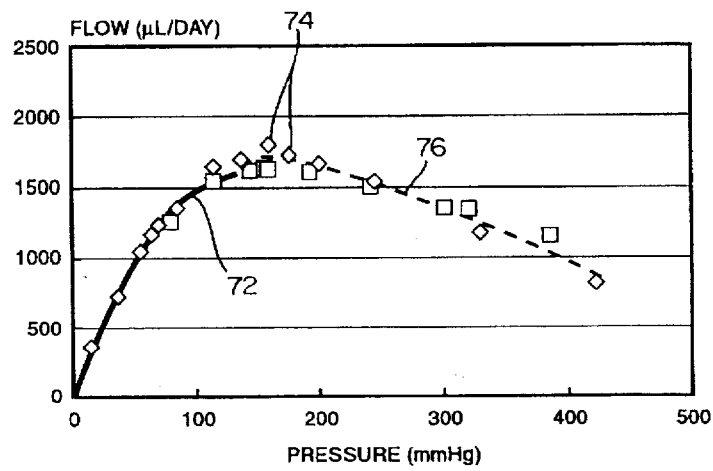
FIGS. 5 and 6 are graphs depicting certain further fluid flow characteristics thereof.
Figure 6:
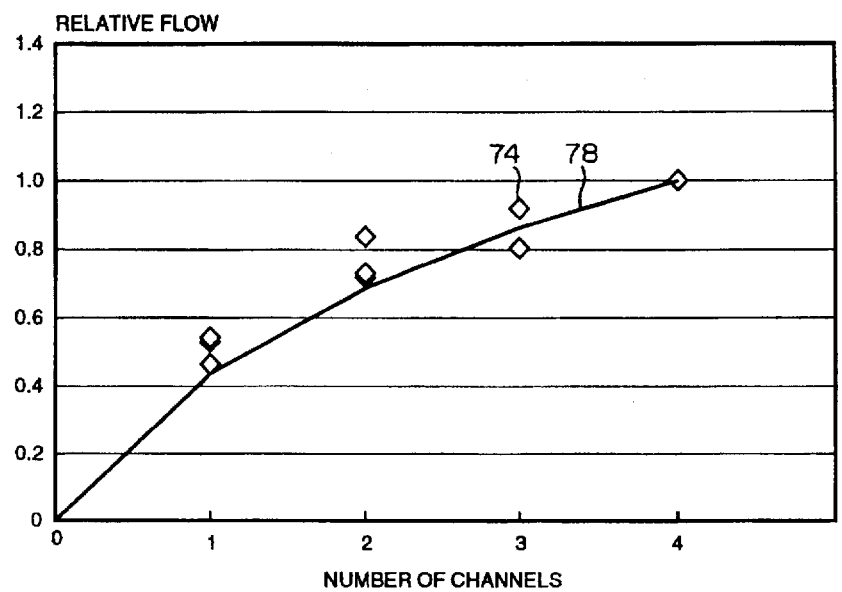

By way of example, the chip bearing the radial flow regulator 32 may be a square having sides about 4.83 mm long. Its membrane 36 may be manufactured from silicon; and may have a thickness of about 25 microns. Its substrate 34 may have a thickness of about 0.5 mm, and may be manufactured from 7740 Pyrex glass, manufactured by the Corning Company located in Corning N.Y. The inlet channels 38 may have a length of about 2.54 mm, a width of about 107 microns, and a depth of about 5.65 microns. The ring-shaped inlet cavity 40 may have a depth of about 5.65 microns, an O.D. (outer diameter) of about 2.29 mm, and an I.D. (inner diameter) of about 1.52 mm, (i.e., the ring-shaped cavity 40 may have a radial width of about 0.77 mm). The ring-shaped regulator seat 42 may have an O.D. of about 1.52 mm and an I.D. of about 0.5 mm, (i.e. the ring-shaped regulator seat 42 may have a radial width of about 1.02 mm). The ring-shaped regulator gap 48 may have a height of about 2.5 microns, when the driving pressure difference (P) across the flexure 28 is zero; and may have a radial width of about 1.02 mm. The outlet cavity 52 have a width of 0.5 mm, and a depth of about 3.15 microns. The outlet port 54 may have a minimum diameter of about 100 microns, and a depth of about 494 microns. The flow characteristics of this example radial flow regulator 32 are illustrated in FIGS. 5 and 6.

As will be appreciated from all of the disclosures in this document, the fact that the regulator 32 may, as in the example set forth above, have an extremely small size, be extremely light weight, have only two parts, and have a zero electrical energy consumption, offer numerous advantages over a regulator 32 which was physically much larger, much heavier, more complex or consumed electrical energy. For example, the regulator 32 may be ideal for use as part of a miniaturized medication delivery device which is to be implanted in a human or animal for delivery of constant flows of the medication 12 at flow rates as low as about 0.01 cc/day—flow rates which are so low that they may be impossible for a physically larger flow regulator of a different design to reliably and accurately deliver.

MICROMACHINED RADIAL FLOW REGULATOR 32 (FIGS. 1–6): OPERATION AND DESIGN

The radial flow regulator 32 may be installed in its intended location of use in any suitable way. Any suitable medication supply means may be used to connect the radial flow regulator 32's inlet channels 38 to a source of the medication 12; and any suitable medication delivery means may be used to connect the radial flow regulator 32's outlet port 54 to whatever person, animal or thing is to receive the medication 12 from the outlet port 54. In some cases, the medication supply means may also be used to supply the medication 12 to the flexure 28's top surface 62, at a pressure which may or may not be the same as the pressure at which the medication 12 is supplied to the inlet channels 38.

For example, the radial flow regulator 32 may be installed within any type of reservoir means for the medication 12 by any suitable means, such as by locating the radial flow regulator 32's outlet port 54 over the reservoir means's outlet, and by using an adhesive face seal between the radial flow regulator 32's bottom surface 56 and the inside of the reservoir means to hold the radial flow regulator 32 in place. As a result, when the reservoir means is filled with the medication 12, the radial flow regulator 32 will be immersed in the medication 12, with its inlet channels 38 and its flexure 28's top surface 62 in fluid communication with the medication 12 within the reservoir means, and with its outlet port 54 in fluid communication with the reservoir means' outlet. Such an installation for the radial flow regulator 32 has numerous advantages.

For example, it is quick, easy, reliable and inexpensive, because no additional medication supply means (such as supply conduits) are needed to supply the medication 12 to the radial flow regulator 32's inlet channels 38 and to the flexure 28's top surface 62 (since they are already immersed in the medication 12); and because no additional medication delivery means (such as delivery conduits) are needed to convey the medication 12 away from radial flow regulator 32's outlet port 54 (since the reservoir means' outlet is used for this purpose). Such additional inlet and outlet conduits may be undesirable since it may be relatively time consuming, difficult and expensive to align and connect them to radial flow regulator 32, due to the extremely small size of its inlet channels 38, flexure 28, and outlet port 54. Such additional inlet conduits may also be undesirable because they may tend to trap a bubble when being filled with a liquid medication 12, which bubble might then be carried into the radial flow regulator 32 and cause it to malfunction.

In the discussion which follows it will be assumed, for clarity and simplicity, that during operation of the radial flow regulator 32, the flexure 28's top surface 62 and the entrances of the inlet channels 38 are all exposed to a pressurized source of the medication 12 from the medication supply means. It will also be assumed, for clarity and simplicity, that the driving pressure difference (P) of the medication 12 across the radial flow regulator 32 is the pressure difference between the medication 12 at the membrane 36's top surface 62, and the medication 12 at the outlet port 54; which is the same as the pressure difference between the medication 12 at the entrances of the inlet channels 38 and the outlet port 54. However, it is understood that during operation of the radial flow regulator 23, these pressure differences need not be equal, and the flexure 28's top surface 62 does not necessarily have to be exposed to the pressurized source of the medication 12 from the medication supply means.

When the flexure 28's top surface 62 is exposed to the medication 12, the driving pressure difference (P) across the flexure 28 may be the dominant factor in determining the amount of deflection of the flexure 28, and thus, the size of the regulator gap 48. On the other hand, if the flexure 28's top surface 62 is not exposed to the medication 12, then the velocity of the medication 12 through the regulator gap 48 may be the dominant factor in determining the amount of the deflection of the flexure 28, and thus, the size of the regulator gap 48.

During operation, as a driving pressure difference (P) is applied across the radial flow regulator 32, such as by pressurizing the source of the medication 12 with respect to the radial flow regulator 32's outlet port 54 by any suitable means, the medication 12 will pass sequentially through the radial flow regulator 32's inlet channels 38, inlet cavity 40, regulator gap 48, outlet cavity 52, and outlet port 54. The inlet cavity 40 may serve to more or less equally distribute the flow of the medication 12 from the inlet channels 38 to the entire circumference of the regulator gap 48, for more predictable operation of the radial flow regulator 32.

Figure 3:
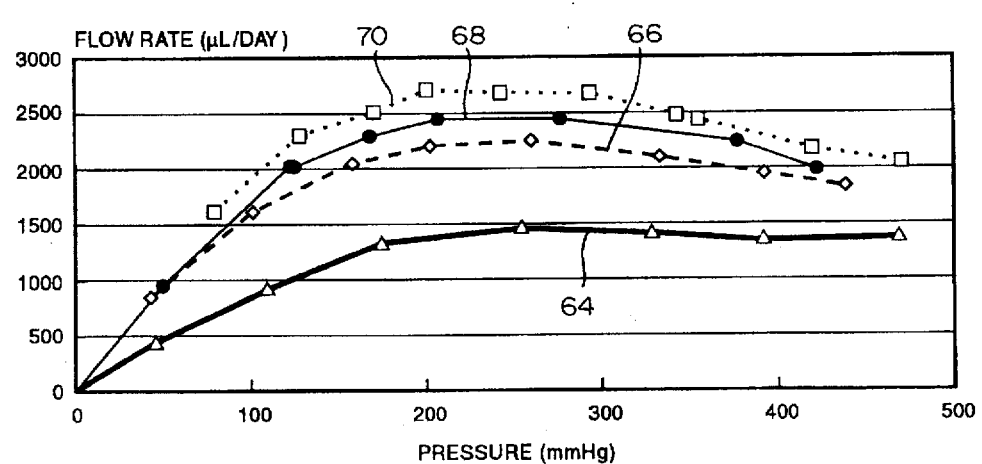
FIG. 3 is a graph depicting certain of the fluid flow characteristics thereof.

Referring now to FIG. 3, the regulator curves 64, 66, 68 and 70 are illustrated for a radial flow regulator 32 having one, two, three and four radial inlet channels 38, respectively. The triangular, diamond, circular and square data points on the regulator curves 64, 66, 68 and 70 are for the measured flow rate (Q) of an actual radial flow regulator 32 having the physical parameters of the example radial flow regulator 32 which was set forth above.

The regulator curves 64, 66, 68 and 70, as well as all of the data points in FIG. 3, are plots of the flow rate (Q) of the medication 12 through the radial flow regulator 32 in microliters per day (µL/day), as a function of the driving pressure difference (P) across the radial flow regulator 32 in millimeters of mercury (mm Hg).

As seen in FIG. 3, at a zero driving pressure difference (P) there is no flow of the medication 12 through the radial flow regulator 32, regardless of how many inlet channels 38 there may be. Then, as the driving pressure difference (P) is increased from zero, the radial flow regulator 32 exhibits four flow regimes, again regardless of the number of inlet channels 38 which it may have.

That is, as the driving pressure difference (P) is increased from zero, there is a corresponding increase of the flow rate (Q); but there is also a gradual lessening of the flow rate's (Q's) sensitivity to the driving pressure difference (P). For example, this is seen on the curve 66 from about a 0 mm Hg to about a 200 mm Hg driving pressure difference (P).

At intermediate driving pressure differences (P) there is a "control zone" wherein the flow rate (Q) is relatively insensitive changes in the driving pressure difference (P). For example, this is seen on the curve 66 from mm Hg to about 300 mm Hg.

Then, at driving pressure differences (P) higher than the "control zone", the flow rate (Q) actually decreases as the driving pressure difference (P) increases. For example, this is seen on the curve 66 from about 300 mm Hg to about 450 mm Hg.

Finally, at very high driving pressure differences (P), not illustrated in FIG. 3, the flow rate (Q) may gradually decrease to near zero as the driving pressure difference (P) of the medication 12 acting on the flexure 28's top surface 46 drives the flexure 28 down against the regulator seat 42.

It has been discovered that the radial flow regulator 32 has a built-in, fail-safe characteristic, due to its structure, that may provide the user with exceptional protection against catastrophic failure of the flexure 28, when the flexure 28 is subjected to driving pressure differences (P) that are far in excess of the regulator 32's designed driving pressure difference (P) range.

This fail-safe characteristic exists because, as has been mentioned, at very high driving pressure differences (P) the medication 12 acting on the flexure 28's top surface 46 may drive the flexure 28 down against the regulator seat 42's top surface 44. When this happens, the regulator seat 42 then acts as a support for the flexure 28 and prevents its further downward deflection; which further deflection might otherwise cause the flexure 28 to crack or rupture. As a result, a much higher driving pressure difference (P) is required to rupture the flexure 28 than would otherwise be the case, since the largest unsupported span of the flexure 28 is reduced in size from the maximum overall diameter of the inlet cavity 40, to the much smaller radial width of the ring-shaped inlet cavity 40. For example, for a flexure 28 which was a membrane of silicon about 25 microns thick, a driving pressure difference of at least about 100 psi (5.171 mm Hg) would be required to crack or rupture the flexure 28. By way of comparison, as seen in FIG. 3, the regulator 32's typical operating driving pressure difference (P) may be only about 300 mm Hg. Thus, in this instance, the regulator 32 would have about a 17 times overpressure safety factor.

The type of response curves 64, 66, 68, 70 shown in FIG. 3 is highly desirable for many applications. This is because the radial flow regulator 32 will deliver a relatively constant flow rate (Q) of the medication 12 in its nominal "control zone", despite a substantial range of variations in the driving pressure difference (P). In addition, if the nominal "control zone" driving pressure difference (P) is exceeded, then the flow rate (Q) of the medication 12 will not increase, but will actually decrease; thereby avoiding the possibility of damage which might otherwise be caused if the flow regulator 32 permitted more than the desired amount of the medication 12 to flow.

For example, let us assume that a medication delivery device, having a source of medication 12 under pressure, was equipped with a radial flow regulator 32 in order to control the flow rate (Q) of the medication 12 from the medication delivery device. As a result, such a medication delivery device may be designed for operation in the radial flow regulator 32's above nominal "control zone" where the flow rate (Q) is relatively insensitive to changes in the driving pressure difference (P). This may be highly desirable, since the patient will receive the medication 12 at the needed flow rate (Q); despite any variations in the driving pressure difference (P), such as may be caused by the gradual emptying of the medication delivery device. In addition, if the nominal "control zone" driving pressure difference (P) were to be substantially exceeded, such as if a medical person accidentally overfilled the medication delivery device, then the medication flow rate (Q) will actually fall, thereby significantly reducing the possibility of injury or death to the patient, due to an overdose of medication 12, which might otherwise occur.

The radial flow regulator 32 tends to maintain the flow rate (Q) of the medication 12 at a relatively constant value in its "control zone", despite changes in the driving pressure difference (P), in the following way. If the driving pressure difference (P) increases, then the flexure 28 will tend to be deflected downwardly towards the regulator seat 42 an increased amount, thereby reducing the height of the regulator gap 48. This, in turn, tends to maintain the flow rate (Q) at a relatively constant value, despite the increased driving pressure difference (P). This is because the reduced height of the regulator gap 48 will tend to compensate for the increased driving pressure difference (P) by reducing the flow rate (Q) which would otherwise occur at that increased driving pressure difference (P).

On the other hand, if the driving pressure difference (P) decreases, then the flexure 28 will tend to be deflected downwardly towards the regulator seat 42 a decreased amount, thereby increasing the height of the regulator gap 48. This, in turn, tends to maintain the flow rate (Q) at a relatively constant value, despite the reduced driving pressure difference (P). This is because the increased height of the regulator gap 48 will tend to compensate for the reduced driving pressure difference (P) by increasing the flow rate (Q) which would otherwise occur at that reduced driving pressure difference (P).

Lastly, at driving pressure differences (P) above the regulator 32's "control zone", the flow rate (Q) is gradually reduced to near zero, as the flexure 28 is driven down closer and closer to the regulator seat 42.

Although the radial flow regulator 32 is deceptively simple in appearance, it has been discovered that it is not possible to develop simple, generally applicable design rules for its construction. This is in large part attributable to the close and nonlinear compensatory coupling between the flow rate (Q) through the radial flow regulator 32's regulator gap 48 and the flow resistance of the regulator gap 48 ($R_s$); which, in turn, makes it difficult to separate cause and effect in a mathematical sense.

In addition, certain other problems arise in developing simple, generally applicable design rules for the radial flow regulator 32 because the flow rates (Q) of the medication 12 through the regulator 32 may be so low, (as low as about 0.01 cc per day), and because the dimensions of the inlet channels 38, the inlet cavity 40, the regulator gap 48, the outlet cavity 52 and the outlet port 54 may be so small, (as small as about 0.1 microns).

As a result of such low flow rates (Q) and such small dimensions, certain fluid flow effects (such as the viscous shear forces of the medication 12 acting to deform various parts of the radial flow regulator 36), which are normally negligible in predicting the performance of physically larger flow regulators, which handle flow rates of over about 0.1 cc per minute, for example, may become very important. In addition, certain other fluid flow effects (such as the Equation of Continuity and Bernoulli's Equation), which are normally important for physically larger flow regulators, handling such higher flow rates (Q), may become negligible for a regulator 32 having such low flow rates (Q) and such small dimensions. And, at intermediate flow rates (Q) and dimensions, a combination of the pertinent small scale and large scale fluid flow effects may have to be taken into account.

Because of all of the above problems, it has been discovered that two quite different strategies may be used to assist in designing a radial flow regulator 32 which has any particular desired flow regulation characteristics.

The first strategy is one which is empirical in nature. That is, a series of flow regulators 32 may be built, and one feature at a time may be varied, so that the effects of changing that particular feature may be determined.

For example, the series flow resistance ($R_s$) of the regulator gap 48 may be independently varied by holding constant the regulator gap 48's initial height (when the driving pressure difference (P) is equal to zero); while varying the width of the ring-shaped regulator seat 42, such as by varying the I.D. and O.D. of the ring-shaped regulator seat 42. Similarly, the regulator gap 48's initial height (when the driving pressure difference (P) is equal to zero) may be varied; while holding constant the width of the ring shaped regulator seat 42, such as by holding constant the I.D. and O.D. of the ring-shaped regulator seat 42.

By building and testing a large number of radial flow regulators 32; by then plotting data points for each of them for their various flow rates (Q) versus their driving pressure differences (P); and by then curve-fitting the plotted data points, it has been discovered that it is possible to generate an empirical model for the performance of the radial flow regulator 32 which shows the relationships between key features of the radial flow regulator 32 and the operating behavior of the radial flow regulator 32. These empirical relationships may then be used to interpolate or extrapolate from known design cases to predict the behavior of a new radial flow regulator 32.

For example, it has been discovered that the radial flow regulator 32's flow rate set point ($Q_{set}$) (the average flow rate (Q) of the radial flow regulator 32 over its "control zone") obeys power-law relationships with respect to many of the radial flow regulator 32's design features. That is, it has been discovered that if the series flow resistance ($R_s$) of the regulator gap 48, and the regulator gap 48's initial height (when the driving pressure difference (P) is equal to zero), are independently varied, then the radial flow regulator 32's flow rate set point ($Q_{set}$) may be described over a considerable range of values by an equation of the form:

$$Q_{set} = \frac{aG^m}{R_s^n}$$

where ($Q_{set}$) and ($R_s$) are as have been defined above; where (G) is the regulator gap 48's initial height (when the driving pressure difference (P) is equal to zero); and where (a) is a constant.

For example, for a radial flow regulator 32 having a silicon flexure 28 with a thickness of about 25 microns; having channels 38 with a width of about 107 microns, with a depth of about 5.65 microns, and a length of about 2.54 mm; having a ring-shaped inlet cavity 40 with an O.D. of about 2,300 microns, and a depth of about 5.65 microns; having a ring-shaped regulator seat 42 with a width (as measured between its I.D. and O.D.) of about 750–2,000 microns; having an initial regulator gap 48 height (when the driving pressure difference (P) is equal to zero) in the range of about 2–3 microns; having an outlet cavity 52 about 5.65 microns deep; and having an outlet port 54 with a minimum diameter of about 100 microns and a length of about 494 microns, it has been discovered that (m) is on the order of about 2.4 and (n) is on the order of about ⅔.

The second strategy which may be used to assist in designing a radial flow regulator 32 which has any particular desired flow regulation characteristics is to develop a sophisticated physical model using numerical methods.

The starting point for formulating the model may be that, for any particular radial flow regulator 32, the flow of the medication 12 through it may be generally governed by the following equation:

$$Q = \frac{P}{R_{ch} + R_s(Q)}$$

where (Q), (P), and ($R_s$) are as has been defined above; where ($R_{ch}$) is the combined flow resistance across the radial inlet channels 38; where ($R_{ch}$) is a direct function of the length (L) and the wetted perimeter (C) of each of the radial inlet channels 38; where ($R_{ch}$) is an inverse function of the cross-sectional area (A) of each of the radial inlet channels 38; and where ($R_s$) is a nonlinear function of the flow rate (Q).

Figure 4:
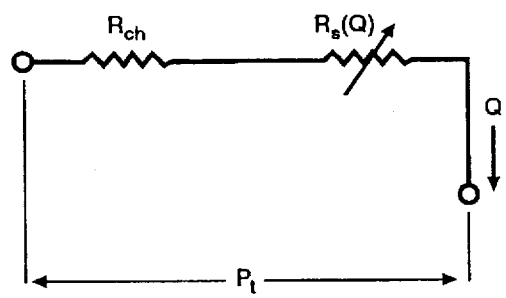
FIG. 4 is a schematic diagram of some of the fluid characteristics thereof.

That is, the flow rate (Q) is proportional to the driving pressure difference (P), and is inversely proportional to the sum of the two flow resistances ($R_{ch}$) and ($R_s$). A circuit diagram illustrating this behavior is shown in FIG. 4.

It has been found that accurate prediction of the nonlinear flow resistance ($R_s$) of the regulator gap 48 may require the consideration of at least the following four factors.

First, the nonlinear flow resistance ($R_s$) of the regulator gap 48 may be a function of the pressure drop across the inlet channels 38, due to their flow resistance ($R_{ch}$). This is because the greater the pressure drop across the inlet channels 38, the greater the driving pressure difference (P) across the flexure 28, and the greater the amount of the deflection of the flexure 28 (and vice versa). This, in turn, generally decreases the height of the regulator gap 48; thereby generally increasing the flow resistance ($R_s$) of the regulator gap 48 (and vice versa). However, such deflection of the flexure 28 is not uniform, since the deflected flexure 28 is not flat, but instead assumes a convex, or bowed shape. This results in the nonlinear flow resistance ($R_s$) of the regulator gap 48 being a relatively complex function of the flow resistance ($R_{ch}$) of the inlet channels 38.

Second, the nonlinear flow resistance ($R_s$) of the regulator gap 48 may be a function of the viscous shear forces of the medication 12 acting on the flexure 28's bottom surface 50 as the medication 12 flows radially inwardly through the regulator gap 40, from the inlet cavity 40 to the outlet cavity 52. Such viscous shear forces are, in turn, a function of such things as the viscosity and velocity of the medication 12 in the regulator gap 48. Such viscous shear forces are directed radially inwardly on the flexure 28's bottom surface 50, and tend to twist or distort the flexure 28's bottom surface 50 with respect to the flexure 28's top surface 62. Such twisting or distorting of the flexure 28 tends to vary the size and shape of the regulator gap 48 which, in turn, varies the flow resistance ($R_s$) of the regulator gap 48. This results in the nonlinear flow resistance ($R_s$) of the regulator gap 48 being a relatively complex function of the viscous shear forces of the medication 12 acting on the flexure 28.

Third, the nonlinear flow resistance ($R_s$) may be a function of the velocity of the medication 12 passing through the regulator gap 48. Such velocity is, in turn, a function of such factors as the flow resistance ($R_{ch}$) of the inlet channels 38; the driving pressure difference (P) across the regulator 32; the height, size and shape of the regulator gap 48; and the flow resistance ($R_s$) of the regulator gap 48.

Because of the Equation of Continuity and Bernoulli's Equation, as the velocity of the medication 12 through the regulator gap 48 increases, the pressure of the medication within the regulator gap 48 tends to decrease (and vice versa). This is because the Equation of Continuity requires that the velocity of the medication 12 must increase at a restriction. Thus, since the regulator gap 48 is a restriction (as compared to the inlet cavity 40), the velocity of the medication 12 must increase as it flows through the regulator gap 48. Bernoulli's equation then requires that the pressure of the medication 12 in the regulator gap 48 must fall, due to its increased velocity as it flows through the regulator gap 48.

That is, as the velocity of the medication 12 in the regulator gap 48 increases, the pressure of the medication 12 in the regulator gap 48 decreases. This increases the amount of the deflection of the flexure 28; which, in turn, generally decreases the height of the regulator gap 48 and increases the flow resistance ($R_s$) (and vice versa).

Fourth, the nonlinear flow resistance ($R_x$) may be a function of the flexure 28's thickness, resiliency, elasticity and stiffness. This is because for any given forces acting on the flexure 28, the amount of the deflection of the flexure 28, and the shape (or radial profile) of the deflected flexure 28, may be a function of the flexure 28's thickness, resiliency, elasticity and stiffness.

In the forgoing discussion, it was assumed that the membrane 36's inlet channel cover portions 30 were selected such that they would not be deflected a substantial amount downwardly into the inlet channels 38 by the medication 12 during the operation of the radial flow regulator 32. Thus, the forgoing discussion assumed that substantially none of the regulation of the flow of the medication 12 by the flow regulator 32 was done by any such deflection of the 36's inlet channel cover portions 30.

However, this need not be the case since, as will be made apparent by all of the disclosures in this document, regulation of the flow rate (Q) of the medication 12 through the radial flow regulator 32 may be at least partially done by such deflection of the membrane 36's inlet channel cover portions 30.

From the forgoing, it is seen that the primary difficulty in developing a sophisticated physical model for the radial flow regulator 32 which uses numerical methods is that the amount of the deflection or bowing of the flexure 28, and the shape of the flexure 28 as it deflects or bows, are closely coupled and nonlinear in interaction. As a result, iterative techniques may be used to generate a solution for the flexure 28's deflected or bowed shape (a) that is correct at every point of contact between the medication 12 and the flexure 28 in terms of the forces applied to the flexure 28; and (b) that simultaneously provides a consistent radial gradient of the driving pressure difference (P) of the medication 12 across the flexure 28 which obeys the laws of fluid flow.

To do this, a free body diagram may first be developed for an arbitrary ring-shaped segment of the flexure 28. This model creates the following governing fourth-order differential equation set that identifies the relationship between the flexure 28's local curvature and its thickness; Young's modulus and Poisson's ratio; and exterior forcing functions that include the shear between the medication 12 and the flexure 28, any driving pressure difference (P) across the flexure 28, and the flexure 28's radial tension. The governing fourth-order differential equation set may be determined in the following way.

The first derivative of the deflection (θ) of the flexure 28 towards the regulator seat 42 is given by the following second order differential equation:

$$\frac{d^2\theta}{dr^2} + \frac{1}{r}\frac{d\theta}{dr} - \frac{\theta}{r^2} = \frac{-1}{rD_t}\int_r^o r\Delta P(r)dr \qquad \text{Equation 1}$$

where r is radial position with respect to the center of the flexure 28; $\Delta P(r)$ is the driving pressure difference across the flexure 28 at the radial position r; and $D_t$ is given by:

$$D_t = \frac{Et^3}{12(1-v^2)}$$

where E is Young's Modulus; t is the thickness of the flexure 28; and v is Poisson's ratio.

The actual deflection Y(r) of the flexure 28 is obtained by integrating above Equation 1:

$$1Y(r) = Y_o + \int_r^o \theta(r)dr \qquad \text{Equation 2}$$

where $Y_o$ is the centerline deflection of the flexure 28. Hence the governing differential equation set is fourth order.

Next, a first-order differential equation may be developed for the flexure 28's driving pressure difference (P) pressure drop across the annular ring-shaped portion of the regulator gap 48 which is directly under the above mentioned arbitrary ring-shaped segment of the flexure 28. This differential equation must take into account not only the change in the regulator gap 48 caused by the amount of the deflection or bowing of the flexure 28, but also any change in the regulator gap 48 caused by the substrate 34's inlet channels 38 and inlet cavity 40. The first-order differential equation for the driving pressure difference $\Delta P(r)$ is:

$$\Delta P(r) = \Delta P_1 - \frac{6\mu Q}{\pi}\int_R^r \frac{dr}{r(H(r)-Y(r))^3} \qquad \text{Equation 3}$$

where $\Delta P_1$ is the driving pressure difference (P) at the outer rim of the inlet cavity 40, referenced to the constant pressure of the medication 12 external to the flexure 28; Q is the volumetric flow rate of the medication 12; μ is the viscosity of the medication 12; and H(r) is the height of the regulator gap 48 when the driving pressure difference (P) is equal to zero.

In short, the above Equation 2 describes the amount and shape of the deflection or bowing of the flexure 28; while the above Equation 3 provides a means to calculate the driving pressure difference (P) of the medication 12 across the flexure 28 at any radial position with respect to the flexure 28. To be a physically correct representation of the interaction between the driving pressure difference (P) across the flexure 28, and the amount and shape of the deflection or bowing of the flexure 28, the solutions of the above Equations 2 and 3 must be consistent with each other in a point-to-point sense across the entire radius of the flexure 28.

To achieve this goal, the above Equation 2 may be converted to a finite difference form, and a guess may be made as to the radial profile of the driving pressure difference (P) of the medication 12 across the flexure 28. This is necessary since a solution of the bowing or deflected flexure 28's above Equation 2 requires knowledge of the driving pressure difference (P) of the medication 12 across the flexure 28 at each radial position.

This results in a so-called tridiagonal array of coupled equations that may be solved recursively for the flexure 28's radial slope at each point. Then this may be integrated once to yield the flexure 28's deflection at each radial position. Once this is known, the radial profile of the driving pressure difference (P) across the flexure 28 may be recalculated using these new deflection values for the flexure 28 by integration of the above Equation 3.

The above iterative process may then be continued, as necessary, until the calculated position of the flexure 28 does not change by some arbitrarily set small amount per iteration, thereby signalling a consistent solution set.

Any number of different cylindrically-symmetric fluid flow devices may be modeled with the above equation set. By changing the sign of Q, both inward and outward flow of the medication 12 through the devices may be modeled. By adjusting the function H(r) to reflect the height of the gap between the particular fluid flow device's flexure and the corresponding part of its substrate, the above equation set may be equally useful for modeling flow switches (such as the flow switch 250), one-way valves (such as the one-way valves 210, 240, 300), and other flow regulators (such as the flow regulators 80, 110). In the particular case of one-way valves (such as the one-way valve 300), in which there is a pre-set interference or prestressing between the seat 310 and the flexure 314, that is, the seat 310 protrudes above the plane of the flexure 314's bottom surface 322, it is only necessary to initiate solution of the coupled equations with a trial deflected shape of the flexure 314 that clears the seat 310 and allows the medication 12 to begin to flow radially inwardly across the seat 310.

FIG. 5 shows the above mathematical model being used to predict the response of a typical design for the flow regulator 32. The solid curve 72 in FIG. 5 shows a plot of the above mathematical model for the radial flow regulator 32, in terms of flow of the medication 12 through the regulator 32 in µL/day as a function of the driving pressure difference (P) across the flexure 28.

The diamond-shaped data points 74 which are plotted in FIG. 5 are for a typical radial flow regulator 32 having a radial array of four rectangular inlet channels 38, each having a width of about 70 microns, a length of about 1270 microns, and a depth of about 5.7 microns; an inlet cavity having a maximum diameter of about 2290 microns, and a depth of about 5.7 microns; a regulator seat 42 having an I.D. of about 508 microns, and an O.D. of about 1780 microns; a flexure manufactured from a membrane of silicon having a thickness of about 25 microns; a regulator gap 48 having a height of about 2.5 microns (when the driving pressure difference (P) across the flexure 28 is zero); an outlet cavity having a diameter of about 508 microns, and a depth of about 5.7 microns; and an outlet port having a minimum diameter of about 100 microns, and a length of about 494 microns.

The dashed curve 76 is an empirical curve which is derived by applying curve-fitting techniques to the plotted data points 74. As seen in FIG. 5, agreement between the theoretical curve 72 and the plotted data points 74 is very good.

The curve 78 in FIG. 6 shows the above mathematical model being used to predict the reduction in the medication 12's flow rate setpoint ($Q_{set}$) caused by sealing off the four inlet channels 38 one-by-one. The diamond-shaped data points 74 which are plotted in FIG. 6 are for a typical radial flow regulator 32 having the physical parameters which were set forth above.

As seen in FIG. 6, when one inlet channel 38 is sealed off, the effective combined flow resistance ($R_{ch}$) of the remaining three channels 38 increases by about 33%, as compared to the combined flow resistance ($R_{ch}$) of the original array of four inlet channels 38. Similarly, plugging two and three of the inlet channels 38 will increase the effective combined flow resistance ($R_{ch}$) of the remaining inlet channel(s) 38 by about 100% and about 400%, respectively. As seen in FIG. 6, the mathematical model curve 78 predicts this behavior of the radial flow regulator 32 very well.

The qualitative effect of closing off one or more of the inlet channels 38 is to increase the driving pressure difference (P) across the flexure 28 which is needed for any given flow rate (Q) of the medication 12 through the radial flow regulator 32. This causes the flexure 28 to come into closer proximity to the regulator seat 42 at a lower flow rate (Q), and hence biases the regulator 32's flow rate setpoint ($Q_s$) to a value for the flow rate (Q) which is lower than would otherwise be the case.

It has been discovered that, as seen in FIG. 3, as the number of the inlet channels 38 is decreased, the "control zone" of the flow rate (Q) occurs at lower and lower flow rates (Q) for any given driving pressure difference (P) across the radial flow regulator 32. It has also been discovered that, as is also seen in FIG. 3, as the number of the inlet channels 38 is decreased, there may be a reduced sensitivity in the rate of change of the flow rate (Q) for any given change in the driving pressure difference (P) in the "control zone" of the flow rate (Q). However, the theoretical grounds for this behavior of the regulator 32 are not clear, and it is possible that this behavior may be due to an artifact in a regulator 32 which is imperfect.

All of the forgoing is very important, since it has been discovered that a single radial flow regulator 32 may actually have the properties of four different regulators 32, depending on whether none, one, two or three of its inlet channels 38 are sealed. That is, as seen in FIG. 3, such regulators 32 have quite different regulation curves 64, 66, 68, 70; have quite different "control zones" and flow rate set points ($Q_{set}$); have quite different flow rates (Q) for any given driving pressure difference (P); and have quite different sensitivities to changes in their flow rates (Q) for any given change in the driving pressure difference (P).

This makes the present invention much more versatile, since a single radial flow regulator 32 may be easily modified to do the work of four single-function flow regulators. Of course, as was mentioned above, there may be fewer, or more, than four inlet channels 38; so one radial flow regulator 32 may be easily modified to do the work of fewer or more single-function flow regulators 32.

From the disclosures in this document, it is possible to selectively design a radial flow regulator 32 for any particular desired flow regulation characteristics or driving pressure difference (P). This may be done by selectively adjusting one or more of the pertinent parameters, such as: (a) the number, length, size, and cross sectional configuration of the radial inlet channels 38; (b) the number, size, cross-sectional configuration and location of the cavities 40, 52 and the outlet port 54; (c) the number, size, cross-sectional configuration and height of the regulator seat 42; (d) the number, size, cross-sectional configuration and height of the regulator gap 48; and (e) the thickness, resiliency, elasticity and stiffness of the membrane 36.

For example, it has been discovered that by adjusting the fraction of the driving pressure difference (P) that is dropped across the radial inlet channels 38 in relation to the fraction of the driving pressure difference (P) which is dropped across the regulator gap 48 (by adjusting the flow resistance ($R_{ch}$) of the inlet channels 38 and the flow resistance ($R_s$) of the regulator gap 48 with respect to each other), two things may be selectively modified. First, the degree of control of the regulator flow (Q) versus the driving pressure difference (P) may be selectively varied; and second, the amount of regulator flow (Q) versus the driving pressure difference (P) may also be selectively varied.

MICROMACHINED RADIAL FLOW REGULATOR 32 (FIGS. 1–6): MANUFACTURE

The substrate 34 may be manufactured from any suitable strong, durable material which is compatible with the medication 12, and in which the inlet channels 38, the inlet cavity 40, the regulator seat 42, the outlet cavity 52, and the outlet port 54 may be manufactured in any suitable way, such as by using any suitable etching, molding, stamping and machining process. Such a machining process may include the use of physical tools, such as a drill; the use of electromagnetic energy, such as a laser; and the use of a water jet.

The membrane 36 may be manufactured from any suitable strong, durable, flexible, material which is compatible with the medication 12.

If the radial flow regulator 32 is intended to regulate a medication 12 which is to be supplied to a human or an animal, then any part of the regulator 32 which is exposed to the medication 12 should be manufactured from, and assembled or bonded with, nontoxic materials. Alternatively, any toxic material which is used to manufacture the regulator 32, and which is exposed to the medication 12 during use of the regulator 32, may be provided with any suitable non-toxic coating which is compatible with the medication 12.

Suitable materials for the substrate 34 and the membrane 36 may be metals (such as titanium), glasses, ceramics, plastics, polymers (such as polyimides), elements (such as silicon), various chemical compounds (such as sapphire, and mica), and various composite materials.

The substrate 34 and the membrane 36 may be assembled together in any suitable leak-proof way. Alternatively, the substrate 34 and the membrane 36 may be bonded together in any suitable leak-proof way, such as by anodically bonding them together; such as by fusing them together (as by the use of heat or ultrasonic welding); and such as by using any suitable bonding materials, such as adhesive, glue, epoxy, solvents, glass solder, and metal solder.

Anodically bonding the substrate 34 and the membrane 36 together may be preferable for at least four reasons. First, anodic bonding is relatively, quick, easy and inexpensive. Second, an anodic bond provides a stable leak-proof bond.

Third, since an anodic bond is an interfacial effect, there is no build-up of material at the bond; and the bond has essentially a zero thickness, which desirably creates no essentially no spacing between the substrate 34 and the membrane 36. As a result, an anodic bond does not interfere with the desired height of the regulator gap 32.

Fourth, an anodic bond may be preferable since it eliminates the need for any separate bonding materials, which might otherwise clog or reduce the size of the inlet channels 38, the inlet cavity 40, the regulator seat 42, the regulator gap 48, the outlet cavity 52, and the outlet port 54; or which might lead to corrosion of the joint between the regulator 32's substrate 34 and membrane 36.

One example of how the radial flow regulator 32 may be manufactured will now be given. The starting point may be a 76.2 mm diameter wafer of Corning 7740 Pyrex glass, which will form the regulator 32's substrate 34.

The glass wafer may be cleaned in any suitable way, such as by immersing it in a buffered hydrofluoric acid (BHF) etchant for two minutes, rinsing it with distilled water, and drying it.

A thin chrome metallization layer may then applied to the top surface of the glass wafer by any suitable means, such as with an electron beam evaporator. The chrome layer may provide a good adhesion surface for the subsequent application of photosensitive resist (photoresist) to the glass wafer's top surface.

Following this, a thin layer of any suitable photoresist may be applied on top of the chrome layer, such as Microposit 1650 photoresist made by the Shipley Company, located in Newton, Mass. The layer of photoresist may be dried in any suitable way, such as by baking it at about 90° C. for about 25 minutes.

An image of the four radial inlet channels 38, the inlet cavity 40, and the outlet cavity 52 may then be exposed onto the photoresist in any suitable manner, such as by using a first mask and a mask aligner. This image may be developed (that is, the exposed photoresist may be removed), by using any suitable photoresist developer, such as 351 developer, made by the above Shipley Company. The glass wafer may then be then rinsed in distilled water and dried.

As a result of the forgoing procedure, the chrome layer will now bear an image, unprotected by the photoresist, of the four radial inlet channels 38, the inlet cavity 40, and the outlet cavity 52. The unprotected portions of the chrome layer may then be removed by using any suitable chrome etch solution, such as Cyantek CR-7, made by the Cyantek Company, located in Fremont, Calif.

The forgoing procedure will result in an image of the four radial inlet channels 38, the inlet cavity 40, and the outlet cavity 52 having been formed on the top surface of the glass wafer, which image is unprotected by the layers of photoresist and chrome which cover the rest of the glass wafer's top surface. The image may then be etched into the glass wafer's top surface to any desired depth by any suitable means, such as by immersing the glass wafer's top surface in BHF etchant; rinsing the glass wafer in distilled water, and drying it. A suitable depth may be about 6.0 microns.

Next, an image of the regulator seat 42 may then be exposed onto the photoresist on the glass wafer's top surface using a second mask. The newly exposed photoresist may then be developed; and the newly exposed portions of the chrome removed. Then the image of the regulator seat may be etched into the top surface of the glass wafer to any desired depth in any suitable manner, in order to define an elevation difference between the regulator seat 42's top surface 44 and the top surface of the glass wafer. A suitable elevation difference may be about 2.5 microns.

At this point, it may be noted that the depths of the four radial inlet channels 38, the inlet cavity 40, and the outlet cavity 52 will also have been automatically increased by about 2.5 microns, since they are also unprotected by the layers of chrome and photoresist. In other words, the four radial inlet channels 38, the inlet cavity 40, and the outlet cavity 52 may intentionally be initially etched to a depth less than their desired final depth, in order to permit them to automatically and simultaneously reach their desired final depth while the regulator seat 42 was being etched.

Note that the above procedure is unusually economical and quick, since if the four radial inlet channels 38, the inlet cavity 40, and the outlet cavity 52 were originally etched to their desired final depth, then the additional steps of re-coating the entire glass wafer with photoresist (in order to protect the etched four radial inlet channels 38, the inlet cavity 40, and the outlet cavity 52), and then baking the photoresist, would have to be done prior to the exposing, developing and etching of the regulator seat 42.

After the regulator seat 42 has been etched, the regulator 32's outlet port 54 may be formed by any suitable means, such as by drilling it with a focused beam from a 25 W $CO_2$ laser, with a physical drill, or with a water jet drill. It has been discovered that when using a laser to form the outlet port 54, heating the glass wafer to near its anneal point improves the quality of the outlet port 54, and also reduces undesirable cracking of the glass wafer adjacent to the outlet port 54.

Preferably, as seen in FIG. 2, the outlet port 54 may have a venturi-like shape, rather than being cylindrical in shape, for better fluid flow through it. It has also discovered that the outlet port 54 may be given its preferred venturi-like shape by drilling the outlet port 54 with a laser in the manner discussed above. The desired venturi-like shape may be automatically formed during the laser drilling process, and apparently results from the thermal effects of the laser beam interacting with the glass wafer as the outlet port 54 is being drilled through it with the laser beam. After the outlet port 54 has been drilled, the glass wafer may be lightly etched with BHF etchant, in order to remove any volatilized glass which may have condensed on the glass wafer adjacent to its outlet port 54.

After the outlet port 54 has been formed, a nominal layer of one or more corrosion-resistant substances may be deposited onto the top surface of the glass wafer by any suitable means, such as by sputtering using an e-beam evaporator. As a result, the four radial inlet channels 38, the inlet cavity 40, the regulator seat 42, the outlet cavity 52, and the outlet port 54 will have been coated with a layer of the corrosion-resistant substance(s).

Suitable corrosion-resistant substances may be silicon, or may be metals, such as gold, platinum, chrome, titanium and zirconium, or may be the oxides of silicon or such metals. Such oxides may be formed by thermally oxidizing the corrosion-resistant substance(s) in air after it has been applied to the substrate 34. However, other suitable corrosion-resistant substances may be used, depending on the particular medication 12 with which the radial flow regulator 32 is designed to be used. The oxides of metals such as titanium and zirconium are well-known to be stable against water solutions over a wide pH range. The thickness of the layer of the corrosion-resistant substance(s) may be from 200 Å–1000 Å; but the thickness may depend on the particular corrosion-resistant substance(s) being used, and on the particular medication 12 with which the radial flow regulator 32 is designed to be used.

Alternatively, the layer of corrosion-resistant substance (S) may comprise a donut-shaped disk of such corrosion-resistant substance(s), such as silicon, which may be bonded to the regulator seat 42's top surface 44 by any suitable means, such as by using any of the means which have been mentioned for bonding the substrate 34 and the membrane 36 together.

Such a corrosion-resistant donut-shaped disk may be formed in any suitable way, such as by using a masking and etching process which is similar to that described above regarding the substrate 34. The starting point may be a clean epitaxial-coated silicon wafer, to which is applied a thin chrome metallization layer and a layer of photoresist. After the photoresist is dry, an image of the donut-shaped disk may then be exposed onto the photoresist. The exposed photoresist, and the underlying portions of the chrome layer, may then be removed, resulting in an image of the donut-shaped disk on the surface of the silicon wafer, which image is not protected by the photoresist or by the chrome layer. The exposed portions of the silicon wafer may then etched to a depth in excess of the desired thickness of the desired donut-shaped disk in any suitable way, such as by the use of an isotropic silicon etchant. For example, if a donut-shaped disk having a thickness of about 1 micron was desired, then the exposed portions of the silicon wafer may be etched to a depth of about 5 microns.

The silicon wafer may then be cleaned; the etched faces of the silicon and glass wafers may then be aligned with each other, so that the donut-shaped disk on the silicon wafer is aligned with the regulator seat 42 on the glass wafer; and the silicon and glass wafers may then be bonded together in any suitable way, such as by using an anodic bonding process like that which will be described below regarding anodically bonding together the silicon and glass wafers that will form the regulator 32's substrate 34 and membrane 36. Next, the silicon wafer with the donut-shaped disk may then etched again in any suitable way, such as by the use of an anisotropic ethylene diamine etchant, until the desired ultimate thickness of the donut-shaped disk of silicon is obtained.

The manufacture of only one substrate 34 and only one donut-shaped disk of corrosion-resistant material for the substrate 34's regulator seat 42 was described above. However, it will be appreciated that on any pair of glass and silicon wafers respective arrays of substrates 34 and corresponding donut-shaped disks of corrosion-resistant material may be manufactured simultaneously in a manner which is similar to that described above. If such is the case, the array of substrates 34 on the glass wafer may be aligned with, and then bonded to, the corresponding array of donut-shaped disks of corrosion-resistant material on the silicon wafer. After the final etching of the silicon wafer, the manufacture of each regulator 32 may then be completed in the manner which is set forth below.

If a donut-shaped disk or layer of corrosion-resistant substance(s) is bonded or applied to the regulator seat 42, then the regulator seat 42 may have to be etched an additional amount during its above etching step prior to applying the donut-shaped disk or layer of corrosion-resistant substance(s) to the regulator seat 42's top surface 44. The additional amount of etching may be equal to the thickness of the donut-shaped disk or layer, in order to end up with the desired elevation difference between the regulator seat 42's top surface 44 and the top surface of the glass wafer (which will form the substrate 34).

It has been discovered that the donut-shaped disk or layer of corrosion-resistant substance(s) on the regulator seat 42's top surface 44 may serve an unexpected further function in addition to its corrosion-resistant function. That is, it may also prevent the regulator 32's membrane 36 from being inadvertently bonded to the regulator seat 42's top surface 44 when the membrane 36 is being bonded to the glass wafer, such as when the membrane 36 is being anodically bonded in the manner which will be described below.

After the regulator seat 42 has been etched, and after any desired layer or disk of corrosion-resistant substance(s) has been applied to etched portions of the glass wafer, the photoresist and chrome which remain on the unetched portions of the glass wafer may be removed by any suitable means, such as by using standard lift-off techniques.

Fabricating the membrane 36 and mounting it to the glass wafer (which is the substrate 34), may be done in any suitable way.

One suitable way is to start with a prime silicon wafer having a boron-doped epitaxial silicon layer which has been deposited onto its top surface. Since the boron doped epitaxial silicon layer will ultimately form the regulator 32's membrane 36, the layer's thickness will depend on the desired thickness of the membrane 36. The boron-doped epitaxial silicon layer, and thus the membrane 36, may be from 1–50 microns thick, for example. The boron doping may be in excess of $3 \times 10^{19}$ atoms of boron per cubic centimeter, which conveys a dramatic etch-resistance to the epitaxial silicon layer in silicon etchants based on ethylene diamine.

The glass and silicon wafers may then be cleaned; dried; and anodically bonded together. The anodic bonding may be performed in any suitable way, such as by placing the respective top surfaces of the glass and silicon wafers in contact with each other in a vacuum chamber in an oven maintained at a temperature of about 500° C. A DC voltage of approximately 1000 volts may then be applied to the two wafers for a period of about 15 minutes, with the silicon wafer at a positive potential relative to the bottom surface of the glass wafer. An exponentially decaying current will flow through the wafers over this time period, at the end of which the two wafers will have been anodically bonded together, i.e., they will have been hermetically bonded to each other to form a silicon/glass sandwich. It has also been discovered that the anodic bonding process may also ensure that any corrosion-resistant substance(s) which were applied to the etched surfaces of the glass wafer are firmly attached to it.

Upon cool-down, after the anodic bonding process is complete, the silicon wafer portion of the anodically bonded silicon/glass sandwich may be ground down; but preferably, the silicon wafer is not ground down so much that any of its boron doped epitaxial silicon layer is removed. For example, if the boron doped epitaxial silicon layer is from about 1–50 microns in thickness, then the silicon wafer portion of the bonded silicon/glass wafer sandwich may be ground down to about 125 microns in thickness. The remaining non-doped silicon in the silicon wafer may then be removed in any suitable way, such as by placing the ground down silicon/glass sandwich in an ethylene diamine etchant maintained at 112° C. for 3.5 to 4.0 hours. A suitable ethylene diamine etchant may be PSE-300, manufactured by the Transene Corp. located in Rowley, Mass. At the end of this time, the boron doped epitaxial silicon layer will be exposed in the form of a continuous, flat membrane 36 which is anodically bonded to the glass wafer (the substrate 34), thereby forming the completed radial flow regulator 32, which is then cleaned and dried.

The purpose of the above grinding step is simply to reduce the amount of silicon which needs to be etched away. Accordingly, as alternatives, the grinding step may be eliminated, with all of the undesired silicon being etched away; or a thinner silicon wafer may be used, so that there is less undesired silicon to begin with.

The manufacture of only one radial flow regulator 32 was described above. However, it will be appreciated that on any pair of glass and silicon wafers numerous regulators 32 could be manufactured simultaneously in a manner similar to that described above. If such is the case, an array of substrates 34 may be simultaneously etched in the glass wafer before the silicon and glass wafers are aligned and bonded together. Then, all of the membranes 36 may be formed simultaneously by grinding and etching the silicon wafer to its desired final thickness. The silicon/glass sandwich may then be divided by any suitable means (such as dicing) into individual chips, each chip bearing at least one radial flow regulator 32.

One of the advantages of using the etching and anodic bonding process which was described in detail above is that such a process enables high quality, very reliable radial flow regulators 32 to be mass produced in great numbers at a cost so low that the regulator 32 may be considered to be disposable. In addition, it should also be noted that the regulator 32 is stunning in its simplicity since it may have as few as only two parts (the substrate 34 and the membrane 36); and since it may have only one moving part (the membrane 36's flexure 28). Further, because the raw materials from which the regulator 32 may be manufactured may be very inexpensive, such as glass and silicon, the cost of the regulator 32 may held to a very low level.

MICROMACHINED LINEAR FLOW REGULATOR 80 HAVING A CONTOURED REGULATOR SEAT 90 (FIGS. 7–12):
STRUCTURE

Figure 7:
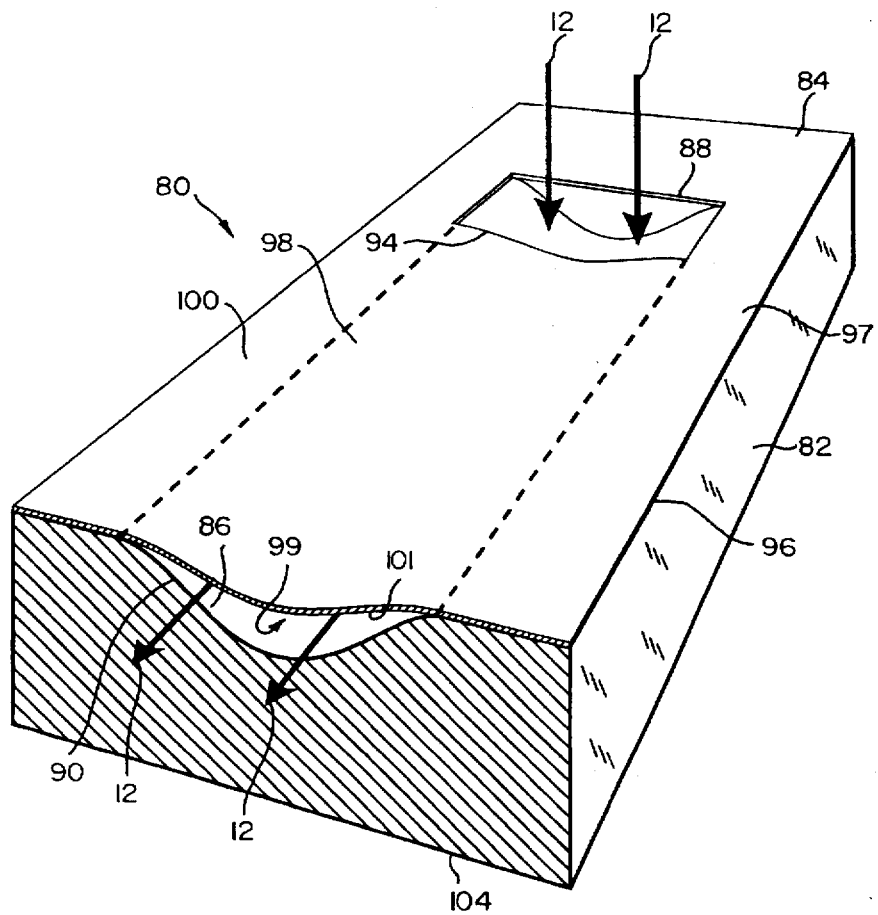
FIG. 7 is a perspective view, partly in a cross-section taken substantially along line 7—7 of FIG. 8, of a micromachined linear flow regulator of the present invention having a contoured regulator seat.
Figure 8:
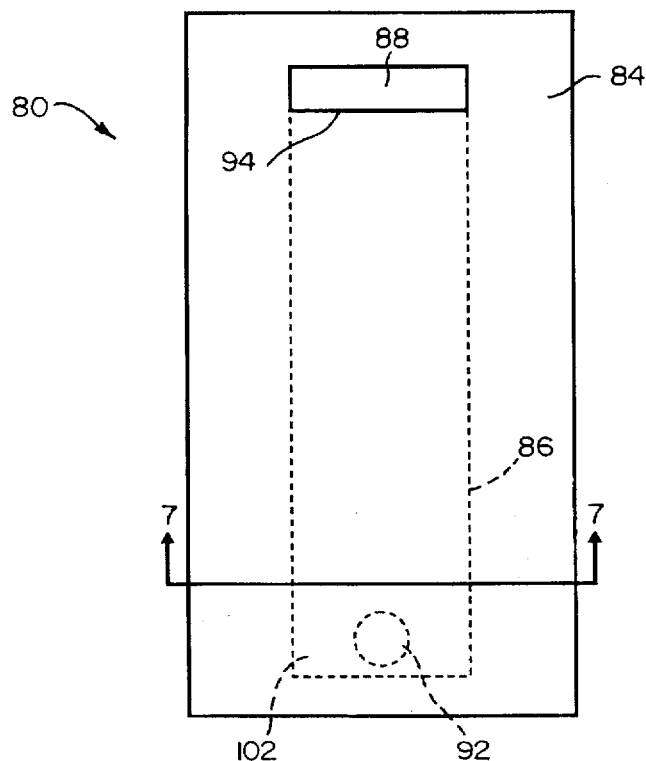
FIG. 8 is a top elevational view thereof.

Turning now to FIGS. 7–8, the micromachined linear flow regulator 80 of the present invention is illustrated. The linear flow regulator 80 may be used to control the flow rate of a fluid medication 12 passing through it, and may comprise a substrate 82, and a membrane 84. The substrate 82 may include a straight, elongated channel 86 having a contoured regulator seat 90 and an outlet port 92. The membrane 84 may have a mounting portion 97, which is mounted to a corresponding portion of the substrate 82's top surface 96; an inlet port 94; and a flexure 98 which overlies the channel 86. A regulator gap 99 lies between the flexure 98 and the regulator seat 90.

Although only one outlet port 92 in the substrate 82 is illustrated, there may be more outlet ports 92. Although, as seen, the outlet port 92 is preferably located near one end of the channel 86, so that during operation of the regulator 80 the downwardly deflecting flexure 98 will not seal off the outlet port 92, each outlet port 92 may be positioned in any other suitable location in the channel 86. Although preferably the outlet port 92 may have a venturi-like shape, for better flow of the medication 12 through it, the outlet port 92 may have any other suitable shape. Although the outlet port 92 is illustrated as being located in the substrate 82, the outlet port 92 may be wholly or partially located in the membrane 84.

Although the channel 86 and the regulator seat 90 which are illustrated in FIGS. 7–8 follow a straight course, the channel 86 and the regulator seat 90 may follow a circular (FIG. 9), spiral (FIG. 10), serpentine (FIG. 11), or other non-straight course. The use of a regulator 80 having a channel 86 and a regulator seat 90 which follow a circular, spiral, serpentine, or other non-straight course may be desirable. This is because, for any given length of channel 86 and regulator seat 90, such courses may permit the manufacture of a linear regulator 80 which is more compact, as compared to a linear regulator 80 having a straight channel 86 and regulator seat 90.

Preferably, the contour of the regulator seat 90 may approximate, or duplicate, the contoured shape that the flexure 98 would assume if the flexure 98 were entirely unrestrained by any part of the substrate 82 when the linear flow regulator 80 is subjected to the regulator 80's maximum designed driving pressure difference (P) of the medication 12 between the regulator 80's inlet port 88 and outlet port 92.

Although the membrane 84 is illustrated as being of uniform thickness, and as having flat top and bottom surfaces 100, 101, the membrane 84 may not be of uniform thickness, and may have top and bottom surfaces 100, 101 which are not flat.

Although the membrane 84 shown has one rectangular inlet port 88, there may be more than one inlet port 88, and each inlet port 88 may have any other suitable shape. Although the inlet port 88 is illustrated as being in the membrane 84, the inlet port 88 may be wholly or partially located in the substrate 82.

Figure 12:
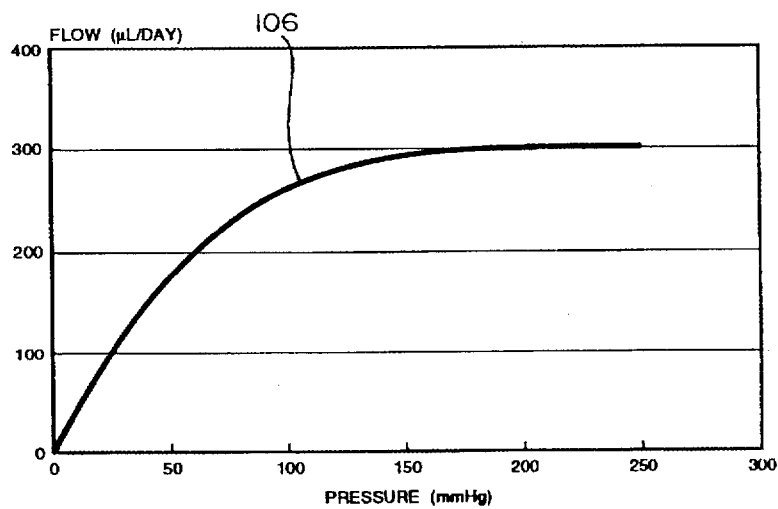
FIG. 12 is a graph depicting certain fluid flow characteristics thereof.

By way of example, the linear flow regulator 80's substrate 82 may be manufactured from 7740 Pyrex glass, and may have a thickness of about 0.5 mm. The channel 86 and the regulator seat 90 may each have a length of about 10 mm, and a maximum width of about 480 microns. The regulator gap 99 may have a maximum height of about 6.65 microns (when the driving pressure difference (P) is equal to zero). The outlet port 92 may have a minimum diameter of about 100 microns, and may have a length of about 496 microns. The membrane 84 may be manufactured from silicon, and may have a thickness of about 4.0 microns. The inlet port 88 may have a width of about 480 microns, and a length of about 500 microns. The flow characteristics of this example linear flow regulator 80 are illustrated in FIG. 12, which will be discussed below.

Turning now to FIGS. 9–11, the linear flow regulators 80 illustrated therein are the same as, or at similar to, the linear flow regulator 80 of FIGS. 7–8, in their structure, operation, theory, and manufacture, except for those differences, if any, which will be made apparent by an examination of all of the Figures and disclosures in this document. Accordingly, the respective parts of the linear flow regulators 80 of FIGS. 9–11 have been given the same reference numerals as the corresponding parts of the linear flow regulator 80 of FIGS. 7–8, for clarity and simplicity.

One of such differences is that the linear flow regulators 80 illustrated in FIGS. 9 and 11 have a pair of outlet ports 92, instead of the single outlet port 92 of the regulator 80 of FIGS. 7–8. Other of such differences are that the channel 86 and the regulator seat 90 of the regulator 80 illustrated in FIGS. 7–8 follow a straight course, while the channels 86 and the regulator seats 90 of the regulators 80 of FIGS. 9–11 follow a circular, spiral, and serpentine course, respectively.

As will be appreciated from all of the disclosures in this document, the fact that the linear flow regulators 80 may, as in the example set forth above, have an extremely small size, be extremely light weight, have only two parts, and have a zero electrical energy consumption, offer numerous advantages over a regulator 80 which was physically much larger, much heavier, more complex, or which consumed electrical energy. For example, the regulators 80 may be ideal for use as part of a miniaturized medication delivery device which is to be implanted in a human or animal for delivery of constant flows of the medication 12 at flow rates as low as about 0.01 cc/day—flow rates which are so low that they may be impossible for a physically larger flow regulator of a different design to reliably and accurately deliver.

MICROMACHINED LINEAR FLOW
REGULATOR 80 HAVING A CONTOURED
REGULATOR SEAT 90 (FIGS. 7–12):
OPERATION AND THEORY

The linear flow regulator 80 may be installed in its intended location of use in any suitable way. Any suitable medication supply means may be used to connect the regulator 80's inlet port 88 to a source of the medication 12; and any suitable medication delivery means may be used to connect the regulator 80's outlet port 92 to whatever person, animal or thing is to receive the medication 12 from the outlet port 92. In some cases, the medication supply means may also be used to supply the medication 12 to the flexure 98' top surface 100, at a pressure which may or may not be the same as the pressure at which the medication 12 is supplied to the inlet port 88.

For example, the regulator 80 may be installed within any type of reservoir means for the medication 12 by any suitable means, such as by locating the regulator 80's outlet port 92 over the reservoir means's outlet, and by using an adhesive face seal between the regulator 80's bottom surface 104 and the inside of the reservoir means to hold the regulator 80 in place. As a result, when the reservoir means is filled with the medication 12, the regulator 80 will be immersed in the medication 12, with its inlet port 88 and its flexure 98's top surface 100 in fluid communication with the medication 12 within the reservoir means, and with its outlet port 92 in fluid communication with the reservoir means' outlet. Such an installation for the regulator 80 has numerous advantages.

For example, it is quick, easy, reliable and inexpensive, because no additional medication supply means (such as supply conduits) are needed to supply the medication 12 to the regulator 80's inlet port 88 and to the flexure 98's top surface 100 (since they are already immersed in the medication 12); and because no additional medication delivery means (such as delivery conduits) are needed to convey the medication 12 away from regulator 80's outlet port 92 (since the reservoir means' outlet is used for this purpose). Such additional inlet and outlet conduits may be undesirable since it may be relatively time consuming, difficult and expensive to align and connect them to regulator 80, due to the extremely small size of its inlet port 88, flexure 98, and outlet port 92. Such additional inlet conduits may also be undesirable because they may tend to trap a bubble when being filled with a liquid medication 12, which bubble might then be carried into the regulator 80 and cause it to malfunction.

In the discussion which follows it will be assumed, for clarity and simplicity, that during operation of the regulator 80, the flexure 98's top surface 100 and the inlet port 88 are both exposed to a pressurized source of the medication 12 from the medication supply means. It will also be assumed, for clarity and simplicity, that the driving pressure difference (P) of the medication 12 across the regulator 80 is the pressure difference between the medication 12 at the flexure 98's top surface 100, and the medication 12 at the outlet port 92; which is the same as the pressure difference between the medication 12 at the entrance of the inlet port 88 and the outlet port 92. However, it is understood that during operation of the regulator 80, these pressure differences need not be equal, and the flexure 98's top surface 100 does not necessarily have to be exposed to the pressurized source of the medication 12 from the medication supply means.

During operation, as a driving pressure difference (P) is applied across the regulator 80, such as by pressurizing the source of the medication 12 with respect to the regulator 80's outlet port 92 by any suitable means, the medication 12 will pass sequentially through the regulator 80's inlet port 88, regulator gap 99, and outlet port 92.

Referring now to FIG. 12, the regulator curve 106 is illustrated for the regulator 80. The regulator curve 106 is a plot of the flow rate (Q) of the medication 12 through a regulator 80 having the physical parameters of the example regulator 80 which was set forth above. In FIG. 12, the flow rate (Q) is plotted in terms of microliters per day (μL/day), as a function of the driving pressure difference (P) across the regulator 80 in mmHg (millimeters of mercury).

As seen in FIG. 12, at a zero driving pressure difference (P), there is no flow of the medication 12 through the regulator 80. Then, as the driving pressure difference (P) is increased from zero, the regulator 80 exhibits four flow regimes.

That is, as the driving pressure difference (P) is increased from zero, there is a corresponding increase of the flow rate (Q); but there is also a gradual lessening of the flow rate's (Q's) sensitivity to the driving pressure difference (P). For example, this is seen on the curve 106 at driving pressure differences (P) from about 0.0 mmHg to about 160 mmHg.

At intermediate driving pressure differences (P) there is a "control zone" wherein the flow rate (Q) is relatively insensitive changes in the driving pressure difference (P). For example, this is seen on the curve 106 at driving pressure differences (P) from about 160 mmHg to about 250 mmHg.

Then, although not illustrated in FIG. 12, at driving pressure differences (P) higher than the "control zone", the flow rate (Q) may actually decrease as the driving pressure difference (P) increases. Finally, at very high driving pressure differences (P), the flow rate (Q) may gradually decrease to near zero as the driving pressure difference (P) of the medication 12 acting on the flexure 98's top surface 100 drives the flexure 98 down against the regulator seat 90.

It has been discovered that the regulator 80 has a built-in, fail-safe characteristic, due to its structure, that may provide the user with exceptional protection against catastrophic failure of the flexure 98, when the flexure 98 is subjected to driving pressure differences (P) that are far in excess of the regulator 80's designed driving pressure difference (P) range.

This fail-safe characteristic exists because, as has been mentioned, at very high driving pressure differences (P) the medication 12 acting on the flexure 98's top surface 100 may drive the flexure 98 down against the regulator seat 90. When this happens, the regulator seat 90 then acts as a support for the flexure 98 and prevents its further downward deflection; which further deflection might otherwise cause the flexure 98 to crack or rupture. As a result, a much higher driving pressure difference (P) is required to rupture the flexure 98 than would otherwise be the case.

The type of response curve 106 shown in FIG. 12 is highly desirable for many applications. This is because the regulator 80 will delivery a relatively constant flow rate (Q) of the medication 12 in its nominal "control zone", despite a substantial range of variations in the driving pressure difference (P). In addition, if the nominal "control zone" driving pressure difference (P) is exceeded, then the flow rate (Q) of the medication 12 will not increase, but may actually decrease; thereby avoiding the possibility of damage which might otherwise be caused if the flow regulator 32 permitted more than the desired amount of the medication 12 to flow.

For example, let us assume that a medication delivery device, having a source of medication 12 under pressure, was equipped with a linear flow regulator 80 in order to control the flow rate (Q) of the medication 12 from the medication delivery device. As a result, such a medication delivery device may be designed for operation in the regulator 80's above nominal "control zone" where the flow rate (Q) is relatively insensitive to changes in the driving pressure difference (P). This may be highly desirable, since the patient will receive the medication 12 at the needed flow rate (Q); despite any variations in the driving pressure difference (P), such as may be caused by the gradual emptying of the medication delivery device. In addition, if the nominal "control zone" driving pressure difference (P) were to be substantially exceeded, such as if a medical person accidentally overfilled the medication delivery device, then the medication flow rate (Q) will actually fall, thereby significantly reducing the possibility of injury or death to the patient, due to an overdose of medication 12, which might otherwise occur.

The regulator 80 tends to maintain the flow rate (Q) of the medication 12 at a relatively constant value in its above "control zone", despite changes in the driving pressure difference (P), in the following way. If the driving pressure difference (P) increases, then the flexure 98 will tend to be deflected towards the regulator seat 90 an increased amount, thereby reducing the height of the regulator gap 99. This, in turn, tends to maintain the flow rate (Q) at a relatively constant value, despite the increased driving pressure difference (P). This is because the reduced height of the regulator gap 99 will tend to compensate for the increased driving pressure difference (P) by reducing the flow rate (Q) which would otherwise occur at that increased driving pressure difference (P).

On the other hand, if the driving pressure difference (P) decreases, then the flexure 98 will tend to be deflected towards the regulator seat 90 a decreased amount, thereby increasing the height of the regulator gap 99. This, in turn, tends to maintain the flow rate (Q) at a relatively constant value, despite the reduced driving pressure difference (P). This is because the increased height of the regulator gap 99 will tend to compensate for the reduced driving pressure difference (P) by increasing the flow rate (Q) which would otherwise occur at that reduced driving pressure difference (P).

Lastly, at driving pressure differences (P) above the regulator 80's "control zone" the flow rate (Q) is gradually reduced to zero, as the flexure 98 is driven down closer and closer to the regulator seat 90.

It has been discovered that two quite different strategies may be used to assist in designing a regulator 80 which has any particular desired flow regulation characteristics.

The first strategy is one which is empirical in nature. That is, a series of regulators 80 may be built, and one feature at a time may be varied, so that the effects of changing that particular feature may be determined.

For example, the series flow resistance ($R_s$) of the channel 86 and the regulator gap 99 may be independently varied by holding constant the regulator gap 99's initial height (when the driving pressure difference (P) is equal to zero); while varying the length of the channel 86 and the regulator gap 99. Similarly, the regulator gap 99's initial height (when the driving pressure difference (P) is equal to zero) may be varied by varying the depth and shape of the channel 86; while holding constant the length of the channel 86 and the regulator gap 99.

By building and testing a large number of regulators 80; by then plotting data points for each of them for their various flow rates (Q) versus their driving pressure differences (P); and by then curve-fitting the plotted data points, it may be possible to generate an empirical model for the performance of the regulator 80 which shows the relationships between key features of the regulator 80 and the operating behavior of the regulator 80. These empirical relationships may then be used to interpolate or extrapolate from known design cases to predict the behavior of a new regulator 80.

The second strategy which may be used to assist in designing a regulator 80 which has any particular desired flow regulation characteristics is to develop a mathematical model using numerical methods.

The starting point for formulating the model is that, for any particular regulator 80, the flow of the medication 12 through it may be generally governed by the following equation:

$$Q = \frac{P}{R_s(L, A, C, Q)}$$

where (Q), (P), and ($R_s$) are as has been defined above; where ($R_s$) is a direct function of the length (L) and the wetted perimeter (C) of the channel 86 and the regulator gap 99; where ($R_s$) is an inverse function of the cross-sectional area (A) of the channel 86 and the regulator gap 99; and where ($R_s$) is a nonlinear function of the flow rate (Q).

That is, the flow rate (Q) is proportional to the driving pressure difference (P), and is inversely proportional to the flow resistance ($R_s$) of the channel 86 and the regulator gap 99.

It has been found that accurate prediction of the nonlinear flow resistance ($R_s$) of the channel 86 and the regulator gap 99 may require the consideration of at least the following four factors.

First, the nonlinear flow resistance ($R_s$) of the channel 86 and the regulator gap 99 may be a function of the pressure drop across the length of the channel 86 and the regulator gap 99, due to their flow resistance ($R_s$). This is because the greater the pressure drop across the length of the channel 86 and the regulator gap 99, the greater the driving pressure difference (P) across the flexure 98, and the greater the amount of the deflection of the flexure 98 towards the regulator seat 90 (and vice versa). This, in turn, generally decreases the height of the regulator gap 98; thereby generally increasing the flow resistance ($R_s$) of the channel 86 and the regulator gap 99 (and vice versa). However, such deflection of the flexure 98 is not uniform, since the deflected flexure 98 is not flat, but instead assumes a convex, or bowed shape. This results in the nonlinear flow resistance ($R_s$) of the channel 86 and the regulator gap 48 being a relatively complex function of the pressure drop across the length of the channel 86 and the regulator gap 99.

Second, the nonlinear flow resistance ($R_s$) of the regulator gap 99 may be a function of the viscous shear forces of the medication 12 acting on the flexure 98's bottom surface 101 as the medication 12 flows through the length of the regulator gap 99, from the inlet port 88 to the outlet port 92. Such viscous shear forces are, in turn, a function of such things as the viscosity and velocity of the medication 12 in the regulator gap 99. Such viscous shear forces are directed along the length of the flexure 98's bottom surface 101 and tend to twist or distort the flexure 98's bottom surface 101 with respect to the flexure 98's top surface 100. Such twisting or distorting of the flexure 98 tends to vary the size and shape of the regulator gap 99 which, in turn, varies the flow resistance ($R_s$) of the regulator gap 99. This results in the nonlinear flow resistance ($R_s$) of the regulator gap 99 being a relatively complex function of the viscous shear forces of the medication 12 acting on the flexure 98.

Third, the nonlinear flow resistance ($R_s$) may be a function of the velocity of the medication 12 passing through the regulator gap 99. Such velocity is, in turn, a function of such factors as the driving pressure difference (P) across the regulator 80; the height, size, shape and length of the regulator gap 99; the flow resistance ($R_s$) of the channel 86 and the regulator gap 99; and the size, shape, length and location of the inlet and outlet ports 88, 92.

Because of the Equation of Continuity and Bernoulli's Equation, as the velocity of the medication 12 through the regulator gap 99 increases, the pressure of the medication 12 within the regulator gap 99 tends to decrease (and vice versa). This is because the Equation of Continuity requires that the velocity of the medication 12 must increase at a restriction. Thus, since the regulator gap 99 is a restriction (as compared to the inlet port 94), the velocity of the medication 12 must increase as it flows through the regulator gap 99. Bernoulli's equation then requires that the pressure of the medication 12 in the regulator gap 99 must fall, due to its increased velocity as it flows through the regulator gap 99.

That is, as the velocity of the medication 12 in the regulator gap 99 increases, the pressure of the medication 12 in the regulator gap 99 decreases. This increases the amount of the deflection of the flexure 98; which, in turn, generally decreases the height of the regulator gap 98 and increases the flow resistance ($R_s$) of the channel 86 and the regulator gap 99 (and vice versa).

Fourth, the nonlinear flow resistance ($R_s$) may be a function of the flexure 98's thickness, resiliency, elasticity and stiffness. This is because for any given forces acting on the flexure 98, the amount of the deflection of the flexure 98, and the shape (or radial profile) of the deflected flexure 98, may be a function of the flexure 98's thickness, resiliency, elasticity and stiffness.

From the forgoing, it is seen that the primary difficulty in developing a mathematical model for the regulator 80 which uses numerical methods is that the amount of the deflection or bowing of the flexure 98, and the shape of the flexure 98 as it deflects or bows, are closely coupled and potentially nonlinear in interaction.

However, in developing the mathematical model for the regulator 80, let it now be assumed that the regulator seat 90 has an x,y,z coordinate system in which the z axis lies along the longitudinal centerline of the regulator seat 90; in which the x axis is transverse to the z axis, extends left and right from the z axis, and equals zero at the z axis; and in which the y axis is transverse to the x and z axes, measures the height above the regulator seat 90, and equals zero at the z axis.

In such a coordinate system, the most fundamental flow element consists of a local fluid slice (dx) wide which spans the gap from the regulator seat 90 to the flexure 98. If the bowing or deflection of the flexure 98 is very slight, then it may be assumed that this local fluid slice has negligible shear along its sides and is dominated by viscous drag at its top and bottom. This is a local fluid slice flow approximation. With this assumption, it may be found that the local fluid slice contribution to flow (dQ) is given by:

$$dQ = \frac{\left(\frac{dp}{dz}\right) Y_m^3}{12\mu} \cdot dx \qquad \text{Equation 4}$$

where $\mu$ is the viscosity of the medication 12; and $Y_m(x)$ is the height of the local fluid slice.

The bowing or deflection of the flexure 98 towards the regulator seat 90 may be dictated by the flexure 98's stiffness. For a pressure difference ($P_s - p(z)$) across the flexure 98, the amount (Y) of the bowing or deflection of the flexure 98 is given by:

$$Y = Y_o(1 + X^4 - 2X^2) \qquad \text{Equation 5}$$

where $$Y_o = \frac{(p_s - p)w^4}{2Et^3} \qquad \text{Equation 5A}$$

and where (E) is Young's Modulus; (t) is the thickness of the flexure 98; (w) is the half-width of the regulator seat 90; and (X)=x/w. This assumes that the regulator seat 90 has fixed edges, and that there is a guided condition at the regulator seat 90's center, or at the first point of contact of the flexure 98 with the regulator seat 90. A guided condition means that dY/dx=0 at that point.

If we now solve for the total flow across the local fluid slice cross-section by integrating the above Equation 4, and by incorporating the above Equation 5 to provide the height of the local fluid slice, this is found to be:

$$Q = \frac{E^3 h^4}{\mu w^3} \left(-\frac{dP}{dx}\right) \int_1^o [1 - P \cdot (1 + X^4 - 2X^2)]^3 \, dX \qquad \text{Equation 6}$$

where $$P = \frac{(p_s - p)w^4}{2E t^3 h}$$

and where (h) is equal to the height of the regulator gap 99.

The dimensionless pressure (P) is a variable that is zero when there is no differential pressure, and is 1.0 when the bowing or deflection of the flexure 98 is equal to the height of the regulator gap 99 when there is a zero driving pressure difference (P) across the flexure 98. The integral's value is 0.2781 if P=1. Otherwise, a simple polynomial in P is obtained. It is clear that the total flow (Q) of the medication 12 is a constant throughout the length of the regulator gap 99. This means that for P<1, variables can be separated in the above Equation 6 so that the left side is (z), (Q·dz), and the right side is a polynomial function of P. This can then be integrated to yield a relationship between the flow rate-channel length product, Q·$Z_0$, and pressure at a given axial position:

$$QZ_o = \frac{E t^3 h^4}{6 \mu w^3} P[1 - \frac{4}{5} P + \frac{128}{315} P^2 - \frac{256}{3003} P^3] \quad \text{Equation 7}$$

where ($Z_0$) is the length of the regulator seat 90. This yields a relation between pressure and total flow up to the point where P=1. However at this point, since the regulator seat 90 is assumed to be a perfect replica of the bowed or deflected flexure 98, at a pressure that causes the flexure 98 to touch the center of the regulator seat 90, the flexure 98 is also in contact with the entire regulator seat 90, from side to side. Accordingly, the flow rate-channel length product Q·$Z_0$ is:

$$Q \cdot Z_o = \frac{0.01421 E t^3 h^4}{\mu w^3} \cdot [1 - (1-p)^4]$$

The above model may now be used to predict the performance of the linear flow regulator 80.

Turning again to FIGS. 7 and 8, the flexure 98's inlet port edge 94 may overlie the channel 86, as seen therein, and thus is not affixed to or restrained by any portion of the substrate 82. As a result, all of the flexure 98 which is located adjacent to the inlet port 88 (including the inlet port edge 94), is free to fully flex in response to changes in the flow rate (Q) of the medication 12 through the channel 86; as compared to if the flexure 98's inlet port edge 94 were affixed to or restrained by any portion of the substrate 82. This may be desirable for at least two reasons. First, it may result in smoother, more predictable, regulation of the flow rate (Q) of the medication 12 by the flexure 98 over the regulator 80's designed flow and regulation parameters.

Second, it may also make possible a more compact regulator 80, since the part of the flexure 98 which is located adjacent to the inlet port 88 is not rendered wholly or partially inoperative by any portion of the substrate 82.

Alternatively, the substrate 82 may be manufactured so that part or all of the flexure 98's inlet port edge 94 may be affixed to or restrained by some part of the substrate 82. In order to compensate for such a structure, the channel 86 and the flexure 98 may be lengthened so as to provide the desired overall length of the flexure 98 which is effectively unrestrained by any portion of the substrate 82.

The channel 86 and the flexure 98 may both have a large length to width ratio (L/W), with "large" being defined in this context to be a L/W in the range of about 5:1 to 1000:1. Preferably, the L/W may be about 20:1. A large L/W may be desirable because it may allow the linear flow regulator 80 to have a more robust flexure 98, since the membrane 84's regulator function is distributed over a longer length, as compared to a regulator 80 with a flow channel 86 and a flexure 98 having a small L/W ratio, such as 1:1.

A more robust flexure 98 may be desirable since it may be more durable, it may be less likely to rupture due to undesired operating overpressures, it may be easier to manufacture, and it may be easier to handle during the assembly of the flow regulator 80, as compared to a less robust flexure 84.

A channel 86 and a flexure 98 having a large L/W ratio also allows the use of a channel 86 and a regulator gap 99 having a larger cross-sectional area, for any particular designed flow and regulation parameters, as compared to a channel 86 and a flexure 98 having a small L/W ratio. This is because as the channel 86 becomes longer, its fluid resistance ($R_s$) becomes greater. Thus, for any particular desired operating pressure, in order to obtain a particular desired flow rate (Q), the cross sectional area of the channel 86 and the regulator gap 99 will have to be made larger, as the channel 86 and the flexure 98 become longer, in order to compensate for the otherwise increased fluid resistance ($R_s$) of the elongated channel 86 and the regulator gap 99.

Such an elongated channel 86 and regulator gap 99, having a larger cross-sectional area for a particular desired operating pressure and flow rate, may be desirable because their larger cross-sectional area may be less likely to foul due to contaminants in the medication 12, due to corrosion of the channel 86, the regulator seat 90, and the flexure 98.

From the disclosures in this document, it is possible to selectively design a linear flow regulator 80 for any particular desired flow regulation characteristics or driving pressure difference (P). This may be done by selectively adjusting one or more of the pertinent parameters, such as: (a) the number, size, shape, length and location of the inlet port 88 and the outlet port 92; (b) the number, size, cross-sectional configuration, and length of the channel 86 and the regulator gap 99; and (c) the length, thickness, resiliency, elasticity and stiffness of the flexure 98.

MICROMACHINED LINEAR FLOW REGULATOR 80 HAVING A CONTOURED REGULATOR SEAT 90 (FIGS. 7–12): MANUFACTURE

The substrate 82 may be made from any suitable strong, durable material which is compatible with the medication 12, and in which the channel 86 and the outlet port 54 may be manufactured in any suitable way, such as by using any suitable etching, molding, stamping and machining process. Such a machining process may include the use of physical tools, such as a drill; the use of electromagnetic energy, such as a laser; and the use of a water jet.

The membrane 84 may be made from any suitable strong, durable, flexible, material which is compatible with the medication 12. The membrane 84 may also be elastic.

If the regulator 80 is intended to regulate a medication 12 which is to be supplied to a human or an animal, then any part of the regulator 80 which is exposed to the medication 12 should be made from, and assembled or bonded with, non-toxic materials. Alternatively, any toxic material which is used to manufacture the regulator 80, and which is exposed to the medication 12 during use of the regulator 80, may be provided with any suitable non-toxic coating which is compatible with the medication 12.

Suitable materials for the substrate 82 and the membrane 84 may be metals (such as titanium), glasses, ceramics, plastics, polymers (such as polyimides), elements (such as silicon), various chemical compounds (such as sapphire, and mica), and various composite materials.

The substrate 82 and the membrane 84 may be assembled together in any suitable leak-proof way. Alternatively, the substrate 82 and the membrane 84 may be bonded together in any suitable leak-proof way, such as by anodically bonding them together; such as by fusing them together (as by the use of heat or ultrasonic welding); and such as by using any suitable bonding materials, such as adhesive, glue, epoxy, glass solder, and metal solder.

Anodically bonding the substrate 82 to the membrane 84 may be preferable for at least four reasons. First, anodic bonding is relatively, quick, easy and inexpensive. Second, an anodic bond provides a stable, leak-proof bond. Third, since an anodic bond is an interfacial effect, there is no build-up of material at the bond; and the bond has essentially a zero thickness, which desirably creates no essentially no spacing between the substrate 82 and the membrane 84. As a result, an anodic bond does not interfere with the desired height or shape of the regulator gap 99.

Fourth, an anodic bond may be preferable since it eliminates the need for any separate bonding materials, which might otherwise clog or reduce the size of the inlet port 88, the channel 86, the regulator gap 99, and the outlet port 92; or which might lead to corrosion of the joint between the substrate 82 and the membrane 84.

One example of how the linear flow regulator 80 may be manufactured will now be given.

The starting point may be a 76.2 mm diameter wafer of Corning 7740 Pyrex glass, which will form the regulator 80's substrate 82.

The channel 86 and its regulator seat 90 may then be formed in the substrate 82 in any suitable way. One suitable way may be to first etch a generally rectangular channel into the substrate 82, wherein the rectangular channel has a length and a depth about equal to the length and the depth of the desired channel 86 and regulator seat 90. The rectangular channel may be etched into the substrate 82 in any suitable way, such as by using a process which is the same as, or at least similar to, that used to etch the radial flow regulator 32's inlet channels 38 into its substrate 34.

After the rectangular channel has been etched, the regulator 80's outlet port 92 may be formed. The structure, operation, theory and manufacture of the linear flow regulator 80's outlet port 92 is the same as, or at least similar to, that of the radial flow regulator 32's outlet port 54, except for those differences, if any, which will be made apparent by an examination of all of the Figures and disclosures in this document.

After the outlet port 92 has been formed, a nominal layer of one or more corrosion-resistant substances may be deposited onto the top surface of the glass wafer in any suitable way. As a result, the channel 86, the regulator seat 90, and the outlet port 92 will have been coated with a layer of the corrosion-resistant substance(s). The structure, operation, theory and manufacture of such a layer of one or more corrosion-resistant substances for the linear flow regulator 80 is the same as, or at least similar to, that of the radial flow regulator 32's layer of one or more corrosion-resistant substances, except for those differences, if any, which will be made apparent by an examination of all of the Figures and disclosures in this document.

After the channel 86 and the regulator seat 90 have been etched, and after any desired layer of corrosion-resistant substance(s) has been applied to etched portions of the glass wafer, the photoresist and chrome which remain on the unetched portions of the glass wafer may be removed by any suitable means, such as by using standard lift-off techniques.

At this point, certain work on the manufacture of the membrane 84 may be done before the desired channel 86 and regulator seat 90 may be completed. Manufacturing the membrane 84 and bonding it to the glass wafer (which is the substrate 82) may be done in any suitable way. The structure, operation, theory and manufacture of the linear flow regulator 80's membrane 84 and the bonding of the membrane 84 to its substrate 82 to form a silicon/glass sandwich is the same as, or at least similar to, the manufacture of the radial flow regulator 32's membrane 36, and the bonding of the membrane 36 to its substrate 34 to form a silicon/glass sandwich, except for those differences, which will be made apparent by an examination of all of the Figures and disclosures in this document.

Some of those differences will now be addressed. It may be recalled that the starting point for the regulator 80's membrane 84 may be a prime silicon wafer having a boron-doped epitaxial silicon layer which has been deposited onto one of its surfaces. Since the boron doped layer will ultimately form the regulator 80's membrane 84, the boron-doped layer's thickness will depend on the desired thickness of the membrane 84. The boron-doped layer has a dramatic etch-resistance to silicon etchants based on ethylene diamine; but is easily etched by isotropic etchants. The isotropic etchants will also easily etch the non-doped layer of the silicon wafer.

Accordingly, the first step in manufacturing the regulator 80's membrane 84 is to first clean the silicon wafer; apply a thin chrome metallization layer to both of the wafer's surfaces; and then apply and dry a thin layer of any suitable photoresist on top of the chrome layer.

An image of the inlet port 88 may then be exposed onto the photoresist on the silicon wafer's boron-doped layer, and then developed; after which the silicon wafer may be cleaned and dried.

As a result of the forgoing procedure, the chrome layer over the boron-doped layer will now bear an image, unprotected by the photoresist, of the inlet port 88. The unprotected portion of the chrome layer may then be etched away; resulting in an image of the inlet port 88 having been formed on the boron-doped layer, which image is unprotected by the layers of photoresist and chrome which cover the rest of the silicon wafer. The image of the inlet port 88 may then be etched into the boron-doped layer to a depth which is at least slightly greater than the thickness of boron-doped layer in any suitable way, such as by using an isotropic etchant. The photoresist and the chrome layers may then be removed from the silicon wafer, which may then be cleaned and dried.

The silicon and glass wafers may then be aligned, so that the etched image of the inlet port 88 in the boron-doped layer is in proper registry with the etched image of the channel 86 in the glass wafer. The etched surfaces of the silicon and glass wafers may then be anodically bonded together; after which the non-doped layer of the silicon wafer may then be etched and ground to produce the desired membrane 84, with the desired inlet port 88. The desired inlet port 88 is automatically formed during the etching and grinding of the non-doped layer of the silicon wafer because the isotropic etchant had previously completely etched away the image of the inlet port 88 in the boron-doped layer of the silicon wafer; so that when the non-doped layer of the silicon wafer is etched and ground away, the inlet port 88 is automatically formed.

The desired contour may be imparted to the channel 86's regulator seat 90 in any suitable way. One suitable way may be to use a pressure forming method, in which the substrate 82 may first be placed into a forming device which restrains the substrate 82's bottom surface 104 and its lateral edges. A flat stencil having a cutout whose length and width corresponds to that of the desired channel 86 may be provided; the membrane 84 may be tightly sandwiched between the stencil and the substrate 82; and at least the substrate 82 may be heated to an elevated process temperature at which the substrate 82 is softened. For example, the elevated process temperature for a Pyrex glass substrate may be about 600° C.

The portion of the membrane 84 which is exposed through the stencil (i.e., the flexure 98), may then exposed to a pressure about equal to the regulator 80's maximum designed driving pressure difference (P), thereby deflecting the flexure 98 down into the softened substrate 82 and forming the channel 86's contoured regulator seat 90. For example, for a Pyrex glass substrate which is heated to about 600° C., the pressure may be about 100 pounds per square inch (psi). The rectangular channel mentioned above, which was etched into the substrate 82, may aid in the formation of the desired contoured regulator seat 90 since all the deflected flexure 98 needs to do is to mold the rectangular channel's sides and bottom into the desired contour. The forming device for the substrate 82 may have a relief hole which permits the exit of any excess substrate 82 material which is displaced by the deflected membrane 84. Alternatively, the rectangular channel mentioned above may be dispensed with, and the flexure 98 may be deflected with pressure down into the softened substrate 82 to form the contoured regulator seat 90.

The desired pressure may then be maintained on the flexure 98 while the substrate 82 is cooled and hardened, thereby forming the substrate 82's channel 86 with the desired contour in its regulator seat 90. The pressure may then be released, allowing the elastic flexure 98 to return to its undeflected configuration. The stencil, the forming device and any undesired displaced substrate 82 material may then be removed.

Although the use of a heat softened substrate 82 was described above, the contoured regulator seat 90 may be pressure formed into the substrate 82 in any other suitable way. For example, the substrate 82 may be selected to be made from a material, such as an epoxy, a ceramic material or a solvent-softened material, which is soft at room temperature, and which is then hardened after the flexure 98 is deflected down into it by a chemical reaction, by the application of heat, or by the evaporation of the solvent, respectively.

Another way to form the contoured regulator seat 90 may be to micromachine the desired contour into the substrate 82 by use of a laser beam. Such a laser beam may be regulated, by any suitable means, to have an intensity gradient similar to that of the desired contour of the channel 86's regulator seat 90, such as by projecting the laser beam through one or more suitable lenses and/or gradient filters.

Another way of using a laser beam to micromachine the desired contour into the substrate 82 may be to project the laser beam through a mask to give at least a portion of the laser beam a cross-sectional configuration which is similar to that the desired contour of the regulator seat 90.

The manufacture of only one linear flow regulator 80 was described above. However, it will be appreciated that on any pair of glass and silicon wafers numerous regulators 80 could be manufactured simultaneously in a manner similar to that described above. If such is the case, an array of substrates 82 may be simultaneously etched in the glass wafer before the silicon and glass wafers are aligned and bonded together. Then, all of the membranes 36, and their inlet ports 88 may be formed simultaneously. The silicon/glass sandwich may then be divided by any suitable means (such as dicing) into individual chips, each chip bearing at least one linear flow regulator 80.

One of the advantages of using the etching, anodic bonding, and pressure forming process which was described in detail above is that such a process enables high quality, very reliable linear flow regulators 80 to be mass produced in great numbers at a cost so low that the regulator 80 may be considered to be disposable. In addition, it should also be noted that the regulator 80 is stunning in its simplicity since it may have as few as only two parts (the substrate 82 and the membrane 84); and since it may have only one moving part (the membrane 84's flexure 98). Further, the cost of the regulator 80 may held to a very low level because the raw materials from which the regulator 80 may be made may be very inexpensive, such as glass and silicon.

MICROMACHINED LINEAR FLOW REGULATOR 110 HAVING A NON-CONTOURED REGULATOR SEAT 90 (FIGS. 13–15): STRUCTURE

Figure 13:
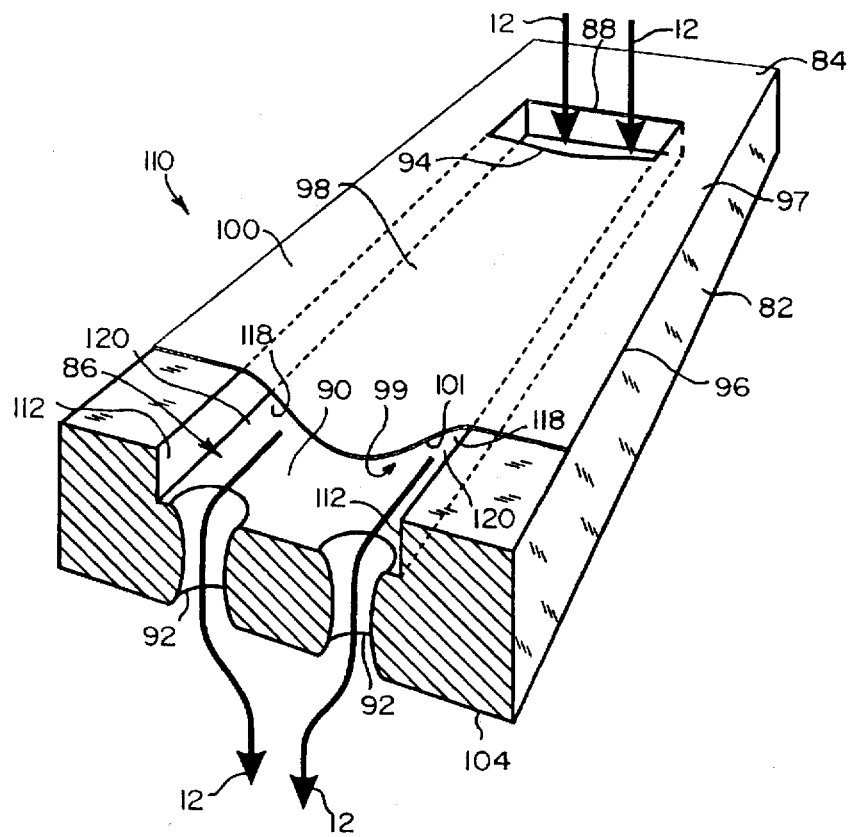
FIG. 13 is a perspective view, partly in a cross-section taken substantially along line 13—13 of FIG. 14, of a micromachined linear flow regulator of the present invention having a non-contoured regulator seat.
Figure 14:
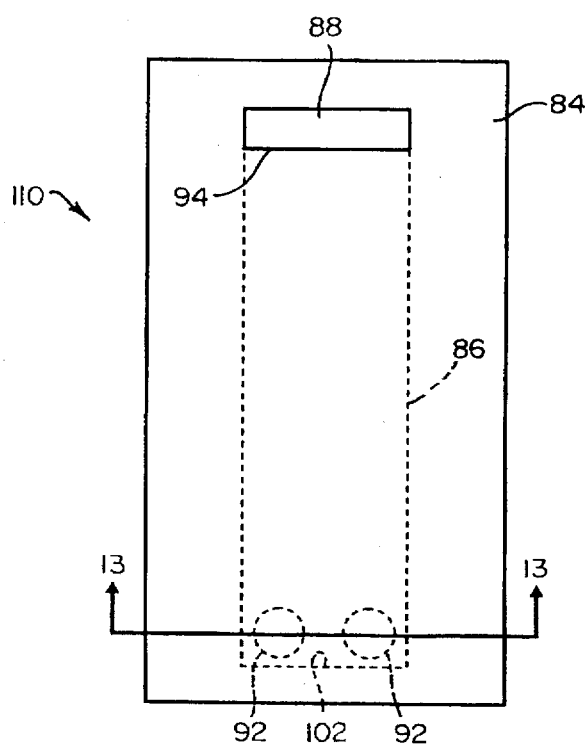
FIG. 14 is a top elevational view thereof.

The linear flow regulator 110 which is illustrated in FIGS. 13–14 is the same as, or at least similar to, the linear flow regulators 80 of FIGS. 7–11 in its structure, except for those differences, if any, which will be made apparent by an examination of all of the Figures and disclosures in this document.

Accordingly, the respective parts of the linear flow regulator 110 of FIGS. 13–14 has been given the same reference numerals as the corresponding parts of the linear flow regulators 80 of FIGS. 7–11, for clarity and simplicity.

As seen in FIGS. 13–14, the linear flow regulator 110 has a pair of outlet ports 92; and a channel 86 having a pair of sides 112 which are at right angles to the non-contoured regulator seat 90.

As used herein, the term "non-contoured" means that the regulator seat 90 does not approximate, or duplicate, the contoured shape that the flexure 98 would assume if the flexure 98 were entirely unrestrained by any part of the substrate 82 when the linear flow regulator 110 is subjected to the regulator 110's maximum designed driving pressure difference (P) of the medication 12 between the regulator 110's inlet port 88 and outlet port 92.

It should be understood that FIGS. 13–14 illustrate only one example of a non-contoured regulator seat 90, i.e., a flat non-contoured regulator seat 90. Naturally, the non-contoured regulator seat 90 could have any of a variety of other configurations, shapes, or forms.

Figure 15:
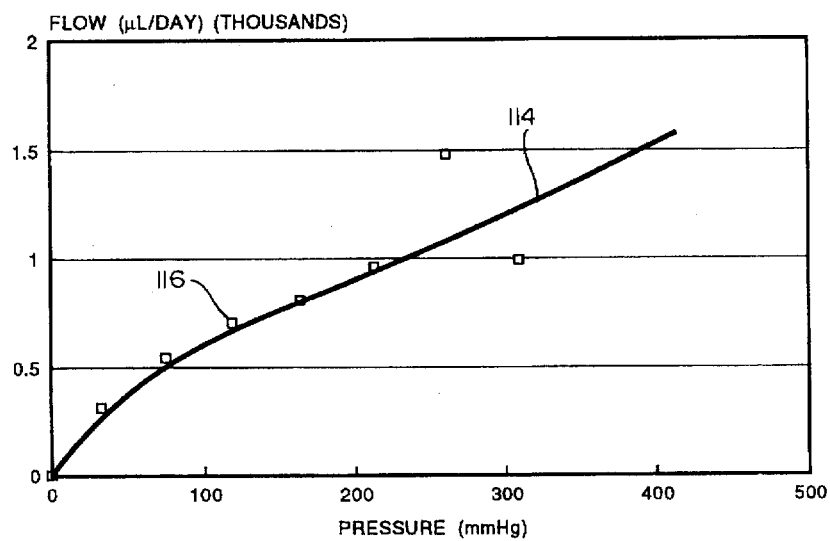
FIG. 15 is a is a graph depicting certain fluid flow characteristics thereof.

By way of example, the linear flow regulator 110's substrate 82 may be manufactured from 7740 Pyrex glass, and may have a thickness of about 0.5 mm. The channel 86 and the regulator seat 90 may have a length of about 1.0 cm, and may have a maximum width of about 508 microns. The regulator gap 99 may have a maximum height of about 4.2 microns (when the driving pressure difference (P) is equal to zero). Each outlet port 92 may have a minimum diameter of about 100 microns, and may have a length of about 496 microns. The membrane 84 may be manufactured from silicon, and may have a thickness of about 9.0 microns. The inlet port 88 may have a width of about 508 microns, and a length of about 500 microns. The flow characteristics of this example linear flow regulator 110 are illustrated in FIG. 15, which will be discussed below.

MICROMACHINED LINEAR FLOW REGULATOR 110 HAVING A NON-CONTOURED REGULATOR SEAT 90 (FIGS. 13-15): OPERATION AND THEORY

The linear flow regulator 110 which is illustrated in FIGS. 13-14 is the same as, or at least similar to, the linear flow regulators 80 of FIGS. 7-11 in its operation and theory, except for those differences, if any, which will be made apparent by an examination of all of the Figures and disclosures in this document.

During operation, as a driving pressure difference (P) is applied across the regulator 110, such as by pressurizing the source of the medication 12 with respect to the regulator 110's outlet port 92 by any suitable means, the medication 12 will pass sequentially through the regulator 110's inlet port 88, regulator gap 99, and outlet port 92.

Referring now to FIG. 15, the flow rate (Q) of the medication 12 through the regulator 110 is plotted in terms of microliters per day (µL/day), as a function of the driving pressure difference (P) across the regulator 110 in mm Hg. The regulator curve 114 is a plot of a theoretical mathematical model of the flow rate (Q) of the medication 12 for a regulator 110 having the physical parameters of the example regulator 110 which was set forth above. The theoretical mathematical model will be discussed below. The seven square data points 116 seen in FIG. 15 are for the measured flow rates (Q) of an actual flow regulator 110 having the physical parameters of the example regulator 110 which was set forth above. As seen, the theoretical model does quite well in predicting the performance of the flow regulator 110.

FIG. 15 reveals that, at a zero driving pressure difference (P), there is no flow of the medication 12 through the regulator 110. Then, as the driving pressure difference (P) is increased from zero, the regulator 110 exhibits two main flow regimes.

That is, as the driving pressure difference (P) is increased from zero, there is a corresponding increase of the flow rate (Q); but there is also a gradual lessening of the flow rate's (Q's) sensitivity to the driving pressure difference (P). For example, this is seen on the curve 114 at driving pressure differences (P) from about 0.0 mm Hg to about 120 mm Hg.

Then, at higher pressure differences (P), there is a "control zone" wherein the flow rate (Q) is relatively linear function of changes in the driving pressure difference (P), and the sensitivity of the regulator 110 to changes in the driving pressure difference (P) is reduced by about 45%, as compared to a device having no flow regulation properties at all.

This behavior of the flow regulator 110 during operation is due to the fact that, as the driving pressure difference (P) across the regulator 110 is increased, the flexure 98 tends to be deflected towards the regulator seat 90 an increased amount, thereby reducing the height of the regulator gap 99. This, in turn, tends to maintain the flow rate (Q) at a relatively constant value, despite the increased driving pressure difference (P). This is because the reduced height of the regulator gap 99 will tend to compensate for the increased driving pressure difference (P) by reducing the flow rate (Q) which would otherwise occur at that increased driving pressure difference (P).

On the other hand, if the driving pressure difference (P) decreases, then the flexure 98 will tend to be deflected towards the regulator seat 90 a decreased amount, thereby increasing the height of the regulator gap 99. This, in turn, tends to maintain the flow rate (Q) at a relatively constant value, despite the reduced driving pressure difference (P). This is because the increased height of the regulator gap 99 will tend to compensate for the reduced driving pressure difference (P) by increasing the flow rate (Q) which would otherwise occur at that reduced driving pressure difference (P).

However, as seen in FIG. 13, even when the driving pressure difference (P) has been increased to the point where the flexure 98 is deflected so much that it starts to contact the regulator seat 90, the medication 12 will still be permitted to flow through the two side channels 118 which are formed between the deflected flexure 98, the regulator seat 90's side portions 120, and the channel 98' side walls 112.

Lastly, as the driving pressure difference (P) is increased still further, the flexure 98 will be flattened against the regulator seat 90 an increased amount, thereby gradually decreasing the size of the side channels 118 (and vice versa).

In order to assist in designing the regulator 110 to have any particular desired regulator curve 114, either an empirical strategy or a mathematical model may have to be employed.

The starting point for the mathematical model is the mathematical model which was set forth above regarding the regulators 80. It will be recalled that the above equation 7 yielded a relation between the driving pressure difference (P) and the total flow rate (Q) of the medication 12 up to the point P=1, the dimensionless pressure at which the flexure 98 first contacts the regulator seat 90.

However, beyond that pressure the flexure 98 will spread laterally across the regulator seat 90; and the first point of contact between the flexure 98 and the regulator seat 90 will expand and move along the z axis towards the inlet port 88.

In this mode of operation, the dimensionless pressure (P) still cannot exceed 1.0 since the depth of the channel 86 is fixed. Instead, as has been mentioned, two parallel side channels 118 are formed, each having a size which is a function of the driving pressure difference (P). That is, as the driving pressure difference (P) increases, the size of the side channels 118 decreases, (and vice versa).

For a channel 86 having a length $Z_0$, the point of first contact between the flexure 98 and the regulator seat 90 is some fraction of that length, i.e., $n \cdot Z_0$. Since P=1 at each local fluid slice in the two side channels 118, the effective width of each of the side channels 118 is:

$$w_e = \frac{w}{P^{.25}}$$

where P>1.

From the above Equation 6, for the boundary condition P=1, the following differential equation for pressure drop can be obtained:

$$\frac{dP}{dz} = 21.57 \cdot \left( \frac{\mu w^3 Q_o}{E t^3 h^4} \cdot \frac{1}{n P^{.25}} \right)$$

where ($Q_0$) is the flow when the contact between the flexure 98 and the regulator seat 90 is at $z=Z_0$. That is, when P=1 is the above Equation 7. Upon separation of variables, and some algebraic manipulation, a surprisingly simple relationship for flow versus pressure is found in the mode where there is contact between the flexure 98 and the regulator seat 90:

$$Q = Q_0[1 + 0.4271(P^{1.25} - 1)]$$

where P>1.

The above model may now be used to predict the performance of the linear flow regulator 110.

From the disclosures in this document, it is possible to selectively design a linear flow regulator 110 for any particular desired flow regulation characteristics or driving pressure difference (P). This may be done by selectively adjusting one or more of the pertinent parameters, such as: (a) the number, size, shape, length and location of the inlet port 88 and the outlet port 92; (b) the number, size, cross-sectional configuration, and length of the channel 86 and the regulator gap 99; (c) the length and shape of the regulator seat 90; (d) the length and shape of the side channels 118; and (e) the length, thickness, resiliency, elasticity and stiffness of the flexure 98.

MICROMACHINED LINEAR FLOW REGULATOR 110 HAVING A NON-CONTOURED REGULATOR SEAT 90 (FIGS. 13–15): MANUFACTURE

The manufacture of the linear flow regulator 110 of FIGS. 13–14 may be the same as, or at least similar to, the linear flow regulators 80 of FIGS. 7–11, except for those differences, if any, which will be made apparent by an examination of all of the Figures and disclosures in this document.

Since the regulator 110 has a non-contoured regulator seat 90, the steps relating to pressure forming the regulator 80's contoured regulator seat 90 may be eliminated. Instead, the rectangular channel is etched into the substrate 82 so that the rectangular channel has a length, width and depth which are equal to that of the desired channel 86. In other words, the etched rectangular channel becomes the desired channel 86, and the etched rectangular channel's bottom forms the non-contoured regulator seat 90; with no further work being needed in order to form the desired channel 86 and the non-contoured regulator seat 90.

Another way to form the channel 86 and the non-contoured regulator seat 90 may be to use a laser beam or a water jet.

MICROMACHINED DIAPHRAGM PUMP 130 HAVING INTEGRAL VALVING AND A CENTRALLY LOCATED INLET PORT (FIGS. 16–17): STRUCTURE

Figure 16:
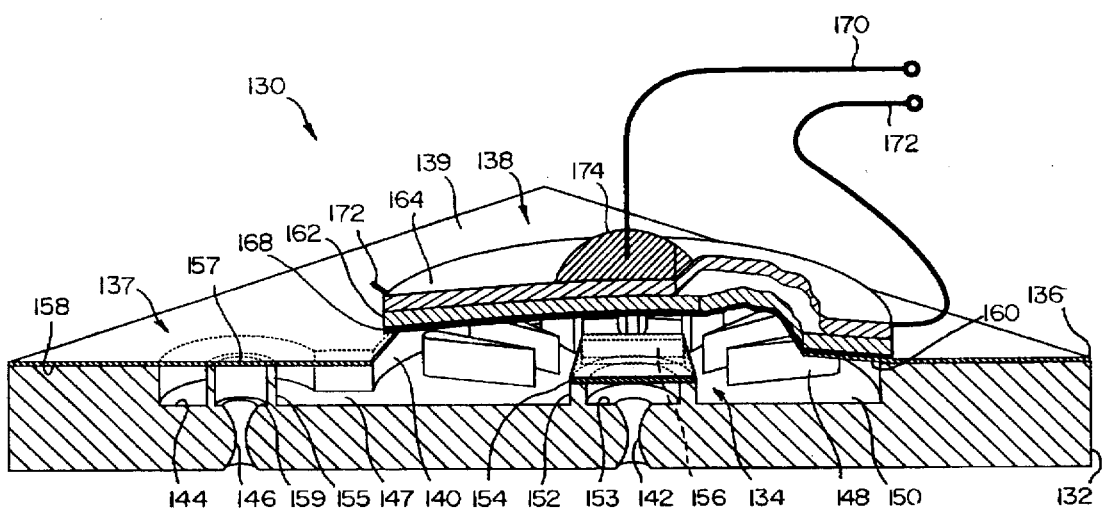
FIG. 16 is a perspective view, partly in a cross-section taken substantially along line 16—16 of FIG. 17, with certain parts broken away, of a micromachined diaphragm pump of the present invention having integral valving and a centrally located inlet port.
Figure 17:
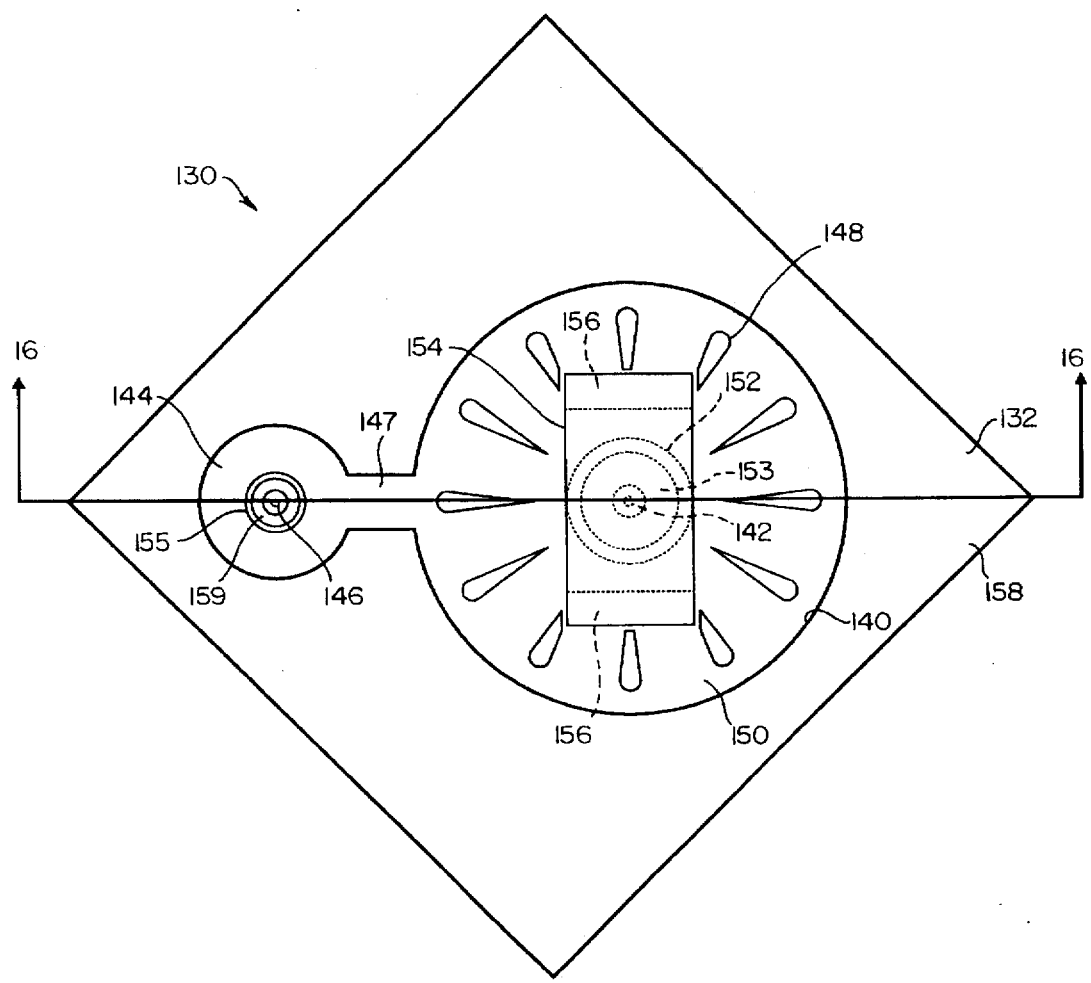
FIG. 17 is a top elevational view of the entire substrate thereof.

The first embodiment of the micromachined diaphragm pump 130 for the medication 12 is illustrated in FIGS. 16–17. The pump 130 may have five basic structures, namely a substrate 132; a one-way inlet valve 134; a membrane 136; a one-way outlet valve 137; and a piezoelectric motor 138.

The substrate 132 may have a circular pumping cavity 140 with an inlet port 142; a circular outlet valve cavity 144 with an outlet port 146; and a channel 147 which connects the pumping cavity 140 and the outlet valve cavity 144. Although the cavities 140, 144 are illustrated as being circular, they may have any other suitable size and shape. Although only one, rectangular channel 147 is illustrated, there may be more channels 147, and each channel 147 may have any other suitable size and shape. Although the inlet and outlet ports 142, 146 are illustrated as having a venturi-like shape for better fluid flow therethrough, they may have any other suitable size and shape.

The membrane 136 may have a mounting portion 139, which may be mounted to a respective portion of the substrate 132's top surface 158; an outlet valve flexure 157, which overlies the outlet cavity 144; and a pumping flexure 160, which overlies the pumping cavity 140.

Figure 18:
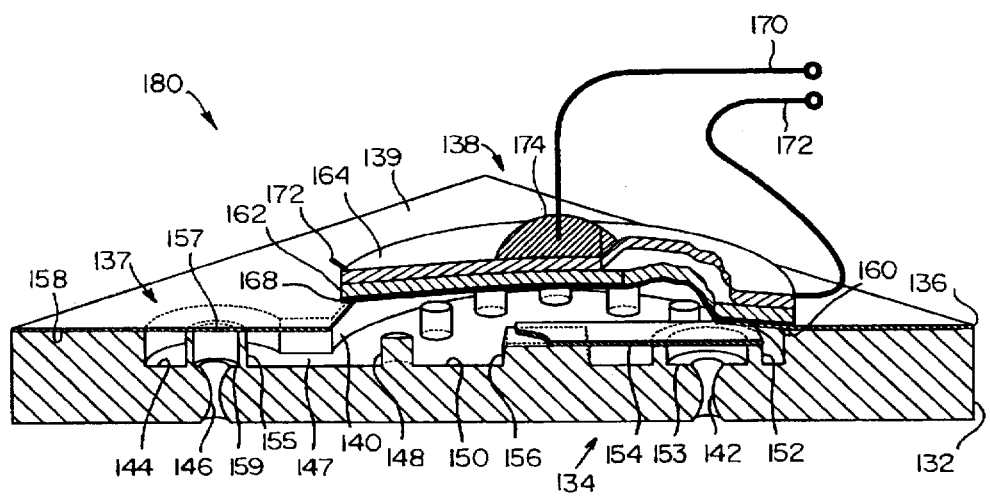
FIG. 18 is a perspective view, partly in a cross-section taken substantially along line 18—18 of FIG. 19, with certain parts broken away, of a micromachined diaphragm pump of the present invention having integral valving and an edge located inlet port.
Figure 19:
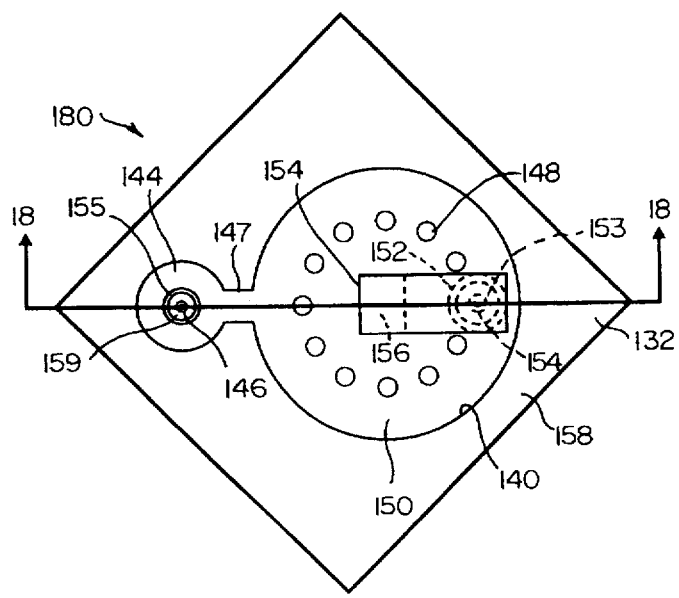
FIG. 19 is a top elevational view of the entire substrate thereof.

Within the pumping cavity 140 may be twelve flexure supports 148; which may prevent the pumping flexure 160 from being broken in the event the pumping flexure 160 is inadvertently forced downwardly towards the pumping cavity 140's bottom 150. The flexure supports 148 may also serve to prevent the pumping flexure 160 from being deflected downwardly more than a predetermined amount by the motor 138 during operation of the pump 130. Although the twelve flexure supports 148 are illustrated as being in the form of radial spines in FIGS. 16–17, there may be fewer or more flexure supports 148, and each flexure support 148 may have any other suitable size and shape, such as the cylindrical pin shaped flexure supports 148 which are illustrated in FIGS. 18–19.

It has been discovered that using relatively small cylindrical pin shaped flexure supports 148 (FIGS. 18–19), instead of relatively large radial spine type flexure supports 148 (FIGS. 16–17), may be advantageous for at least four reasons. First, they may have less flow resistance to the medication 12 being pumped by the pump 130. Second, they may have less adverse impact on the priming of the pumping cavity 140. Third, they may have less propensity to undesirably trap bubbles within the pumping cavity 140. Fourth, they may have less of an adverse impact on the ability of the medication 12 to sweep any bubbles out of the pumping cavity 140 during operation of the pump 130.

The one-way inlet valve 134 may comprise a circular inlet valve seat 152; an inlet cavity 153; an inlet valve flexure 154; and a pair of bosses 156, to which the ends of the inlet valve flexure 154 may be bonded. The tops of the inlet valve seat 152 and the bosses 156 may be flat and coplanar, so that the inlet valve flexure 154 may lay flat across the top of the inlet valve seat 152, as seen in FIG. 16, when no medication 12 is entering the pumping cavity 140 through its inlet port 142. The inlet cavity 153 may be used to define a clean outer perimeter for the inlet port 142, particularly if the inlet port 142 is drilled with a laser. However, the inlet cavity 153 may be eliminated, and the inlet port 142 may be extended upwardly so that it communicates directly with the inlet valve seat 154's top surface. Alternatively, the inlet port 142 may be eliminated, and the inlet cavity 153 may be extended downwardly so that it communicates directly with the substrate 132's bottom surface.

The one-way outlet valve 137 may comprise a circular outlet valve seat 155; an outlet cavity 159; and the outlet valve flexure 157. The top of the outlet valve seat 155 and the substrate 132's top surface 158 may be flat and coplanar, so that the outlet valve flexure 157 lies flat across the top of the outlet valve seat 152, as seen in FIG. 16, when no medication 12 is exiting the outlet valve cavity 144 through its outlet port 146. The outlet cavity 159 may be used to define a clean outer perimeter for the outlet port 146, particularly if the outlet port 146 is drilled with a laser. However, the outlet cavity 159 may be eliminated, and the outlet port 146 may be extended upwardly so that it communicates directly with the outlet valve seat 155's top surface. Alternatively, the outlet port 146 may be eliminated, and the outlet cavity 159 may be extended downwardly so that it communicates directly with the substrate 132's bottom surface.

From the foregoing, it is seen that the membrane 136 may serve triple functions; namely, its pumping flexure 160 may serve as the diaphragm for the pumping cavity 140; its outlet valve flexure 157 may serve as the diaphragm for the outlet valve 137; and its mounting portion 139 may seal the membrane 136 to the substrate 132's top surface 158, to prevent leakage from the pumping cavity 140, the outlet valve cavity 144, and the channel 147.

Although the inlet and outlet valve seats 152, 155 are illustrated as being circular, they each may have any other suitable size and shape. Although one particular form of one-way inlet and outlet valves 134, 137 are illustrated in FIGS. 16–17, the pump 130's one-way inlet and outlet valves 134, 137 may be any other suitable one-way valve, such as the one-way valves which are disclosed in this document.

The piezoelectric motor 138 may comprise a sandwich formed by bonding together a piezoelectric disk 162 and a conductive cover disk 164. The sandwich may then, in turn, be bonded to the pumping flexure 160.

Alternatively, the cover disk 164 may be eliminated, and the piezoelectric disk 162 may be firmly bonded to the pumping flexure 160's top surface in any suitable way, such as by using a layer 168 of a hard bonding material, such as an epoxy. In such an event, the pumping flexure 160 would assume the role served by the cover disk 164. However, such a construction is not preferred since such a layer 168 of hard bonding material between the piezoelectric disk 162 and the pumping flexure 160 may lead to undesirable distortions of the pumping flexure 160 over the operating temperature range; and may lead to limiting the displacement of the pumping flexure 160 (for any given power input), due to radial shear between the piezoelectric disk 162 and the pumping flexure 136.

Any suitable source of electrical power may be supplied to the piezoelectric motor 138 through a pair of wires 170, 172. The wire 170 may be electrically connected to the motor 138's cover disk 164 in any suitable way, and the wire 172 may be electrically connected to the bottom of the piezoelectric disk 162 in any suitable way.

By way of example, the diaphragm pump 130 may have a weight of about 0.6 grams; and may have the following physical parameters. The substrate 132 may be a square having sides about 1.30 cm long, and a thickness of about 0.5 mm. The membrane 136 may have a thickness of about 25 microns. The inlet valve flexure may have a thickness of about 9 microns, a width of about 1940 microns, and a length of about 2900 microns. The pumping cavity 140 may have a diameter of about 1.07 cm, and the outlet valve cavity 144 may have a diameter of about 3.4 mm. The cavities 140, 144 and the channel 147 may each have a depth of about 25 microns. The channel 147 may have a width of about 0.5 mm, and a length of about 1.0 mm. The inlet and outlet ports may have a minimum diameter of about 50–100 microns. The flexure supports 148 and the outlet valve seat 154 may have a height of about 25 microns. The inlet valve seat 152 and the inlet valve flexure bosses 156 may have a height of about 9 microns. The piezoelectric motor 138 may act as about a 0.02 μF capacitor; and its disks 162, 164 may have a thickness of about 0.15 mm, and a diameter of about 1.1 cm. The bonding material 168, which bonds the disk 162 to the pumping flexure 160's top surface may have a thickness of about 50 microns; and the wires 170, 172 may have a diameter of about 50 microns. This example pump 130 may deliver about 0.1 to 1.0 microliters of the medication 12 per pumping cycle; and operate at a frequency of from about 0.0 to about 25.0 pumping cycles per second.

Naturally, any of the forgoing physical parameters of the diaphragm pump 130 may be varied, in order to provide a pump 130 having the particular size, pumping and operating characteristics which may be desired.

As will be appreciated from all of the disclosures in this document, since the pump 130 may have an extremely small size, an extremely low weight, a very small number of parts, and a very small electrical energy consumption, the pump 130 has numerous advantages over a pump 130 which is physically much larger, much heavier, more complex, or a much larger consumer of electrical energy. For example, the pump 130 of the present invention may be ideal for use as part of a miniaturized medication delivery device which is to be implanted in a human or animal for delivery of flow rates of the medication 12 as low as about 0.05 microliters per pumping cycle—flow rates which are so low that they may be impossible for a physically larger pump of a different design to reliably and accurately deliver.

MICROMACHINED DIAPHRAGM PUMP 130 HAVING INTEGRAL VALVING AND A CENTRALLY LOCATED INLET PORT (FIGS. 16–17): OPERATION AND THEORY

The diaphragm pump 130 may be installed in its intended location of use in any suitable way. Any suitable medication supply means may be used to connect the pump 130's inlet port 142 to a source of the medication 12; and any suitable medication delivery means may be used to connect the pump 130's outlet port 146 to whatever person, animal or thing is to receive the medication 12 from the outlet port 146.

During operation, when any suitable source of electrical power is applied to the piezoelectric motor 138's wires 170, 172 (such as 100 volts D.C., with the voltage being applied to the wires 170, 172 in the same polarity as the original ferroelectric polarization of the piezoelectric disk 162), the piezoelectric disk 162 may tend to contract radially. The amount of such contraction is a function of the voltage applied to the wires 170, 172, with the piezoelectric disk 162 tending to contract more as the voltage is increased (and vice versa).

However, since the radial contraction of the disk 162's top surface is restricted by its bonded cover disk 164, the piezoelectric motor 138 tends to assume a cupped shape, with the motor 138's center being raised up above the substrate 132's top surface 158 by about 25 microns, as seen in FIG. 16. In turn, since the motor 138 is bonded to the pumping flexure 160's top surface, this cupping action of the motor 138 causes the pumping flexure 160 to also tend to assume a cupped shape, with the center of the pumping flexure 160 also being raised up above the substrate 132's top surface 158 by about 25 microns, as is further seen in FIG. 16.

It has been discovered that selecting the diameter of the motor 138 to be at least slightly larger than the diameter of the pumping cavity 140 and the pumping flexure 160 may be preferable for at least two reasons. First, if the motor 138 is larger than the pumping flexure 160, then the motor 138 may protect the entire pumping flexure 160 from physical damage. Second, if the motor 138 is larger than the pumping cavity 140, then the peripheral edge of the motor 138 may rest on a portion of the membrane 136 which is directly supported by the substrate 132. Thus, when electrical power is applied to the motor 138's wires 170, 172, the peripheral edge of the motor 138 may act as a circular, circumferential fulcrum as the motor 138 assumes its cupped shape. However, the motor 138 may have a diameter which is less than the diameter of the pumping cavity 140 and the pumping flexure 160.

When the motor 138 and the pumping flexure 160 assume their above cupped shapes, the pressure of the medication 12 within the pumping cavity 140, channel 147 and outlet valve cavity 144 is reduced. The negative pressure does two things simultaneously. First, the negative pressure causes the inlet valve flexure 154 to bow upwardly; thereby unseating the inlet valve flexure 154 from the inlet valve seat 152, and drawing the medication 12 into the pumping cavity 140. Second, the negative pressure causes the outlet valve flexure 157 to be pulled downwardly; thereby seating the outlet valve flexure 157 against the outlet valve seat 155, and preventing any medication 12 in the pump 130's outlet port 146 from flowing into the outlet valve cavity 144.

On the other hand, if the source of electrical power to the motor 138's wires 170, 172 is reduced, or interrupted, the piezoelectric disk 162 will reduce, or cease, its radial contraction, since the amount of the radial contraction of the disk 162 is a function of the voltage applied to the wires 170, 172. As a result, the piezoelectric motor 138 and the pumping flexure 160 will automatically tend to return to their original, flat configurations, due to their resiliency and elasticity. As this happens, pressure of the medication 12 within the pumping cavity 140, the channel 147 and the outlet valve cavity 144 is increased.

This increase in the pressure of the medication 12 does two things. First, it forces the inlet valve flexure 154 downwardly; thereby seating the flexure 154 against the inlet valve seat 152, and preventing the medication 12 from flowing back out of the inlet port 142. Second, this increase in the pressure of the medication 12 causes the outlet valve flexure 157 to bow upwardly; thereby unseating the outlet valve flexure 157 from the outlet port's valve seat 152, and permitting the medication 12 to flow out of the pump 130's outlet port 146.

For the example pump 130, whose physical parameters were set forth above, the forgoing complete pumping cycle of the pump 130 corresponds to an output of from about 0.1 to about 1.0 microliters of medication 12 from the pump 130's outlet port 146.

From the forgoing, it will now be appreciated that the output of the medication 12 from the pump 130 for each of its pumping cycles may be selectively varied by controlling the input voltage which is applied to the motor 138's wires 170, 172. That is, within certain limits, which may be determined by the sizing of the pump 130 and the materials used in the pump 130, the amount of the displacement of the pumping flexure 160 is a function of the amount of the input voltage. In other words, as the input voltage is increased, the displacement of the membrane 138's pumping flexure 160 also increases, thereby increasing the output of the medication 12 from the pump 130 for each of its pumping cycles (and vice versa).

The total output from the pump 130 is governed by the displacement of the pumping flexure 160 during each of the pump 130's pumping cycles; and by the frequency of the input voltage to the motor 138's input wires 170, 172 which, in turn, governs the frequency at which the pump 130 is cycled. In other words, one complete cycle of the input voltage will result in one complete pumping cycle of the pump 130. For example, the example pump 130, whose physical parameters were set forth above, may be cycled as rapidly as about 25 times per second, although its efficiency may peak at lower cycle rates, such as about once per second. If the example pump 130 is cycled once per second, its total output of the medication 12 from its outlet port 146 will be about 6.0 to about 60.0 microliters of medication 12 per minute, or about 8.64 to about 86.4 cc per day.

Alternatively, instead of merely reducing or interrupting the electrical power to the motor 138's wires 170, 172 during the pump 130's above pumping cycle, the polarity of the voltage applied to the wires may be reversed during the pump 130's above pumping cycle. During such bipolar operation of the pump 130, instead of the centers of the motor 138 and the pumping flexure 160 merely tending to automatically return to their original, flat configurations, they would also tend to be driven to be bowed or cupped downwardly towards the pumping chamber 140's bottom 150.

Thus, the direction of the displacement of the membrane 138's pumping flexure 160 will be a function of the polarity of the input voltage, while the amount of such displacement will be a function of the amount of the input voltage.

From the forgoing, it will now be appreciated that if the motor 138 is supplied with a D.C. voltage whose polarity is periodically reversed, and if the height of the flexure supports 148, the height of the inlet valve 134, and the depth of the pumping cavity 140 are appropriately selected, then the flexure 160 may be displaced or cupped away from the pumping chamber 140's bottom 150 during part of each pumping cycle, and may be displaced or cupped towards the pumping chamber 140's bottom 150 during the rest of each pumping cycle. As a result of such bipolar operation of the pump 130, the displacement of the pumping flexure 160 may be effectively doubled during each of the pump 130's pumping cycles (as compared to if the polarity of the input voltage was not periodically reversed), thereby doubling the pump 130's output of medication 12. The output pressure of the medication 12 from the pump 130 may also be increased by using bipolar operation of the pump 130.

If the pump 130 is operated so that the pumping flexure 160 is displaced downwardly towards the pumping chamber 140's bottom 150, the diameter of the motor 138 may be selected to be less than the diameter of the pumping chamber 140, to better enable such downward displacement to occur.

Generally, the above described bipolar operation of the pump 130 may be limited by depolarization of the piezoelectric disk 162 when it is reverse biased. Many ceramic materials substantially degrade in performance if operated for short periods of time at reversed polarity electric fields in excess of about 50 KV/cm. Hence, the above-described doubling effect of bipolar operation of the pump 130 may be substantially compromised by this limitation. Mono-polar operation of the pump 130 at high voltages and electric fields may be capable of achieving flows and pressure outputs which are comparable to those of such bipolar operation at lower voltages and electric fields.

The pump 130 may be driven by any suitable electrical driving means which may be attached to the motor 138's wires 170, 172. Such an electrical driving means may include a means for controlling the displacement of the pumping flexure 160 during each pumping cycle of the pump 130, (such as by suitably varying the polarity and/or the amount of the voltage applied to the motor 138's wires 170, 172); and/or may include means for varying the frequency of the pumping cycles of the pump 130, (such as by suitably varying the frequency of the voltage applied to the motor 138's wires 170, 172). Such electrical driving means may also include a suitably programmed microprocessor for helping the electrical driving means to perform its above functions.

It has been discovered that another important feature of the pump 130 is that the pump 130 may be made so that its piezoelectric motor 138 and its pumping flexure 160 may minimize, or even eliminate, undesirable forward flow of the medication 12 into the pumping cavity 140 through the inlet valve 134, in the event the medication 12 at the inlet port 142 is overpressurized beyond the nominal designed input pressure. Such forward flow of the medication 12 is undesirable since in many applications for the pump 130 there may be adverse consequences if that happens. For example, if the pump 130 were used in a medical device for delivering the medication 12 to a patient, such undesirable forward flow of the medication 12 might result in the possibility of injury or death to the patient due to an overdose of the medication 12.

There are several ways in which the pump 130 may be made so that its piezoelectric motor 138 and its pumping flexure 160 may minimize, or even eliminate, such undesirable forward flow of the medication 12 in the event of such overpressurization. For example, the various parts of the pump 130 may be sized so that, when there is no voltage applied to the pump 130's wires 170, 172, the bottom surface of the pumping flexure 160 will be in physical contact with the top surface of the inlet valve 134's flexure 154. Alternatively, the pumping flexure 160's bottom surface may be provided with a raised boss (not illustrated) which will be in contact with the top surface of the inlet valve 134's flexure 154 when there is no voltage applied to the pump 130. Thus, either the pumping flexure 160's bottom surface, or its raised boss, will rest on, and provide an interference fit with, the inlet valve flexure 154 when there is no voltage applied to the pump 130. (Such an interference fit may also assist in holding the inlet valve flexure 154 closed, to help prevent back flow of the medication 12 through the pump 130, in the event the pump 130 is subjected to a reverse pressure.)

Accordingly, before there is any undesired forward flow of the medication 12 into the pumping cavity 140 caused by such overpressurization of the medication 12, the force generated by that overpressurization on the bottom surface of the flexure 154 would have to overcome at least three things. First, it may have to lift the weight of the pumping flexure 160 and the motor 138. Second, it would have to overcome the stiffness of both the pumping flexure 160 and the motor 138, which may be much stiffer than the inlet valve flexure 154. Third, it would have to overcome the effect of any pre-load of the pumping flexure 160's bottom surface, or its raised boss (if any), on the inlet valve flexure 154. Accordingly, these three factors may result in the pump 130 having a significantly lower forward bleed rate of the medication 12 into the pumping cavity 140 in the event of such overpressurization, than would be the case if the pumping flexure 160 (or its raised boss) was not resting on the top surface of the inlet valve 134's flexure 154 when there is no voltage applied to the pump 130.

In addition, it has also been discovered that the undesired forward bleeding of the medication 12 into the pumping cavity 140 in the event of such overpressurization of the medication 12 (and the undesired back flow of the medication 12 into the pumping cavity 140, in the event the pump 130 is subjected to a reverse pressure), may also be reduced, or even eliminated, by reversing the polarity of the voltage which is applied to the motor 138's wires 170, 172. Such reversed polarity would cause the motor 138, and the pumping flexure 160, to assume a cupped shape, with the center of the pumping flexure 160 (or its raised boss), being pushed down against the inlet valve 134's flexure 154; thereby tending to hold the flexure 154 (or its raised boss) seated tightly against the inlet valve 134's valve seat 152, despite any such overpressurization of the medication 12, and despite any such reverse pressure of the medication 12.

It has also been discovered that, since the motor 138 acts as a capacitor with very low leakage, and can maintain a cupped shape under such reversed polarity with little additional electrical power input, the pump 130 is very efficient compared to a pump which utilized electromagnetic or thermal effects, where substantial electrical power would have to be input at all times in order to maintain such a cupped shape. In addition, the charge on the capacitor (the motor 138), may in part be recovered when the capacitor is discharged (when the input voltage is reduced or interrupted), to produce an output stroke, thereby further increasing the electrical energy efficiency of the pump 130.

Such electrical energy efficiency may be extremely important, such as if the pump 130 is used in a battery powered, implanted medical device. This is because any given battery will need to be recharged or replaced (which might require surgery), much less frequently, as compared to a pump 130 which was not so electrical energy efficient.

An important consideration in the design of the pump 130 may be the selection of the particular bonding material 168 which is used to bond the motor 138 to the pumping flexure 160. It has been discovered that this may be important for at least two reasons.

First, it has been discovered that if a hard bonding material 168, such as an epoxy, is used, and if the pump 130 is exposed to a wide operating temperature range (such as from about −40° C. to about 80° C.), then the pump 130 may experience operating difficulties. Such operating difficulties may include changes in the fit-up between the motor 138's piezoelectric disk 162 and the pumping flexure 160; closure problems with the inlet valve 134, due to static deflection of the pumping flexure 160; and changes in the volume of the medication 12 which is delivered by the pump 130 during each of its pumping cycles. This may be because the thermal expansion characteristics of the materials from which the piezoelectric disk 162 and the pumping flexure 160 are made generally differ significantly from each other, giving rise to interfacial shear between the disk 162 and the pumping flexure 160.

In addition, it has also been discovered that if the bonding material 168 is selected to be a hard bonding material 168 (such as an epoxy), then the motor 138's center will only deflect about 15% of the deflection the motor 138's center would experience if the motor 138 were free-standing by itself. This may be because a hard bonding material 168 may not be able to provide a low-shear joint between the piezoelectric disk 162 and the pumping flexure 160. Thus, most of the electrical energy which is delivered to such a hard-bonded piezoelectric disk 162 may be wasted in a futile attempt by the piezoelectric disk 162 to radially compress the relatively stiff pumping flexure 160.

On the other hand, it has been further discovered that if the bonding material 168, which is used to bond the motor 138 to the pumping flexure 160, is selected to be a soft, gel-like polymer, such as silicone rubber, then all of the above operating difficulties may be reduced, or even eliminated.

In addition, it has also been discovered that if a soft bonding material 168 is used, then the deflection of the motor 138's center will be increased up to about 85% of the deflection the motor 138's center would experience if the motor were free-standing by itself. That results in a remarkable gain of up to about 5 times in the length of the motor 138's useful pump stroke (as compared to when a hard bonding material 168 is used), with a corresponding remarkable reduction in the amount of electrical energy which is wasted by the pump 130. Thus, if a soft bonding material 168 is used, the pump 130's motor 138 utilizes its input energy unusually efficiently to cause maximum deflection of the pumping flexure 160. This, is turn, causes the pump 130 to deliver the maximum amount of medication 12 to its outlet port 146 for any given amount of input electrical energy. As has been mentioned, this energy efficiency may be extremely important, such as if the pump 130 is used in a battery powered, implanted medical device. This is because any given battery will need to be recharged or replaced (which might require surgery), much less frequently, as compared to a pump 130 which was not so energy efficient.

It is theorized that a soft, gel-like bonding material 168 may work so well because although it may have the ability to transmit vertical motion between the piezoelectric disk 162 and the pumping flexure 160, it may have very little ability to transmit shear forces between those two elements of the pump 130. Thus, the use of a soft, gel-like polymer as the bonding material 168 may relieve the stresses in the interface between the motor 138's piezoelectric disk 162 and the pumping flexure 160. This may reduce the shear loads between the disk 162 and pumping flexure 160, thereby permitting better coupling therebetween. Reducing such shear loads and increasing such coupling may be desirable because it may enable the pump 130 to operate at unusually low driving voltages (as low as about 50.0 volts; because it may reduce the energy consumption of the pump 130; and because it may enable the pump 130 to be made extremely small.

In addition, it has been discovered that the pump 130 is very efficient when operated at comparatively low average flow rates, such as about 1.0 microliters/second, and when the pump 130 is operated at comparatively low average operating pressures, such as about 1.0 to about 200 mm Hg. This is because at such low flow rates and operating pressures the flow of the medication 12 through the pump 130 tends to be laminar; meaning that less energy is lost due to friction, turbulence, and geometric shape changes of the medication 12.

For example, the example pump 130, whose physical parameters were set forth above, uses about 1/100th of the energy, and occupies about 1/50th of the space as compared to a peristaltic pump of equal capacity which is now used in an existing drug delivery device.

It has also been discovered that another important consideration in the design of the pump 130 may be to maintain a pre-determined residual amount of medication 12 in the pumping cavity 140 at all times during the pump 130's pumping cycle. For example, for a pump 130 having a very shallow pumping cavity 140 and a very small deflection or cupping of the motor 138 and the pumping flexure 160 (such as the example pump 130 whose physical parameters were set forth above), the pump 130 may be designed so that from about 10% to about 75% of the volume of the medication 12 in the pumping cavity 140, and preferably about 50% of the volume of the medication 12 in the pumping cavity 140, is left in the pumping cavity 140 during each pumping cycle.

It has been discovered that maintenance of such a residual amount of the medication 12 in the pumping cavity 140 at all times during the pump 130's pumping cycle may be important for at least two reasons. First, the pump 130 may be operated at a higher pumping cycle rate (frequency), than would otherwise be the case. This is because it can be shown that the time it would take for the pumping flexure 160 to completely pump all of the medication 12 out of the pumping cavity 140 (assuming there were no flexure supports 148 and inlet valve 134), becomes infinite as the pumping flexure 160 approaches the bottom of the pumping cavity 140. In such a case, the pumping flexure 160 would be attempting to remove the residual medication 12 in the pumping cavity 140 in the presence of a high-shear condition created by the extreme proximity of the pumping flexure 160 to the pumping cavity 140's bottom 150. This would result in an increased viscous drag which, in turn, would create a decreased efficiency and a need to operate the pump 130 at a lower pumping cycle rate, thereby undesirably limiting the dynamic range of the pump 130.

The second reason that it may be important to maintain a residual amount of the medication 12 in the pumping cavity 140 at all times is that the residual medication 12 in the pumping cavity 140 may provide a low resistance path for the medication 12 as it enters or leaves the pumping cavity 140. This is because of the fluid viscosity of the medication 12; because of the extremely small dimensions of the pumping cavity 140; and because of the extremely small dimensions of the components housed within the pumping cavity 140.

Maintenance of the desired residual amount of the medication 12 in the pumping cavity 140 at all times during the pump 130's pumping cycle may be achieved in any suitable way, such as by suitably selecting the depth of the pumping cavity 140; and by suitably controlling the depth to which the pumping flexure 160 may enter the pumping cavity 140, such as by suitably selecting the height and/or location of the flexure supports 148 and the inlet valve 134.

From the disclosures herein, it is seen that it is possible to selectively design a pump 130 having any particular desired medication 12 flow rate and output pressure. This may be done by selectively adjusting one or more of the pertinent parameters, such as: (a) the frequency of the input voltage (i.e., the pumping cycle rate of the pump 130); (b) the polarity and amount of the input voltage (i.e., the amount of medication 12 delivered by the pump 138 during each of its pumping cycles); (c) the power of the motor 138, and the number, size and shape of its piezoelectric and cover disks 162, 164; (d) the properties, size, shape and thickness of the bonding material 168; (e) the number, size, shape, and location of the inlet and outlet ports 142, 146, the inlet and outlet cavities 153, 159, the inlet and outlet valve seats 152, 155, the pumping flexure supports 148, the pumping cavity 140, the channel 147, and the outlet valve cavity 144; and the size, shape, location, thickness, resiliency, elasticity, and stiffness of the inlet valve flexure 154, the pumping flexure 160, and the outlet valve flexure 157.

MICROMACHINED DIAPHRAGM PUMP 130 HAVING INTEGRAL VALVING AND A CENTRALLY LOCATED INLET PORT (FIGS. 16-17): MANUFACTURE

The pump 130's substrate 132 may be made from any suitable strong, durable material, which is compatible with the medication 12, and in which the inlet port, the inlet cavity 153, the inlet valve seat 154, the pumping cavity 140, the flexure supports 148, the flexure support bosses 156, the channel 147, the outlet valve cavity 144, the outlet valve seat 155, and the outlet cavity 159 may be manufactured in any suitable way, such as by using any suitable etching, molding, stamping and machining process. Such a machining process may include the use of physical tools, such as a drill; the use of electromagnetic energy, such as a laser; and the use of a water jet.

The membrane 136 may be made from any suitable strong, durable, flexible, material which is compatible with the medication 12. The membrane 136 may also be elastic.

If the pump 130 is intended to pump a medication 12 which is to be supplied to a human or an animal, then any part of the pump 130 which is exposed to the medication 12 should be made from, and assembled or bonded with, non-toxic materials. Alternatively, any toxic material which is used to manufacture the pump 130, and which is exposed to the medication 12 during use of the pump 130, may be provided with any suitable non-toxic coating which is compatible with the medication 12.

Suitable materials for the substrate 132 and the membrane 134 may be metals (such as titanium), glasses, ceramics, plastics, polymers (such as polyimides), elements (such as silicon), various chemical compounds (such as sapphire, and mica), and various composite materials. In general, because the dimensions of the pump 130's various components may not be as critical as the dimensions of the various components of the regulator 32 of FIGS. 1-2, there may be more options regarding the materials from which the pump 130's substrate 132 and membrane 136 may be made.

The substrate 132 and the membrane 136 may be assembled or bonded together in any suitable leak-proof way, such as those described above for assembling or bonding together the regulator 32's substrate 34 and membrane 36 of FIGS. 1-2, except for those differences, if any, which will be made apparent by an examination of all of the Figures and disclosures in this document.

The manufacture of the pump 130's inlet port 142, inlet cavity 153, inlet valve seat 154, pumping cavity 140, pumping flexure supports 148, input valve flexure support bosses 156, channel 147, outlet valve cavity 144, outlet valve seat 155, outlet cavity 159 and outlet port 146 may be done in any suitable way, such as by using processes which are the same as, or similar to, those used for manufacturing the radial flow regulator 32's inlet channels 38, inlet cavity 40, regulator seat 42, outlet cavity 52 and outlet port 54, except for those differences, if any, which will be made apparent by an examination of all of the Figures and disclosures in this document.

One example of how the example pump 130, having the physical parameters which were set forth above, may be manufactured will now be given. The starting point may be a 76.2 mm diameter wafer of Corning 7740 Pyrex glass, which will form the pump 130's substrate 132.

The inlet cavity 153, the inlet valve seat 152, the inlet valve flexure support bosses 156, the pumping cavity 140, the pumping flexure supports 148, the channel 147, the outlet valve cavity 144, the outlet valve seat 155, and the outlet cavity 159 may be formed in the substrate 132 in any suitable way. One suitable way may be to first etch into the substrate, to a depth of about 16 microns, what will be the inlet cavity 153, the inlet valve seat 152, the pumping cavity 140, the inlet valve flexure support bosses 156, the channel 147, the outlet valve cavity 144, and the outlet cavity 159. Then, what will be the inlet cavity 152, the pumping cavity 140, the channel 147, the outlet valve cavity 144, and the outlet cavity 159 may be etched into the substrate about an additional 9 microns. What will be the pumping flexure supports 148 and the outlet valve seat 155 may not be etched at all.

The inlet and outlet ports 142, 146 may then be formed in the substrate 132 in any suitable way. The structure, operation, theory and manufacture of the pump 130's inlet and outlet ports 142, 146 may be the same as, or at least similar to, those of the radial flow regulator 32's outlet port 54 of FIGS. 1-2, except for those differences, if any, which will be made apparent by an examination of all of the Figures and disclosures in this document.

Next, a nominal layer of one or more corrosion-resistant material substances may then be deposited onto all of the surfaces of the inlet port 142, the inlet cavity 153, the inlet valve seat 154, the inlet valve flexure support bosses 156 (except for the top surfaces of the flexure support bosses 156), the pumping cavity 140, the pumping flexure supports 148, the channel 147, the outlet valve cavity 144, the outlet valve seat 155, the outlet cavity 159, and the outlet port 146. The structure, operation, theory and manufacture of such a layer of one or more corrosion-resistant substances for the pump 130 may be the same as, or at least similar to, those of the layer of one or more corrosion-resistant substances for the radial flow regulator 32 of FIGS. 1-2, except for those differences, if any, which will be made apparent by an examination of all of the Figures and disclosures in this document.

It has been discovered that such a layer of corrosion-resistant substance(s) may serve at least two important functions, in addition to its corrosion-resistant function, if the membrane 136 is anodically bonded to the substrate 132. First, the layer of corrosion-resistant substance(s) may prevent the pumping flexure 160 from sticking to the pumping flexure supports 148 during the anodic bonding process. Second, it may also prevent the outlet valve flexure 157 from sticking to the outlet valve seat 155 during the anodic bonding process.

Manufacturing the inlet valve flexure 154 and mounting it to the tops of the inlet valve flexure support bosses 156 may be done in any suitable way. The structure, operation, theory and manufacture of the pump 130's inlet valve flexure 154 and the bonding of the inlet valve flexure 154 to its substrate 132 is the same as, or at least similar to, that of the radial flow regulator 32's membrane 36, and the bonding of the membrane 36 to its substrate 34, except for those differences, if any, which will be made apparent by an examination of all of the Figures and disclosures in this document.

For example, the inlet valve flexure 154 may be manufactured from a prime silicon wafer having a boron-doped epitaxial silicon layer which has been deposited onto its top surface. Since the boron doped epitaxial silicon layer will ultimately form the pump 130's inlet valve flexure 154, the layer's thickness will depend on the desired thickness of the inlet valve flexure 154. The boron-doped epitaxial silicon layer, and thus the inlet valve flexure 154 may be about 9 microns thick, for example. The boron doping may be in excess of $3 \times 10^{19}$ atoms of boron per cubic centimeter, which conveys a dramatic etch-resistance to the epitaxial silicon layer in silicon etchants based on ethylene diamine.

First, the boron-doped silicon wafer may be cleaned; a thin chrome metallization layer may be applied on top of the wafer's boron-doped top surface; and a thin layer of any suitable photoresist may then be applied on the top of the chrome layer, and then dried. An image of the outline of the inlet valve flexure 154 may then be exposed onto the photoresist, and then developed; after which the boron-doped silicon wafer may be cleaned and dried.

As a result of the forgoing procedure, the chrome layer will now bear an image, unprotected by the photoresist, of the outline of the inlet valve flexure 154. The unprotected portion of the chrome layer may then be etched away; resulting in an image of the outline of the inlet valve flexure 154 having been formed on the silicon wafer's boron-doped top surface. The image of the outline of the inlet valve flexure 154 may then be etched into silicon wafer's boron-doped top surface, in any suitable way, such as by using an aggressive, isotropic etchant, to a depth which is deeper than the thickness of the silicon wafer's boron-doped top surface.

Then the photoresist and chrome layers may be removed by any suitable means; and the boron-doped silicon wafer may be cleaned and dried.

The non-doped surface of the boron-doped silicon wafer may then be etched away in any suitable way, such as by the use of an ethylene diamine etchant; thereby leaving the desired inlet valve flexure 154 free standing. The free standing inlet valve flexure 154 may then be aligned with, and bonded to its bosses 156 in any suitable way, such as in a way which is the same as, or at least similar to, that used to bond the radial flow regulator 32's membrane 36 to its substrate 34, except for those differences, if any, which will be made apparent by an examination of all of the Figures and disclosures in this document. One suitable way may be to use anodic bonding. During the bonding process, the inlet valve flexure 154 may be held in place on its bosses 156 in any suitable way, such as by using small pins, or by using electrostatic forces.

Manufacturing the membrane 136 and bonding it to the glass wafer (which is the substrate 132) may be done in any suitable way. The structure, operation, theory and manufacture of the pump 130's membrane 136 and the bonding of the membrane 136 to its substrate 132 to form a silicon/glass sandwich is the same as, or at least similar to, the manufacturing of the radial flow regulator 32's membrane 36, and the bonding of the membrane 36 to its substrate 34 to form a silicon/glass sandwich, except for those differences, if any, which will be made apparent by an examination of all of the Figures and disclosures in this document.

The piezoelectric motor 138 may be manufactured by forming the piezoelectric and cover disks 162, 164 in any suitable way, such as by using any suitable etching, molding, stamping, and machining process. The disks 162, 164 may be of comparable thickness, and may be firmly bonded to each other in any suitable way, such as by using a silver epoxy bonding material.

The piezoelectric disk 162 may be manufactured from any suitable piezoelectric material, such as a piezoelectric ceramic material called PZT5H, which is made by Vernitron Corp., located in Bedford, Ohio. Preferably, the top and bottom surfaces of the piezoelectric disk 162 may be provided with a thin conductive coating of any suitable metal, such as nickel, to make it more convenient to electrically excite the piezoelectric disk 162. The cover disk 164 may be manufactured from any suitable electrically conductive, relatively stiff, resilient material. A metal, such as stainless steel, may be suitable.

The wire 170 may be electrically connected to the motor 138's cover disk 164 in any suitable way, such as by using a bead 174 of electrically conductive epoxy material. The wire 172 may be electrically connected to the bottom of the piezoelectric disk 162 in any suitable way, such as by using gold wire bonding, as practiced in the semiconductor industry. The wire 172 may have a diameter selected to be equal to the desired thickness of the layer of bonding material 168, thereby defining the desired spacing between the piezoelectric disk 162 and the flexure 160.

The motor 138's piezoelectric disk 162 may be bonded to the pumping flexure 160's top surface in any suitable way, such as by using a layer of bonding material 168. The bonding material may be a hard bonding material (such as an epoxy); but preferably, it may be a soft, gel-like polymer, such as silicone rubber. For example, a suitable soft, gel-like polymer may be Sylgard 527 brand silicone rubber, made by the Dow Corning Company, located in Midland, Mich.

The manufacture of only one pump 130 was described above. However, it will be appreciated that on any pair of glass and silicon wafers the substrates 132 and membranes 136 for numerous pumps 130 could be manufactured simultaneously in a manner similar to that described above. If such is the case, an array of substrates 132 may be simultaneously etched in the glass wafer. Then an array of inlet valve flexures 154 may be manufactured, aligned, and bonded to their respective bosses 156; after which the silicon and glass wafers for the substrates 132 and membranes 136 may be aligned and bonded together. Then, all of the membranes 136 may be formed simultaneously by grinding and etching the silicon wafer for the membranes 136 to its desired final thickness. Next, a piezoelectric motor 138 for each pump 130 may be manufactured and bonded, along with its wires 170, 172, to its respective pump 130. The silicon/glass substrate 132/membrane 136 sandwich may then be divided by any suitable means (such as dicing) into individual chips, each chip bearing at least one pump 130.

One of the advantages of using the etching and anodic bonding processes which were described in detail above is that such processes enable high quality, very reliable pumps 130 to be mass produced in great numbers at a cost so low that the pump 130 may be considered to be disposable. In addition, it should also be noted that the pump 130 is stunning in its simplicity since its membrane 136 serves as both the pumping flexure 160 and the outlet valve flexure 157; and since the parts which move (i.e., the inlet valve flexure 154, the pumping flexure 160, the motor 138 and the outlet valve flexure 157) merely bow during operation. Further, because the raw materials from which the pump 130 may be made may be very inexpensive, such as glass and silicon, the cost of the pump 130 may held to a very low level.

MICROMACHINED DIAPHRAGM PUMP 180 HAVING INTEGRAL VALVING AND AN EDGE LOCATED INLET PORT (FIGS. 18–19): STRUCTURE, OPERATION, THEORY AND MANUFACTURE

The micromachined diaphragm pump 180 which is illustrated in FIGS. 18–19 is the same as, or at least similar to, the pump 130 of FIGS. 16–17 in its structure, operation, theory and manufacture, except for those differences which will be made apparent by an examination of all of the Figures and all of the disclosures in this document. Accordingly, the respective parts of the pump 180 of FIGS. 18–19 have been given the same reference numerals as the corresponding parts of pump 130 of FIGS. 16–17, for clarity and simplicity.

Turning again to FIGS. 18–19, the pump 180's inlet valve 134 may comprise a one-way flapper valve having a cantilevered flexure 154. One end of the flexure 154 may be mounted to its support boss 156, while the flexure 154's free end may lay over the inlet valve seat 152 when no voltage is applied to the motor 138's wires 170, 172. Although one particular form of one-way inlet valve 134 is illustrated in FIGS. 17–18, the pump 180's one-way inlet valve 134 may be any other suitable one-way valve, such as the one-way valves which are disclosed in this document.

As seen, the pump 180's inlet valve 134 may be located near an edge of the pumping cavity 140. It has been discovered that locating the inlet valve 134 near an edge of the pumping cavity 140 may have at least two advantages. First, it may enable the priming of the pumping cavity 140 to occur in a very automatic, reproducible way when the pump 180 is turned on. Such priming may occur because the surface tension of the medication 12 may initially draw the medication 12 in around the perimeter of the pumping cavity 140, where the surface tension curvature forces are the strongest. Such priming by surface tension is given by the following equation:

$$\Delta P = \gamma \left( \frac{1}{r_{c1}} + \frac{1}{r_{c2}} \right)$$

where $\Delta P$ is pressure, where $\gamma$ is the surface tension, and $r_{c1}$ and $r_{c2}$ are the two orthogonal radii of curvature describing a point on the fluid's surface. Near the periphery of the pumping cavity 140, one radius will be equal to approximately the pumping cavity 140's radius, while the other radius will be equal to one-half of the pumping cavity 140's depth. Since the flexure 160's center may be bowed away from the pumping cavity 140's bottom, resulting in lower surface tension priming pressures there, the initiation of priming around the pumping cavity 140's periphery will generally result in a more natural and reproducible total priming.

Such priming of the pumping cavity 140 may be advantageous because it has been discovered that it may help to eliminate any "dead spots" or bubbles inside of the pump 180. Not having any such "dead spots" or bubbles in the pump 180 is desirable because such bubbles may get caught in the inlet and outlet valves 134, 137 and cause high surface tension $\Delta P$'s because of the small dimensions of the inlet and outlet valves 134, 137; and thus may adversely affect the operation of the inlet and outlet valves 134, 137. In addition, if the pump 180 is used in a medical device, such bubbles may result in dangerous, or even fatal, embolisms in the patient.

The second advantage of locating the inlet valve 134 near an edge of the pumping cavity 140 is that it has been discovered that such a location for the inlet valve 134 may also enable the pump 180 to clean itself of any bubbles which may have formed in its pumping cavity 140 for any reason. This is because during operation of the pump 180 the flow of the medication 12 will be from the inlet port 142, across the pumping cavity 140, through the channel 147, across outlet valve cavity 144, and out of the outlet port 146, thereby tending to sweep any such bubbles out of the pumping cavity 140, the channel 147, the outlet valve cavity 147, the outlet cavity 159, and the outlet port 146.

As seen in FIGS. 18 and 19, the eleven membrane supports 148 may comprise cylindrical pins having any suitable diameter, such as about 0.5 mm. As was mentioned above, it has been discovered that using relatively small cylindrical pin shaped flexure supports 148 (FIGS. 18–19), instead of relatively large radial spine type flexure supports 148 (FIGS. 16–17), may be advantageous for at least four reasons. First, they may have less flow resistance to the medication 12 being pumped by the pump 130. Second, they may have less adverse impact on the priming of the pumping cavity 140. Third, they may have less propensity to undesirably trap bubbles within the pumping cavity 140. Fourth, they may have less of an adverse impact on the ability of the medication 12 to sweep any bubbles out of the pumping cavity 140 during operation of the pump 130.

Although eleven, cylindrical flexure supports 148 are illustrated in FIGS. 17–18, there may be fewer or more flexure supports 148, and each flexure support 148 may have any other suitable size and shape.

By way of example, the diaphragm pump 180 may weigh about 0.6 grams; and may have the following physical parameters. The substrate 132 may be a square having sides about 1.30 cm long, and may have a thickness of about 0.5 mm. The membrane 136 may have a thickness of about 25 microns. The inlet valve flexure 154 may have a thickness of about 9.0 microns, a width of about 1600 microns, and a length of about 2000 microns. The pumping cavity 140 may have a diameter of about 1.07 cm, and the outlet valve cavity 144 may have a diameter of about 3.4 mm. The cavities 140, 144 may each have a depth of about 25.0 microns. The channel 147 may have a width of about 0.5 mm, a length of about 1.0 mm, and a depth of about 25 microns. The inlet and outlet ports may have a minimum diameter of about 100 microns. The flexure supports 148 and the outlet valve seat 154 may each have a height of about 25 microns. The inlet valve seat 152 and the inlet valve flexure bosses 156 may each have a height of about 9.0 microns. The piezoelectric motor 138 may act as about a 0.02 μF capacitor; and its disks 162, 164 may each have a thickness of about 0.15 mm and a diameter of about 1.1 cm. The bonding material 168, which bonds the disk 162 to the pumping flexure 160's top surface may have a thickness of about 50.0 microns thick; and the wires 170, 172 may have a diameter of about 50.0 microns. This example pump 180 may deliver about 0.1–1.0 microliters of the medication 12 per pumping cycle; and operate at a frequency of from about 0.0 to about 25.0 pumping cycles per second.

During operation of the pump 180, when any suitable source of electrical power is applied to its motor 138's wires 170, 172, or when the voltage of that source of electrical power is increased, the centers of the motor 138 and the pumping flexure 160 tend to bow away from the pumping cavity 140's bottom 150 to form a cupped shape. As this happens, the outlet valve 137 closes; the inlet valve 134 opens; and the medication 12 is drawn into the pumping cavity 140 through the inlet port 142 and the inlet valve 134.

On the other hand, when the source of electrical power to the motor 138's wires 170, 172 is reduced, is interrupted, or has its polarity reversed, the centers of the motor 138 and the pumping flexure 160 tend to automatically return to their original flat configurations (if the power is reduced or interrupted), or tend to be displaced towards the pumping cavity 140's bottom 150 (if its polarity is reversed). As this happens, the inlet valve 134 is closed; the outlet valve 137 is opened; and the medication is pumped from the pumping cavity 140 into the channel 147, into the outlet valve cavity 144, and out through the outlet valve 137 and the outlet port 146.

MICROMACHINED DIAPHRAGM PUMP 190 HAVING MODULAR VALVING AND AN EDGE LOCATED INLET PORT (FIGS. 20–22):
STRUCTURE

Figure 20:
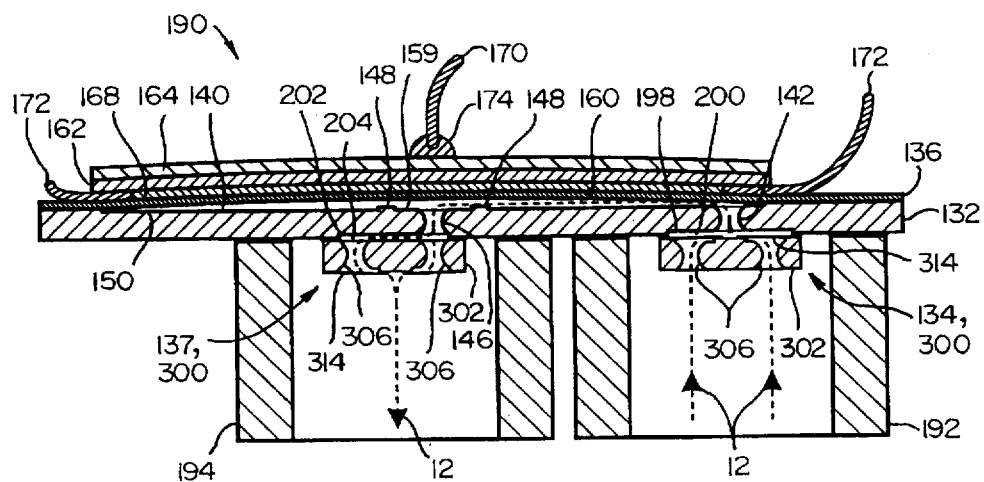
FIG. 20 is a cross-sectional view, partly in a cross-section taken substantially along line 20—20 of FIGS. 21–22, of a micromachined diaphragm pump of the present invention having modular valving and an edge located inlet port.
Figure 21:
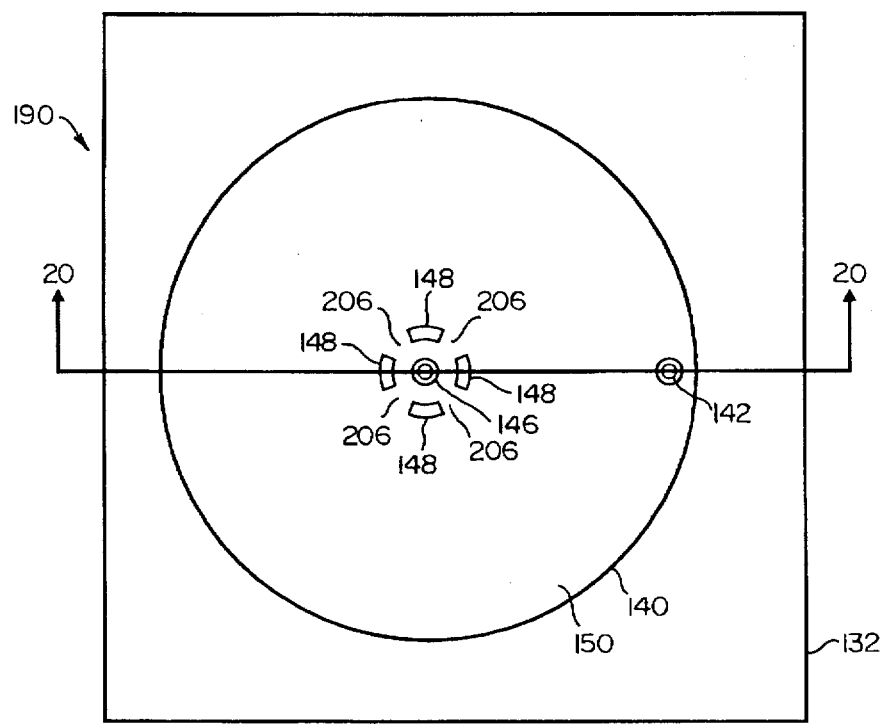
FIG. 21 is a top plan view of the entire substrate thereof.
Figure 22:
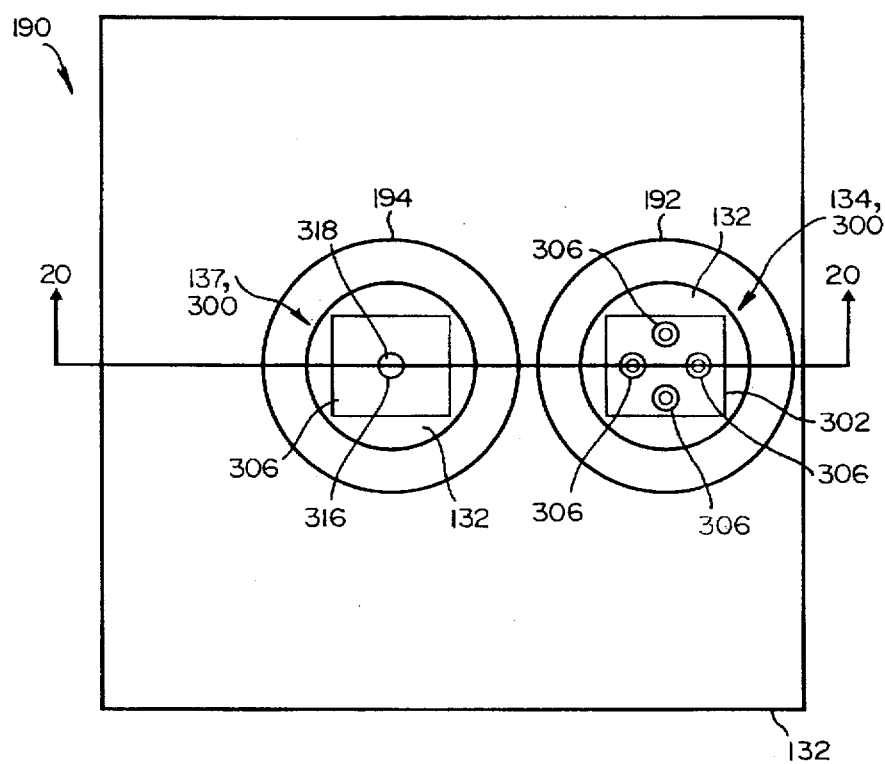
FIG. 22 is bottom plan view of the pump of FIG. 20.

The micromachined diaphragm pump 190 which is illustrated in FIGS. 20–22 is the same as, or at least similar to, the pumps 130, 180 of FIGS. 16–19 in its structure, except for those differences which will be made apparent by an examination of all of the Figures and all of the disclosures in this document. Accordingly, the respective parts of the pump 190 of FIGS. 20–22 have been given the same reference numerals as the corresponding parts of the pumps 130, 180 of FIGS. 16–19, for clarity and simplicity.

Although, as best seen in FIGS. 20–21, the pump 190's four pumping flexure supports 148 are arcuate in shape, and surround the outlet port 146, there may be fewer or more of the pump 190's pumping flexure supports 148, and each such pumping flexure support 148 may have any other suitable size, shape and location. Preferably, spaces 206 may be provided between the pumping flexure supports 148, in order to help provide fluid paths for the medication 12 as it travels from the inlet port 142 to the outlet port 144. Alternatively, the spaces 206 may be eliminated, and the four arcuate pumping flexure supports 148 may be merged into an outlet valve seat 155 having any suitable size and shape.

While the pumps 130, 180 may have their inlet valves 134 located inside of their pumping cavities 140, the pump 190's inlet valve 134 may be secured to the exterior of its substrate 132 over its inlet port 142, as seen in FIG. 20.

Similarly, while the pumps 130, 180 may have their outlet valves 137 and their outlet ports 146 located on the inside of their outlet valve cavities 144, (with a channel 147 being provided between their pumping cavities 140 and their outlet valve cavities 144); the pump 190 may have may have no channel 147, may have no outlet valve cavity 144, may have its outlet port 146 located in the center of its pumping cavity 140, and may have its outlet valve 137 secured to the exterior of its substrate 132 over its outlet port 146, as seen in FIG. 20.

The pump 190's one-way inlet and outlet valves 134, 137 may be any suitable one-way valve, such as the one-way valves which are disclosed in this document. For example, the one-way valve 300 of FIGS. 30–31 may be suitable. The structure, operation, theory and manufacture of the one-way valve 300 illustrated in FIGS. 30–31 will be discussed in detail below.

The medication 12 may be conveyed to the inlet valve 134 and conveyed from the outlet valve 137 in any suitable way, such as by using inlet and outlet tubes 192, 194, respectively, which are secured to the substrate 132.

As seen in FIG. 20, the substrate 132 may be provided with an inlet valve recess 198, in order to provide an inlet valve gap 200 between the pump 190's substrate 132 and the inlet valve 134. The inlet valve gap 200 may serve to permit the inlet valve 134's flexure 314 to deflect towards the substrate 132 during flow of the medication 12 into the pumping cavity 140 while the pump 190 is operating. However, the inlet valve recess 198 may be eliminated, and the inlet valve gap 200 may be formed in any other suitable way, such as by providing a spacer between the substrate 132 and the inlet valve 134, or by forming a raised separator on the substrate 132 and/or on the inlet valve 134.

Similarly, as also seen in FIG. 20, the substrate 132 may be provided with an outlet valve recess 202, in order to provide an outlet valve gap 204 between the substrate 132 and the outlet valve 137. The outlet valve gap 204 may serve to provide a circumferentially more uniform flow of the medication 12 from the pump 190's outlet port 146 to the outlet valve 137's inlet ports 306 during operation of the pump 190. However, the outlet valve recess 202 may be eliminated, and the outlet valve gap 204 may be formed in any other suitable way, such as by providing a spacer between the substrate 132 and the outlet valve 137, or by forming a raised separator on the substrate 132 and/or on the outlet valve 137.

By way of example, the diaphragm pump 190 may weigh about 1.0 gram; and may have the following physical parameters. The substrate 132 may be a square having sides about 1.30 cm long; and a thickness of about 0.5 mm. The membrane 136 may have a thickness of about 25 microns. The pumping cavity 140 may have a diameter of about 1.07 cm, and a depth of about 25 microns. The inlet and outlet ports 142, 146 may have a minimum diameter of about 100 microns. The flexure supports 148 may have a height of about 25 microns. The piezoelectric motor 138 may act as about a 0.02 µF capacitor; and its disks 162, 164 may have a thickness of about 0.15 mm, and a diameter of about 1.1 cm. The bonding material 168, which bonds the disk 162 to the pumping flexure 160's top surface may be about 50.0 microns thick; and the wires 170, 172 may have a diameter of about 50.0 microns. This example pump 180 may deliver about 0.1–1.0 microliters of the medication 12 per pumping cycle; and operate at a frequency of from about 0.0 to about 25.0 pumping cycles per second.

MICROMACHINED DIAPHRAGM PUMP 190 HAVING MODULAR VALVING AND AN EDGE LOCATED INLET PORT (FIGS. 20–22): OPERATION AND THEORY

The micromachined diaphragm pump 190 which is illustrated in FIGS. 20–22 is the same as, or at least similar to, the pumps 130, 180 of FIGS. 16–19 in its operation and theory, except for those differences, if any, which will be made apparent by an examination of all of the Figures and all of the disclosures in this document.

One of the significant features of the pump 190 is the simplicity of its substrate 132. That is, its substrate 132 has etched into it only the pumping cavity 140, the inlet and outlet ports 142, 146, and the pumping flexure supports 148. Its substrate 132 does not have, or need, inlet or outlet cavities 153, 159; inlet or outlet valve seats 152, 155; inlet valve flexure support bosses 156; a channel 147; or an outlet valve cavity 144. Such simplicity of the pump 190's substrate 132 inherently makes it easier and quicker to manufacture, with fewer steps, and at a lower cost; as compared to the substrates 132 of the pumps 130, 180.

Another significant feature of the pump 190 is that its inlet and outlet valves 134, 137 may be modular in nature; making the pump 190 both easy and inexpensive to assemble. In addition, since the inlet and outlet valve 134, 137 may be modular in nature, they need not be necessarily secured directly to the substrate 132. Instead, either or both of the inlet and outlet valves 134, 137 may be located away from the substrate 132, such as in the inlet and outlet tubes 192, 194, respectively.

During operation of the pump 190, when any suitable source of electrical power is applied to the motor 138's wires 170, 172, or when the voltage of that source of electrical power is increased, the centers of the motor 138 and the pumping flexure 160 tend to bow away from the pumping cavity 140's bottom 150, to form a cupped shape. As this happens, the outlet valve 137 closes; the inlet valve 134 opens; and the medication 12 is drawn into the pumping cavity 140 from the inlet tube 192 through the inlet valve 134 and the inlet port 142.

On the other hand, when the source of electrical power to the motor 138's wires 170, 172 is reduced, is interrupted, or its polarity is reversed, the centers of the motor 138 and the pumping flexure 160 tend to automatically return to their original flat configurations (if the power is reduced or interrupted), or tend to be displaced towards the pumping cavity 140's bottom 150 (if its polarity is reversed). As this happens, the inlet valve 134 closes; the outlet valve 137 opens; and the medication 12 is pumped out of the pumping cavity 140 into the outlet tube 194 through the outlet port 146 and the outlet valve 137.

Locating the inlet port 142 near an edge of the pumping cavity and locating the outlet port 146 near the center of the pumping cavity may help to prevent any bubbles from being trapped within the pumping cavity. This is because the medication 12 will tend to sweep any such bubbles out of the pumping cavity as it flows from the inlet port 142 to the outlet port 146.

Undesired forward flow of the medication 12 through the pump 190 caused by overpressurization of the medication 12 in the inlet tube 192 may be reduced, or even eliminated, in at least three ways. First, it has been discovered that such undesired forward flow of the medication 12 during overpressurization may be reduced, or even eliminated, by changing the pumping flexure supports 148 into an outlet valve seat 155, in the manner described previously; and by sizing the pump 190 so that the bottom of the pumping flexure 160 rests on the top of the outlet valve seat 155 when no voltage is being applied to the pump 190's motor 138.

Thus, before there is any undesired forward flow of the medication 12 into the pumping cavity 140 caused by such overpressurization of the medication 12, the force generated by that overpressurization on the bottom surface of the pumping flexure 160 would have to overcome at least three things: First, it may have to lift the weight of the pumping flexure 160 and the motor 138. Second, it would have to overcome the stiffness of both the pumping flexure 160 and the motor 138, which may be much stiffer than the inlet valve flexure 314. Third, it would have to overcome the effect of any pre-load of the pumping flexure 160's bottom surface, or its raised boss (if any), on the outlet valve seat 155. Accordingly, these three factors may result in the pump 130 having a significantly lower forward bleed rate of the medication 12 into the pumping cavity 140 in the event of such overpressurization, than would be the case if there were no outlet valve seat 155, or if the pumping flexure 160 (or its raised boss) was not resting on the top surface of the outlet valve seat 155 when there is no voltage applied to the pump 130.

Second, it has also been discovered that the undesired forward bleeding of the medication 12 through the pump 190 in the event of such overpressurization of the medication 12 may also be reduced, or even eliminated, by reversing the polarity of the electric power which is applied to the motor 138's wires 170, 172. This causes the motor 138, and the pumping flexure 160, to tend assume a cupped shape, with the center of the membrane 136's pumping portion 160 being pushed against the outlet valve seat 155 (assuming the pumping flexure supports 148 were changed into an outlet valve seat 155, in the manner describe previously); thereby preventing the medication 12 from exiting the pumping cavity 140 through the outlet port 154, despite such overpressurization of the medication 12.

Third, it has been discovered that the undesired forward bleeding of the medication 12 through the pump 190 in the event of such overpressurization of the medication 12 may also be reduced, or even eliminated, by mounting the pump 190 so that the upper surface of the motor 138 is exposed to the medication 12 at the pressure of the medication 12 in the inlet 192. In such an event the pump 190 may act as a flow regular, similar to the flow regulator 32 of FIGS. 1–2. That is, the pump 190's outlet valve seat 155 (assuming the pumping flexure supports 148 were changed into an outlet valve seat 155, in the manner describe previously); and the corresponding portion of its pumping flexure 160 may operate in a fashion similar to that previously described regarding the flow regulator 32's regulator seat 42 and its flexure 28. That is, the pump 190's outlet valve seat 155 and the corresponding portion of its pumping flexure 160 may regulate the flow rate (Q) of the medication 12 through the pump 190 within a pre-determined range of the flow rate (Q) and the driving pressure difference (P), and to completely shut off the flow rate (Q) of the medication 12 if the driving pressure difference (P) of the medication 12 between the pump 190's inlet and outlet ports 142, 146 exceeds a predetermined value.

The maximum permissible flow rate (Q) of the medication 12 through the pump 190 may also be regulated in at least two additional ways. First, it may be regulated by adjusting the height of the inlet valve gap 200 in any suitable way, such as by selecting the depth of the inlet valve recess 198 and by selecting the thickness of the inlet valve 134's flexure 314. The height of the inlet valve gap 200 controls the flow rate (Q) because the flexure 314's maximum deflection during operation of the pump 190 is limited by the height of the inlet valve gap 200. That is, as the height of the inlet valve gap 200 is decreased, the flexure 314's maximum deflection is also decreased, thereby reducing the maximum flow rate (Q) of the medication 12 through the inlet valve 134 for any given driving pressure difference (P) (and vice versa).

Figure 20A:
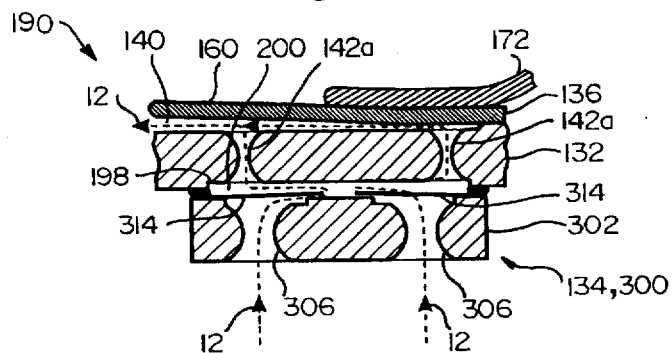
FIG. 20A is a fragmentary cross-sectional view of a modification of the inlet portion thereof.

The second additional way that the maximum permissible flow rates (Q) of the medication 12 through the pump 190 may be regulated is by discharging the medication 12 into the pumping cavity 140 through one or more inlet ports 142a in the substrate 132 that are placed around the perimeter of the inlet valve flexure 304, rather than coaxial with the inlet valve 134, as shown in FIG. 20A. If that is done, the configuration of the inlet valve 134 may match that of the radial flow regulator 32 described above, and may regulate the flow rate (Q) of the medication 12 through the pump 190 within a pre-determined range of (Q) and driving pressure difference (P), and may completely shut off the flow rate (Q) of the medication 12 if the driving pressure difference (P) of the medication 12 at the inlet 192 exceeds a pre-determined amount.

MICROMACHINED DIAPHRAGM PUMP 190 HAVING MODULAR VALVING AND AN EDGE LOCATED INLET PORT (FIGS. 20–22): MANUFACTURE

The micromachined diaphragm pump 190 which is illustrated in FIGS. 20–22 is the same as, or at least similar to, the pumps 130, 180 of FIGS. 16–19 in its manufacture, except for those differences, if any, which will be made apparent by an examination of all of the Figures and all of the disclosures in this document.

The pump 190's inlet and outlet valve recesses 198, 202 may be manufactured in any suitable way, such as by using an etching process similar to that used to manufacture the flow regulator 32's cavities 40, 52. The inlet and outlet valve recesses 198, 202 may be provided with a layer of one or more corrosion-resistant substances in any suitable way, such as those described above for the radial flow regulator 32's layer of corrosion-resistant substances.

The pump 190's inlet and outlet valves 134, 137, and its inlet and outlet tubes 192, 194, may be assembled or bonded to its substrate 132 in any suitable leak-proof way, such as those described above for assembling or bonding together the radial flow regulator 32's substrate 34 and membrane 36.

MICROMACHINED ONE-WAY MEMBRANE VALVE 210 HAVING A RECTANGULAR FLEXURE AND A RING-SHAPED INLET VALVE SEAT (FIGS. 23–25): STRUCTURE

Figure 23:
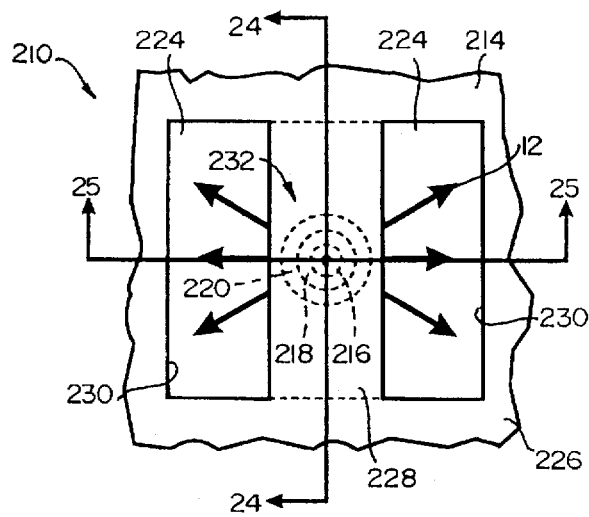
FIG. 23 is top plan view of a first embodiment of the micromachined one-way valve of the present invention.
Figure 24:
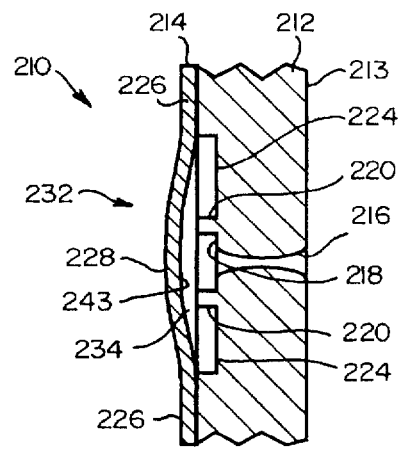
FIG. 24 is a cross-sectional view thereof, taken substantially along line 24—24 of FIG. 23.
Figure 25:
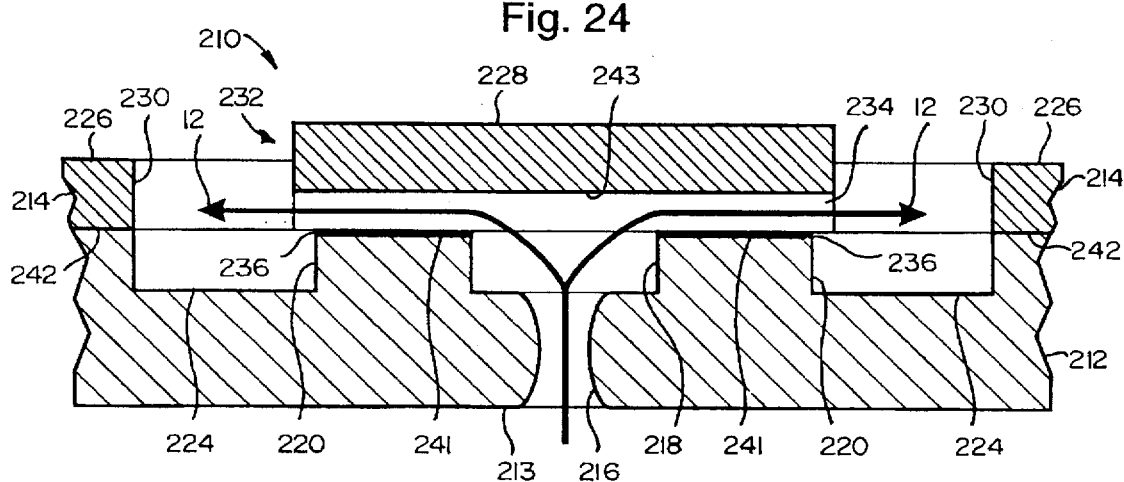
FIG. 25 is a cross-sectional view thereof, taken substantially along line 25—25 of FIG. 23.

The first embodiment of the micromachined one-way membrane valve 210 is illustrated in FIGS. 23–25. The membrane valve 210 may comprise a substrate 212, and a membrane 214.

The substrate 212 may have an inlet port 216; an inlet cavity 218; an inlet valve seat 220; and an outlet cavity 224.

Although a single inlet port 216 and a single inlet cavity 218 are illustrated, there may be more than one of each of these elements.

Although an inlet port 216 having a venturi-shaped configuration for better fluid flow is illustrated, it may have any other suitable shape, such as round or cylindrical. Although the inlet port 216 is illustrated as being co-axial with the inlet cavity 218, it may have any other suitable spatial relationship with respect to the inlet cavity 218. For example, the inlet port 216 might be transverse to the inlet cavity 218, and enter the inlet cavity 218 from its side, rather from beneath.

Although an inlet cavity 218 having a circular or cylindrical configuration and a uniform depth is illustrated, it may have any other suitable size and configuration, and a non-uniform depth. The inlet cavity 218 may be used to define a clean outer perimeter for the inlet port 216, particularly if the inlet port 216 is drilled with a laser. However, the inlet port 216 may be eliminated, and the inlet cavity 218 may be extended downwardly so that it communicates directly with the substrate 212's bottom surface 213. Alternatively, the inlet cavity 218 may be eliminated, and the inlet port 216 may be extended upwardly so that it communicates directly with the substrate 212's top surface 242.

Although one rectangular outlet cavity 224 having a uniform depth is illustrated, there may be more than one outlet cavity 224, and each such outlet cavity may have any other suitable size, shape and depth; and its depth may not be uniform. Alternatively, the outlet cavity 224 may be eliminated, so that the inlet valve seat 220 may simply be all or part of those portions of the substrate 212's top surface 242 which underlie the flexure 228.

Although the inlet valve seat 220 is illustrated as having a ring-shaped configuration, it may have any other suitable configuration, such as square or rectangular.

The membrane 214 may comprise a mounting portion 226 which is mounted to the substrate 212; a flexure 228 which is not mounted to the substrate 213, and which extends across the inlet valve seat 220; and a pair of outlet ports 230.

The substrate 212 and the membrane 214 may have any other suitable size, shape and thickness. Although the substrate 212 and the membrane 214 are illustrated as being of uniform thickness, they may have a non-uniform thickness.

Although a rectangular flexure 228 of uniform thickness is illustrated, the flexure 228 may have any other suitable shape, and its thickness may not be uniform.

Although two rectangular outlet ports 230 are illustrated, there may be fewer, or more, outlet ports 230, and each outlet port may have any suitable shape.

Together, the substrate's inlet valve seat 220 and the membrane's flexure 228 comprise an inlet valve 232. Preferably, the top of the inlet valve seat 220 and the top 242 of the rest of the substrate 212 may be coplanar, so that when there is no positive driving pressure difference (P) across the one-way membrane valve 210, the flexure 228 lies flat across the top of the inlet valve seat 220.

Although only one inlet valve 232 is illustrated, there may be more than one inlet valve 232. Although the inlet valve 232 is illustrated as having only flexure 228 and one inlet valve seat 220, each inlet valve 232 may have more than one flexure 228 and more than one inlet valve seat 220.

By way of example, the one-way membrane valve 210 may have the following physical parameters. The one-way membrane valve 210 may be manufactured on a square chip having sides about 3900 microns long. The substrate 212 may be manufactured from 7740 Pyrex glass and have a maximum thickness of about 0.5 mm. The inlet port 216 may have a minimum diameter of about 50 microns, and a length of about 475 microns. The inlet cavity 218 may have a diameter of about 635 microns, and a depth of about 25 microns. The inlet valve seat 220 may have an outer diameter of about 1143 microns, and an inner diameter of about 635 microns. The outlet cavity may be a square having sides about 2900 microns long, and may have a depth of about 25 microns. The membrane 214 may be manufactured from silicon, and may have a thickness of about 9.0 microns. The outlet ports 230 may each have a width of about 480 microns, and a length of about 2900 microns. The flexure 228 may have a thickness of about 9.0 microns, a length of about 2900 microns, and a width of about 1940 microns.

Figure 29A:
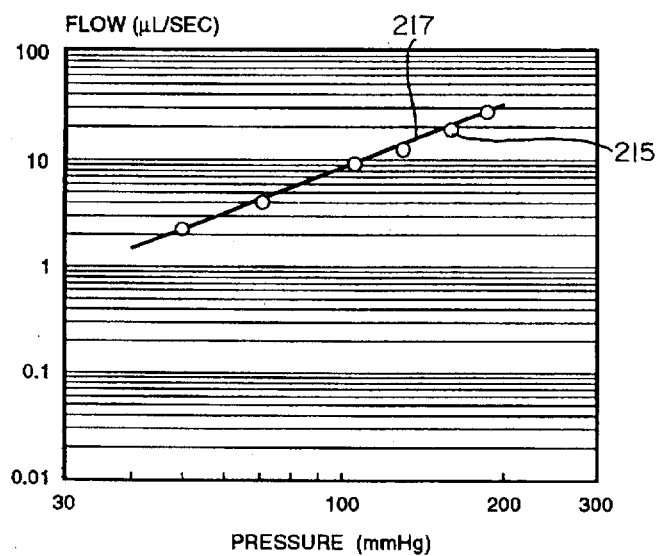
FIG. 29A is a graph depicting certain fluid flow characteristics of the first embodiment of the micromachined one-way valve of the present invention.

The flow characteristics of this example one-way membrane valve 210 are illustrated in FIG. 29A.

MICROMACHINED ONE-WAY MEMBRANE VALVE 210 HAVING A RECTANGULAR FLEXURE AND A RING-SHAPED INLET VALVE SEAT (FIGS. 23–25): OPERATION AND THEORY

The valve 210 may be installed in its intended location of use in any suitable way. Any suitable medication supply means may be used to connect the one-way membrane valve 210's inlet port 216 to a source of the medication 12; and any suitable medication delivery means may be used to connect the one-way membrane valve 210's outlet ports 230 to whatever person, object or thing is to receive the medication 12 from the outlet ports 230.

During operation, as seen in FIGS. 24–25, if a positive driving pressure difference (P) is applied across the one-way membrane valve 210, such as by pressurizing the source of the medication 12 with respect to the one-way membrane valve 210's outlet ports 230, the pressure of the medication 12 beneath the flexure 228 will cause the flexure 228 to bow away from, and unseat from, the inlet valve seat 220. This will permit the medication 12 to flow in through the inlet port 216, and the inlet cavity 218; to flow radially outwardly through the valve gap 234 between the inlet valve seat 220 and the flexure 228; and to flow out through the outlet ports 224.

On the other hand, if a negative driving pressure difference (P) is applied across the one-way membrane valve 210, such as by pressurizing the medication 12 adjacent to the top of the flexure 228 with respect to the inlet port 216, the pressure of the medication 12 on top of the flexure 228 will drive the flexure 228 towards, and seat it against, the inlet valve seat 220. This will prevent any back flow of the medication 12 through the inlet port 216.

Referring now to FIG. 29A, the six circular data points 215 are for the measured flow rate (Q), in microliters per second, of the example one-way membrane valve 210, whose physical parameters were set forth above; as a function of the driving pressure difference (P) across the one-way membrane valve 210, in mm Hg. The medication 12 was distilled water. The solid line 217 shown in FIG. 29A is a data-fit line for the data points 215.

When the above example one-way membrane valve 210, whose physical parameters were set forth above, was tested in a reverse flow condition, the leak rate at about 150.0 mm Hg of pressure was less than about 0.2 microliters/second, which corresponds to a forward-to-reverse flow ratio in excess of 100:1.

It has been discovered that one of the valve 210's notable features may be that, because the flexure 228 may be so thin and flexible, it may conform unusually well to the valve seat 220's top surface 241, despite the normal, very small variations in the flatness of the flexure 228's bottom surface 243, and in the inlet valve seat 220's top surface 241. Such conformity is desirable, since it results in reducing, if not eliminating, any back flow of the medication 12 through the valve 210 when it is subjected to a negative driving pressure difference (P). In addition, such conformity is desirable because it enables the forward opening characteristics of the one-way membrane valve 210 to be "tuned".

Another of the valve 210's notable features may be the fact that both ends of its flexure 228 may be anchored to the substrate 212, as is seen FIGS. 23 and 24. Such anchoring of both ends of the flexure 228 offers numerous advantages.

For example, it has been discovered that anchoring both ends of the flexure 228 may result a flexure 228 having superior flatness (under a zero or negative driving pressure difference (P) across the valve 210), and thus having superior conformity to the inlet valve seat 220's top surface 241, as compared to a flexure 228 which is cantilevered, i.e., which is anchored at only one of its ends. This is because a flexure 228 which is anchored at both of its ends is more geometrically constrained, as compared to a cantilevered flexure 228, and thus its side edges are less likely to curl. Such flatness and conformity of the flexure 228 is desirable because it results in better sealing between the flexure 228 and the inlet valve seat 220's top surface 241; which, in turn, may reduce, if not eliminate, any back flow of the medication 12 through the valve 210 when it is subjected to negative driving pressure differences (P). In addition, such conformity is desirable because it enables the forward opening characteristics of the one-way membrane valve 210 to be "tuned".

It has been further discovered that anchoring both ends of the flexure 228 enables the flexure 228 to be "preconformed" to the inlet valve seat 220's top surface 241. By "preconformed", it is meant that the flexure 228 and the inlet valve seat 220's top surface 241 are in intimate contact when the one-way membrane valve 210 is at its designed operating temperature, and when there is a zero driving pressure difference (P) across the one-way membrane valve 210. Such preconforming results in reducing, or even eliminating, any back flow of the medication 12 through the valve 210 when it is subjected to a negative driving pressure difference (P). In addition, such preconforming is desirable because it enables the forward opening characteristics of the one-way membrane valve 210 to be "tuned".

It has also been discovered that a flexure 228 which is anchored at both ends may be used without a rigid center boss, such as the boss which is disclosed in FIG. 1 of the article entitled "A Piezoelectric Micropump Based On Micromachining Of Silicon by H.T.G. Van Lintel et al., Sensors and Actuators, 15 (1988) 153-167. It has been discovered that a flexure 228 which does not have such a rigid center boss is more flexible than one which has such a boss, and thus is more conformable to the inlet valve seat 220's top surface 228. Such conformity is desirable, since it results in reducing, if not eliminating, any back flow of the medication 12 through the valve 210 when it is subjected to a negative driving pressure difference (P). In addition, such conformity is desirable because it enables the forward opening characteristics of the one-way membrane valve 210 to be "tuned". It has also been discovered that such increased flexibility of the flexure 228 is desirable since it may be translated into either a smaller one-way membrane valve 210, or a one-way membrane valve 210 which has a lower forward pressure drop.

It has also been discovered that a flexure 228 which is anchored at both ends may be prestressed, i.e., that the flexure 228 may be under tension when the one-way membrane valve 210 is at its designed operating temperature, and when there is a zero driving pressure difference (P) across the one-way membrane valve 210. Such prestressing of the flexure 228 offers numerous advantages. For example, under a supposedly zero driving pressure difference (P) across the one-way membrane valve 210, the valve 210 may "bleed" the medication 12. It has been discovered that prestressing the flexure 228 may at least partially, if not totally, eliminate this potential problem because, due to the tension in the prestressed flexure 228, it takes a small, but not an insignificant, positive driving pressure difference across the one-way membrane valve 210, to cause the prestressed flexure 228 to unseat from the valve seat 220. Thus, the prestressed flexure 228 is much less likely to bleed the medication 12 under a supposedly zero driving pressure difference (P) across the one-way membrane valve 210. In addition, such a prestressed flexure 228 results in reducing, or even eliminating, any back flow of the medication 12 through the valve 210 when it is subjected to a negative driving pressure difference (P). Further, such prestressing of the flexure 228 enables the forward opening characteristics of the one-way membrane valve 210 to be "tuned". This is because as the amount of the tension in the prestressed flexure 228 is increased, the minimum positive driving pressure difference (P) across the one-way membrane valve 210 which is needed to unseat the flexure 228 from the valve seat 220 also increases (and vice versa). In addition, as the amount of tension in the prestressed flexure 228 is increased, the size of the inlet valve gap 234, and the flow rate (Q) of the medication 12 through the one-way membrane valve 210, for any given driving pressure difference (P) across the one-way membrane valve 210, will decrease (and vice versa).

It has also been discovered that, as a result of all of the forgoing considerations, the valve 210 offers the attractive advantages of increased uniformity and increased yield when mass produced, as compared to a valve 210 which has a less flexible flexure 228, which has a cantilevered flexure, or which has a rigid center boss.

It should be noted that, because the inlet and the outlet ports 216, 230 are located on opposite sides the one-way membrane valve 210, the valve 210 may be used either as a one-way inlet valve 210, or as a one-way outlet valve 210, merely by turning it over. For example, referring now to FIG. 20, the valve 210 may be substituted for the one-way inlet valve 134, 300 by mounting the valve 210 with its membrane 214 towards the pump 190's substrate 132; and the valve 210 may be substituted for the one-way outlet valve 137, 300 by mounting the valve 210 with its substrate 212 towards the pump 190's substrate 132.

It should also be noted that, if the valve 210 were mounted in its intended location of use so that the top surface of the flexure 228 was in close proximity to a flat surface, and so that at least some of the medication 12 exiting from one or more of the outlet ports 230 had to pass through the gap between the flat surface and the top surface of the flexure 228, then the flexure 228 and the flat surface would, in effect, operate as a flow regulator similar to the radial flow regulator 32 of FIGS. 1-2, to regulate the flow of the medication 12 from the valve 210. In such a case, the flat surface would act as a regulator seat, similar to the regulator seat 42; the flexure 228 would act as a regulator flexure, similar to the regulator flexure 36; and the gap between the flexure 228 and the flat surface would act as a regulator gap, similar to the regulator gap 48.

A mathematical model for the behavior of the one-way valve may be similar to the mathematical model set forth below for the one-way valve 240.

From the disclosures in this document, it is seen that it is possible to selectively design a one-way membrane valve 210 having any particular desired forward flow rate (Q) of the medication 12 as a function of the driving pressure difference (P) across the one-way membrane valve 210. This may be done by selectively adjusting one or more of the pertinent parameters, such as: (a) the stiffness, elasticity, resiliency, length, width, thickness, shape, cross-sectional configuration, and amount of prestressing of the flexure 228; (b) the number, size and shape of the inlet port 216, the inlet cavity 218, the inlet valve seat 220, the outlet cavity 224, and the outlet ports 224; and (c) the driving pressure difference (P) across the one-way membrane valve 210.

MICROMACHINED ONE-WAY MEMBRANE VALVE 210 HAVING A RECTANGULAR FLEXURE AND A RING-SHAPED INLET VALVE SEAT (FIGS. 23–25): MANUFACTURE

The one-way membrane valve 210's substrate 212 may be manufactured from any suitable strong, durable material which is compatible with the medication 12, and in which the inlet port 216, the inlet cavity 218 and the outlet cavity 224 may be manufactured in any suitable way, such as by using any suitable etching, molding, stamping and machining process. Such a machining process may include the use of physical tools, such as a drill or saw; the use of electromagnetic energy, such as a laser; and the use of a water jet.

The membrane 214 may be manufactured from any suitable strong, durable, flexible, material which is compatible with the medication 12, and in which the outlet ports 230 may be manufactured in any suitable way, such as by using any suitable etching, molding, stamping and machining process. Such a machining process may include the use of physical tools, such as a drill or saw; the use of electromagnetic energy, such as a laser; and the use of a water jet.

If the one-way membrane valve 210 is intended to be used with a medication 12 which is to be supplied to a human or an animal, then any part of the one-way membrane valve 210 which is exposed to the medication 12 should be manufactured from, and assembled or bonded with, non-toxic materials. Alternatively, any toxic material which is used to manufacture the one-way membrane valve 210, and which is exposed to the medication 12 during use of the one-way valve 210 may be provided with any suitable non-toxic coating which is compatible with the medication 12.

Suitable materials for the substrate 212 and the membrane 214 may be metals (such as titanium), glasses, ceramics, plastics, polymers (such as polyimides), elements (such as silicon), various chemical compounds (such as sapphire, and mica), and various composite materials.

The substrate 212 and the membrane 214 may be assembled together in any suitable leak-proof way. Alternatively, the substrate 212 and the membrane 214 may be bonded together in any suitable leak-proof way, such as by anodically bonding them together; such as by fusing them together (as by the use of heat or ultrasonic welding); and such as by using any suitable bonding materials, such as adhesive, glue, epoxy, solvents, glass solder, and metal solder.

Anodically bonding the substrate 212 and the membrane 214 together may be preferable for reasons which are the same as, or at least similar to, the reasons set forth above for anodically bonding the radial flow regulator 32's substrate 34 and membrane 36 together.

It has also been discovered that anodically bonding the substrate 212 and membrane 214 together may be desirable for at least two additional reasons. First, it has been discovered that the elevated temperatures which are used during the anodic bonding process may be used to automatically prestress the flexure 228. This will be discussed in more detail below.

Second, it has also been discovered that the elevated temperatures and voltages used during the anodic bonding process may be used to automatically cause the inlet valve seat 220 and the flexure 228 to conform to each other, thereby resulting in a better seal therebetween than might otherwise be the case. This is because such elevated temperatures during the anodic bonding process tend to soften the substrate 212, while such elevated voltages during the anodic bonding process tend to draw the softened substrate 212 and flexure 214 tightly together, thereby physically deforming the flexure 228 and the inlet valve seat 220 enough to "smooth out" to some degree any microscopic irregularities which may be present on the mating surfaces of the flexure 228 and the inlet valve seat 220.

One example of how the one-way membrane valve 210 may be manufactured will now be given. The starting point may be a 76.2 mm diameter wafer of Corning 7740 Pyrex glass, which will form the one-way membrane valve 210's substrate 212.

The inlet cavity 218 and the outlet cavity 224 may be manufactured in the substrate 212 in any suitable way. One suitable way may be to use an etching process which is the same as, or at least similar to, that used to form the radial flow regulator 32's inlet channels 38, inlet cavity 40, regulator seat 42 and outlet port 54 of FIGS. 1–2, except for those differences, if any, which will be made apparent by an examination of all of the Figures and disclosures in this document.

The inlet port 216 may then be formed in the substrate 212 in any suitable way. The structure, operation, theory and manufacture of the one-way membrane valve 210's inlet port 216 may be the same as, or at least similar to, those of the radial flow regulator 32's outlet port 54 of FIGS. 1–2, except for those differences, if any, which will be made apparent by an examination of all of the Figures and disclosures in this document.

Next, a nominal layer of one or more corrosion-resistant material substances may then be deposited onto all of the surfaces of the inlet port 216, the inlet cavity 218, the inlet valve seat 220, and the outlet cavity 224. The structure, operation, theory and manufacture of such a layer of one or more corrosion-resistant substances for the one-way membrane valve 210 may be the same as, or at least similar to, those of the layer of one or more corrosion-resistant substances for the radial flow regulator 32 of FIGS. 1–2, except for those differences, if any, which will be made apparent by an examination of all of the Figures and disclosures in this document.

It has been discovered that such a layer of corrosion-resistant substance(s) may serve at least one important function, in addition to its corrosion-resistant function, if the membrane 214 is anodically bonded to the substrate 212. That is, the layer of corrosion-resistant substance(s) may prevent the flexure 228 from being bonded to the inlet valve seat 220 during the anodic bonding process.

The membrane 214, with its outlet ports 230, may be manufactured from a silicon wafer, and secured to the glass wafer (which is the substrate 212) in any suitable way. The structure, operation, theory and manufacture of the one-way membrane valve 210's membrane 214, with its outlet ports 230, and the securing of the membrane 214 to its substrate 212 is the same as, or at least similar to, the manufacturing of the linear flow regulator 80's membrane 84, with its inlet port 88, and the securing of its membrane 84 to its substrate 86, except for those differences, if any, which will be made apparent by an examination of all of the Figures and disclosures in this document.

If it is desired to intentionally prestress the flexure 228, the flexure 228 may be prestressed in any suitable way. One suitable way may be to select materials for the substrate 212 and the membrane 214 which have different thermal expansion coefficients, such as a wafer of 7740 Pyrex glass for the substrate 212 and a wafer of silicon for the membrane 214, for example. Then, after the glass wafer (the substrate 212) has been etched, and the boron-doped layer of the silicon wafer has been etched, the glass and silicon wafers may be heated (or cooled) to a temperature which is higher than (or lower than) the designed operating temperature range of the one-way membrane valve 210. The glass and silicon wafers may then be secured together at that higher (or lower) temperature, in any suitable way. Then, when the one-way membrane valve 210 is returned to its designed operating temperature range, and the manufacture of the membrane 214, with its outlet ports 230, has been completed, the difference in the thermal expansion coefficients of the substrate 212 and the membrane 214 will cause the flexure 228 to be prestressed to the desired amount.

For example, if, as mentioned above, the substrate 212 and the membrane 214 were selected to be manufactured from 7740 Pyrex glass and silicon, respectively; and the substrate 212 and the membrane 214 may be bonded together by using anodic bonding at a temperature higher than the one-way membrane valve 210's designed operating temperature range, such as from about 300° C. to about 520° C.

The manufacture of only one one-way membrane valve 210 was described above. However, it will be appreciated that on any pair of glass and silicon wafers the substrates 212 and the membranes 214 for a large number of one-way membrane valves 210 could be manufactured simultaneously in a manner similar to that described above. If such is the case, an array of substrates 212 may be simultaneously etched in the glass wafer; their inlet ports 216 may be drilled, and the layer of one or more corrosion-resistant substances may be applied to the substrates 212. Then an array of outlet ports 230 may be simultaneously etched in the silicon wafer. Next, the silicon and glass wafers for the substrates 212 and the membranes 214 may be aligned and bonded together. Then, all of the membranes 214 may be formed simultaneously by grinding and etching the silicon wafer to its desired final thickness. The silicon/glass substrate 212/ membrane 214 sandwich may then be divided by any suitable means (such as dicing) into individual chips, each chip bearing at least one one-way membrane valve 210.

One of the advantages of using etching and anodic bonding processes to manufacture the one-way membrane valve 210, is that such processes enable high quality, very reliable, one-way membrane valves 210 to be mass produced in great numbers at a cost so low that the one-way membrane valves 210 may be considered to be disposable. Other advantages of using an anodic bonding process to bond the substrate 212 and the membrane 214 together were described in detail above, i.e., to prestress the flexure 228, and to conform the inlet valve seat 220 and the flexure 228 to each other, for a better seal therebetween.

Further, it should also be noted that the one-way membrane valve 210 is stunning in its simplicity since it has only two basic parts, i.e. its substrate 212 and its membrane 214; and since only one of its parts is a moving part, i.e., its flexure 228, which merely bows during operation of the one-way membrane valve 210. Further, because the raw materials from which the one-way membrane valve 210 may be manufactured may be very inexpensive, such as glass and silicon, the cost of the one-way membrane valve 210 may held to a very low level.

MICROMACHINED ONE-WAY MEMBRANE VALVE 240 HAVING A RECTANGULAR FLEXURE AND A RECTANGULAR INLET VALVE SEAT (FIGS. 26–29): STRUCTURE

Figure 26:
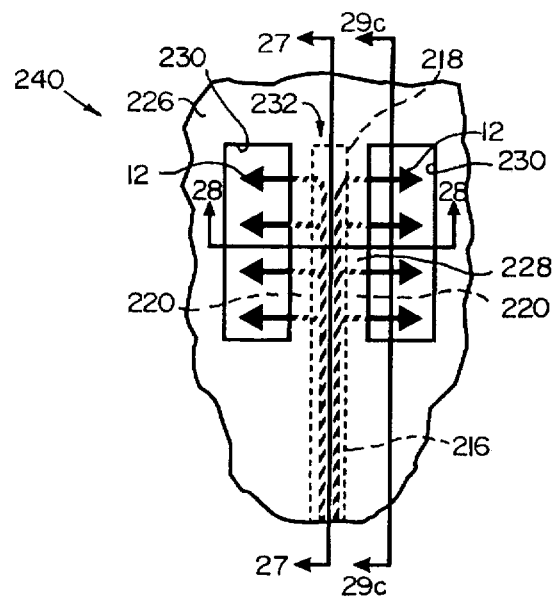
FIG. 26 is top plan view of a second embodiment of the micromachined one-way valve of the present invention.
Figure 27:
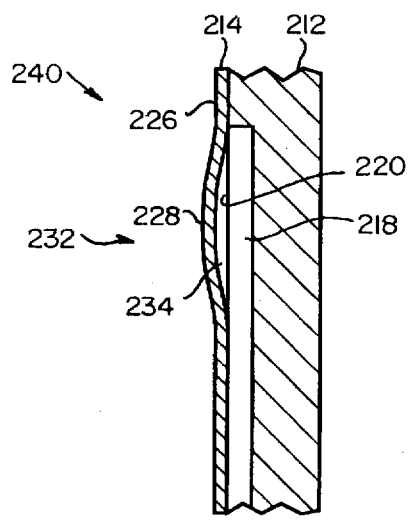
FIG. 27 is a cross-sectional view thereof, taken substantially along line 27—27 of FIG. 26.
Figure 28:
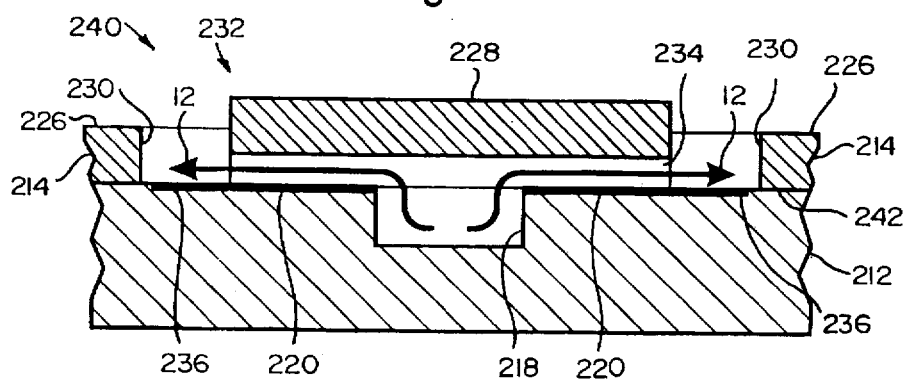
FIG. 28 is a cross-sectional view thereof, taken substantially along line 28—28 of FIG. 26.

The micromachined one-way membrane valve 240 which is illustrated in FIGS. 26–28 is the same as, or at least similar to, the micromachined one-way membrane valve 210 of FIGS. 23–25 in its structure, except for those differences which will be made apparent by an examination of all of the Figures and all of the disclosures in this document. Accordingly, the respective parts of the one-way membrane valve 240 have been given the same reference numerals as the corresponding parts of the one-way membrane valve 210 of FIGS. 23–25, for clarity and simplicity. Turning now to FIGS. 26–28, although a single inlet port 216 and a single inlet cavity 218 are illustrated, there may be more than one of each of these elements.

Although a rectangular inlet port 216, which is co-planar with the inlet cavity 218, is illustrated, the inlet port 216 may have any other suitable size and shape. In addition, the inlet port 216 may have any other suitable spatial relationship with respect to the inlet cavity 218. For example, the inlet port 216 may be transverse to the inlet cavity 218, and enter the inlet cavity 218 from below, rather than from one side.

Although a rectangular inlet cavity 218 having a uniform depth is illustrated, it may have any other suitable size and shape, and may have a non-uniform depth. In addition, the inlet port 216 may be eliminated, and the inlet cavity 218 may be extended so that it communicates directly with the substrate 212's outer surface and performs the functions of the inlet port 216. Alternatively, the inlet cavity 218 may be eliminated, and the inlet port 216 may be extended so that it performs the functions of the inlet cavity 218.

Although no outlet cavity 224 is illustrated, the one-way membrane valve 240 may be provided with an outlet cavity 224 which is the same as, or which is similar to, the one-way membrane valve 230's outlet cavity 224.

Although a pair of parallel, rectangular inlet valve seats 220 are illustrated, there may be fewer, or more, inlet valve seats 220, and each inlet valve seat 220 may have any other suitable size and shape.

By way of example, the one-way membrane valve 240 may have the following physical parameters. The substrate 212 may be made from 7740 Pyrex glass and have a thickness of about 0.5 mm. The inlet port 216 may have a width of about 0.5 mm and a depth of about 25 microns. The inlet cavity 218 may have a length of about 3.18 mm, a width of about 0.5 mm, and a depth of about 25 microns. Each inlet valve seat 220 may have a length of about 3.18 mm and a width of about 0.25 mm. The membrane 214 may be made from silicon, and may have a thickness of about 25.0 microns. The outlet ports 230 may each have a width of about 0.5 mm, and a length of about 3.18 mm. The flexure 228 may be about 25.0 microns thick, about 3.18 mm long, and about 1.0 mm wide.

Figure 29B:
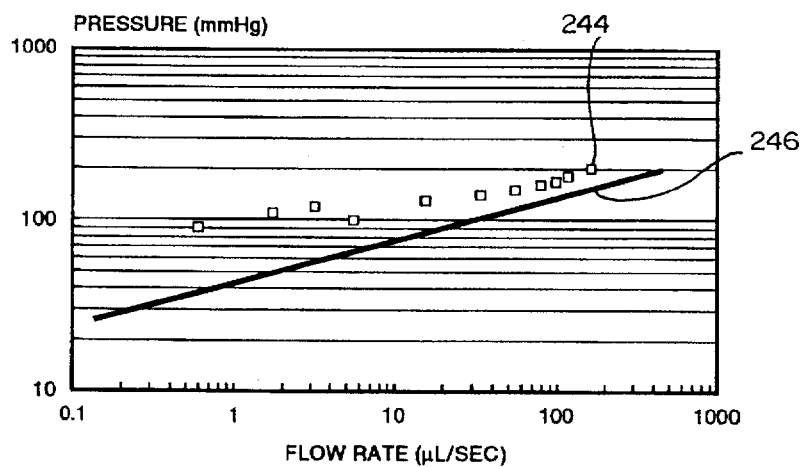
FIG. 29B is a graph depicting certain fluid flow characteristics of the second embodiment of the micromachined one-way valve of the present invention.
Figure 29C:
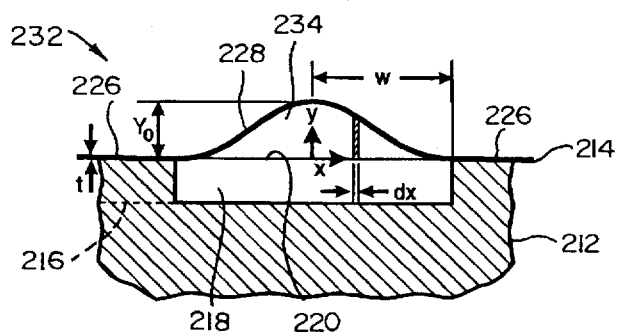
FIG. 29C is a schematic representation of certain factors used in a mathematical model thereof.

The flow characteristics of this example one-way membrane valve 240 are illustrated in FIG. 29B.

MICROMACHINED ONE-WAY MEMBRANE VALVE 240 HAVING A RECTANGULAR FLEXURE AND A RECTANGULAR INLET VALVE SEAT (FIGS. 26–29): OPERATION AND THEORY

The micromachined one-way membrane valve 240 which is illustrated in FIGS. 26–28 is the same as, or at least similar to, the micromachined one-way membrane valve 210 of FIGS. 23–25 in its operation and theory, except for those differences which will be made apparent by an examination of all of the Figures and all of the disclosures in this document.

During operation, as seen in FIGS. 27–28, if a positive driving pressure difference (P) is applied across the one-way membrane valve 240, such as by pressurizing the source of the medication 12 with respect to the one-way membrane valve 240's outlet ports 230, the pressure of the medication 12 beneath the flexure 228 will cause the flexure 228 to bow away from, and unseat from, the inlet valve seats 220. This will permit the medication 12 to flow in through the inlet port 216, and the inlet cavity 218; to flow outwardly through the valve gap 234 between the valve seats 220 and the flexure 228; and to flow out through the outlet ports 224.

On the other hand, if a negative driving pressure difference (P) is applied across the one-way membrane valve 240, such as by pressurizing the medication 12 adjacent to the top of the flexure 228 with respect to the inlet port 216, the pressure of the medication 12 on top of the flexure 228 will drive the flexure 228 towards, and seat it against, the inlet valve seats 220. This will prevent any back flow of the medication 12 of the inlet port 216.

Referring now to FIG. 29B, the eleven square data points 244 are for the measured flow rate (Q), in microliters per second, of the example one-way membrane valve 240, whose physical parameters were set forth above; as a function of the driving pressure difference (P) across the one-way membrane valve 210, in mm Hg. The medication 12 was distilled water at about 23° C. The solid line 246 shown in FIG. 29B is a plot of the predicted performance of the example one-way membrane valve 240, whose physical parameters were set forth above, under a performance theory which will be discussed below.

When the above example one-way membrane valve 240, whose physical parameters were set forth above, was tested in a reverse flow condition, the leak rate at 200 mm Hg was less than 0.00145 microliters/minute, which corresponds to a forward-to-reverse flow ratio in excess of 40,000:1 even if the designed forward flow rate was only about 1.0 microliter per second.

It should be noted that, if the valve 240 were mounted in its intended location of use so that the top surface of the flexure 228 was in close proximity to a flat surface, and so that at least some of the medication 12 exiting from one or more of the outlet ports 230 had to pass through the gap between the flat surface and the top surface of the flexure 228, then the flexure 228 and the flat surface would, in effect, operate as a flow regulator similar to the radial flow regulator 32 of FIGS. 1–2, to regulate the flow of the medication 12 from the valve 210. In such a case, the flat surface would act as a regulator seat, similar to the regulator seat 42; the flexure 228 would act as a regulator flexure, similar to the regulator flexure 36; and the gap between the flexure 228 and the flat surface would act as a regulator gap, similar to the regulator gap 48.

A mathematical model for the valve 240 will now be given. To predict the relationship between the flow rate (Q) of the medication 12 and the driving pressure difference (P) for the valve 240, the two dimensional coordinate system shown in FIG. 29C may be used. The origin (0,0) may be placed on the longitudinal axis of the inlet cavity 218, halfway along the flexure 228, in the plane of the top surface of the inlet valve seats 220.

It is assumed that the flexure 228 is curved only in the X-Y plane; that the flexure 228 is flat perpendicular to the X-Y plane; that all of the driving pressure difference (P) is dropped across the valve seats 220; that all other portions of the valve 240 have fluid pressures which are constant; and that each valve seat 220 is narrow compared to the total width of the flexure 228, i.e., has a width ratio of about 1:5, or less.

If movement of the flexure 228 is represented by the one-dimensional deflection of a thin, rectangular slab element which is subjected to a constant driving pressure difference (P) across its surface, within the area encompassed by the perimeter of the valve seat 220, and which is secured to the substrate 212 at both of its ends, then its deflection is given by above Equation 5, where $Y_0$ is the maximum deflection of the flexure 228 at x=0. The centerline deflection of the flexure 228 is given by above equation 5A, where the pressure difference $(p_s-p)$ in that equation is now replaced by the pressure drop across the inlet valve seat 220, ΔP.

To calculate the total flow rate (Q) of the medication 12 corresponding to this pressure drop, a differential fluid slice (dx) wide is used which spans the inlet valve gap 234. If the bowing or deflection of the flexure 228 is very slight, then it may be assumed that this local fluid slice has a negligible shear along its sides and is dominated by viscous drag at top and bottom. With this assumption, it may be found that the total flow rate (Q) per valve seat 220 is given by:

$$Q = \frac{\Delta P}{12\mu s} \int_{W}^{-W} Y_m^3(x) dx \qquad \text{Equation 8}$$

where s is the width of the inlet valve seat 220 and μ is the viscosity of the medication 12.

A similar approach may be used to calculate the flow characteristics of a valve with a circular valve seat (such as the valve 210), or a valve like the valve 210, but which has a square or rectangular valve seat 220. This would entail developing a deflection equation corresponding to the flexure 228's new pressure loading, as defined by the outline of its particular valve seat 220, and then integrating the above integral equation 8 around the perimeter of the inlet valve seat 220 to determine the total flow rate (Q) of the medication 12.

From the disclosures in this document, it is seen that it is possible to selectively design a one-way membrane valve 240 having any particular desired forward flow rate (Q) of the medication 12 as a function of the driving pressure difference (P) across the one-way membrane valve 240. This may be done by selectively adjusting one or more of the pertinent parameters, such as: (a) the stiffness, elasticity, resiliency, length, width, thickness, shape, cross-sectional configuration, and amount of prestressing of the flexure 228; (b) the number, size and shape of the inlet port 216, the inlet cavity 218, the inlet valve seat 220, the outlet cavity 224, and the outlet ports 224; and (c) the driving pressure difference (P) across the one-way membrane valve 210.

MICROMACHINED ONE-WAY MEMBRANE VALVE 240 HAVING A RECTANGULAR FLEXURE AND A RECTANGULAR INLET VALVE SEAT (FIGS. 26–29): MANUFACTURE

The micromachined one-way membrane valve 240 which is illustrated in FIGS. 26–28 is the same as, or at least similar to, the micromachined one-way membrane valve 210 of FIGS. 23-25 in its manufacture, except for those differences which will be made apparent by an examination of all of the Figures and all of the disclosures in this document.

The inlet port 216 and the inlet cavity 218 may be manufactured in the substrate 212 in any suitable way. One suitable way may be simultaneously etch them into the substrate 212 by using an etching process which is the same as, or at least similar to, that used to form the radial flow regulator 32's inlet channels 38, inlet cavity 40, regulator seat 42 and outlet port 54 of FIGS. 1–2, except for those differences, if any, which will be made apparent by an examination of all of the Figures and disclosures in this document.

MICROMACHINED ONE-WAY MEMBRANE VALVE 300 HAVING A CIRCULAR FLEXURE AND A CIRCULAR INLET VALVE SEAT (FIGS. 30–32): STRUCTURE

Figure 30:
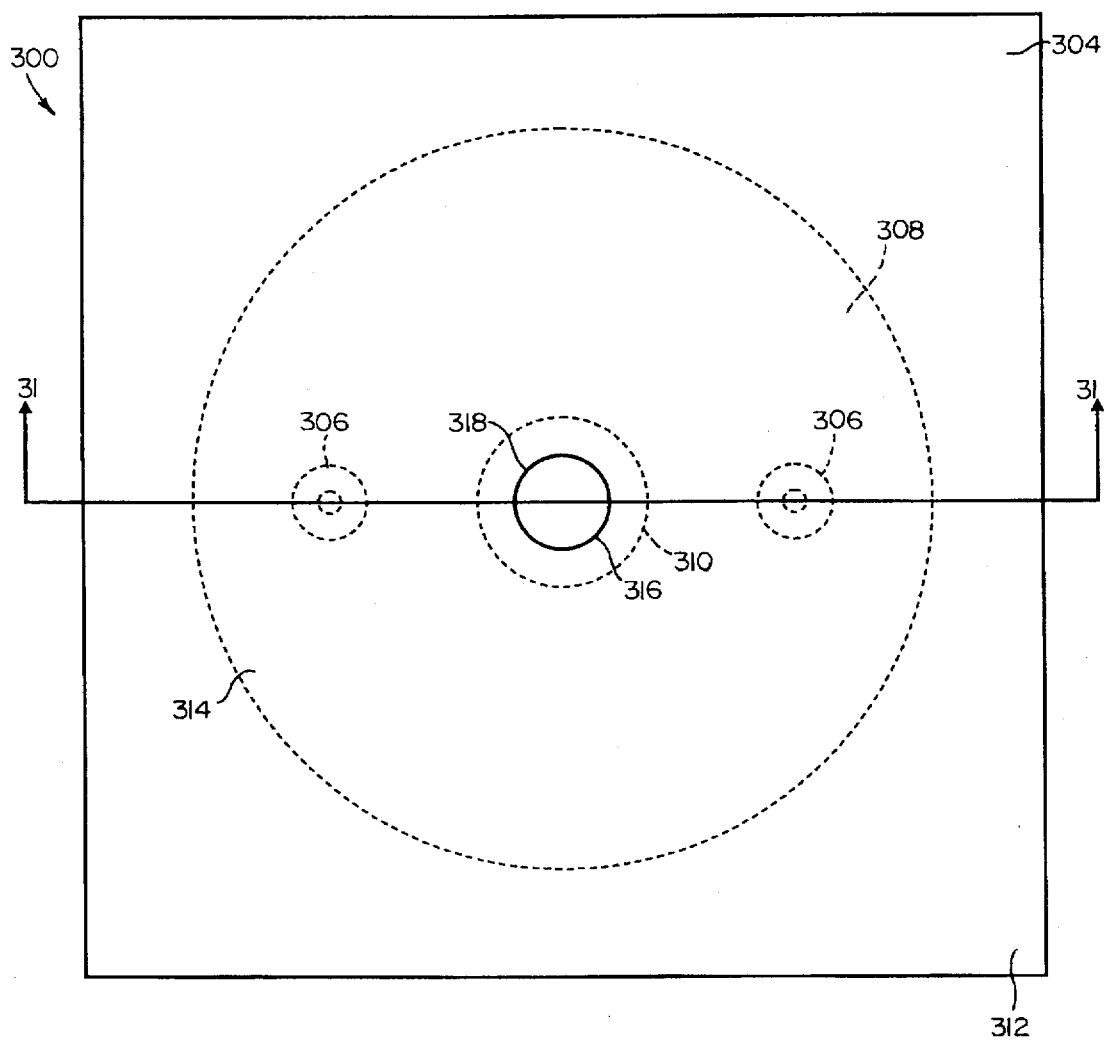
FIG. 30 is a top plan view of a third embodiment of the micromachined one-way valve of the present invention.
Figure 31:
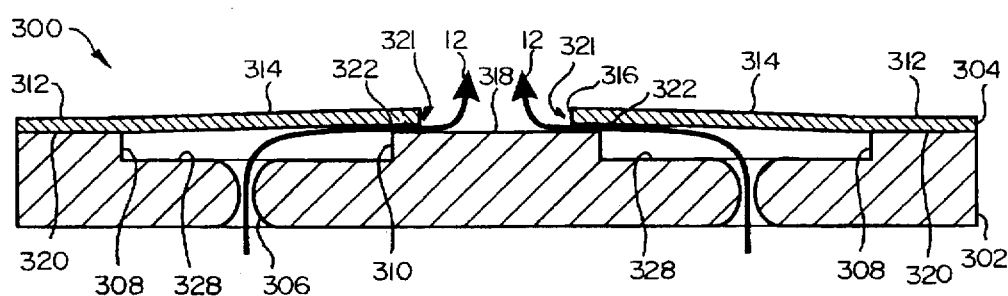
FIG. 31 is a cross-sectional view thereof, taken substantially along line 31—31 of FIG. 30.

The third embodiment of the micromachined one-way membrane valve 300 of the present invention is illustrated in FIGS. 30–31. The one-way membrane valve 300 may comprise a substrate 302 and a membrane 304.

The substrate 302 may have a pair of inlet ports 306; an inlet cavity 308; and an inlet valve seat 310.

Although a pair of inlet ports 306, having a venturi-shape for better fluid flow therethrough, are illustrated, there may be fewer or more inlet ports 306, and each inlet port 306 may have any other suitable size and shape. For example, the one-way membrane valves 300 illustrated in FIG. 21 have four inlet ports 306.

Although only one ring-shaped inlet cavity 308 is illustrated, there may be more than one inlet cavity 308, and each inlet cavity 308 may have any other suitable size and shape.

Although the inlet valve seat 310 is illustrated as being cylindrical, it may have any other suitable size and shape. Although the inlet valve seat 310's top surface 318 is preferably at least about 2.0 microns higher than the regulator 302's top surface 320, the inlet valve seat may be about the same height as, or lower than, the regulator 302's top surface 320.

The membrane 304 may have a mounting portion 312, which is secured to the substrate 302's top surface 320 outside of the inlet cavity 308; it may have a flexure portion 314, which is not secured to the substrate 302, and which extends over the inlet cavity 308 and over part of the inlet valve seat 310; and it may have an outlet port 316, which also overlies part of the inlet valve seat 310. Although the outlet port 316 is illustrated as being circular, it may have any other suitable size and shape.

By way of example, the one-way membrane valve 300 may have the following physical parameters. The one-way membrane valve 300 may be a square having sides about 5 mm long. The substrate 212 may be made from 7740 Pyrex glass and have a maximum thickness of about 0.5 mm. The inlet ports 306 may have a minimum diameter of about 100 microns and a length of about 475 microns. The inlet cavity 308 may have a maximum diameter of about 4.3 mm, and a depth of about 25 microns; the inlet valve seat may have a diameter of about 8.90 microns, and a height of about 27–29 microns. The membrane 304 may be made from epitaxial silicon, and may have a thickness of about 25 microns. The flexure 314 may have an outer diameter of about 4.3 mm. The flexure 314's outlet port 316 may have a diameter of about 500 microns.

MICROMACHINED ONE-WAY MEMBRANE VALVE 300 HAVING A CIRCULAR FLEXURE AND A CIRCULAR INLET VALVE SEAT (FIGS. 30–32): OPERATION AND THEORY

The one-way membrane valve 300 may be installed in its intended location of use in any suitable way. Any suitable medication supply means may be used to connect the one-way membrane valve 300's inlet ports 306 to a source of the medication 12; and any suitable medication delivery means may be used to connect the one-way membrane valve 300's outlet port 316 to whatever person, object or thing is to receive the medication 12 from the outlet port 316.

During operation, as seen in FIG. 31, if a positive driving pressure difference (P) is applied across the one-way membrane valve 300, such as by pressurizing the source of the medication 12 with respect to the one-way membrane valve 300's outlet port 316, the pressure of the medication 12 beneath the flexure 314 will cause the flexure 314 to bow away from, and unseat from, the inlet valve seat 310. This will permit the medication 12 to flow in through the inlet ports 306, and the inlet cavity 308; to flow radially inwardly through the inlet valve gap 321 between the inlet valve seat 310 and the flexure 314; and to flow out through the outlet port 316.

On the other hand, if a negative driving pressure difference (P) is applied across the one-way membrane valve 300, such as by pressurizing the medication 12 adjacent to the top of the flexure 314 with respect to the inlet ports 306, the pressure of the medication 12 on top of the flexure 314 will drive the flexure 314 towards, and seat it against, the inlet valve seat 310. This will prevent any back flow of the medication 12 through the inlet ports 306.

It has been discovered that if the valve 300 is manufactured so that the inlet valve seat 310's top surface 318 is coplanar with the substrate 302's top surface 320, then the normal, very small variations in the flatness of the inlet valve seat 310's top surface 318, and in the flatness of the flexure 314's bottom surface 322 (hereinafter termed "co-planar flatness variations"), may give rise to at least four potential problems.

However, it has also been discovered that if the inlet valve seat 310 is made so that its top surface 318 is slightly higher than the substrate 302's top surface 320 (on the order of at least about 2 microns, for example), then the flexure 314 will be prestressed. By "prestressed", it is meant that the height difference between the top surface 318 of the inlet valve seat 310 and the top surface 320 of the substrate 302 causes the flexure 314 to be pressed against the inlet valve seat 220 when the one-way membrane valve 310 is at its designed operating temperature, and when there is a zero driving pressure difference (P) across the one-way membrane valve 300. It has also been discovered that the amount of such prestressing of the flexure 314 is a function of such height difference, with the amount of such prestressing of the flexure 314 increasing as the height difference increases (and vice versa).

It has been discovered that by prestressing the flexure 314, all four of the potential problems caused by co-planar flatness variations may be at least partially, or even completely, eliminated.

The first potential problem caused by such co-planar flatness variations is that there may be undesirable back flow of the medication 12 through the valve 300 when there is a negative driving pressure difference (P) across the one-way membrane valve 300. Such back flow of the medication 12 may render the one-way membrane valve 300 unfit for use where such back flow cannot be tolerated in the particular intended use for the one-way membrane valve 300. For example, if the one-way membrane valve 300 was to be used in a medication delivery apparatus, such back flow might permit blood, or other body fluids, to flow back into the one-way membrane valve 300, and clog it.

However, it has been discovered that prestressing the flexure 314 may reduce, or even eliminate, any back flow of the medication 12 through the one-way membrane valve 300 when there is a negative (reverse) driving pressure difference (P) across the one-way membrane valve 300. This is because prestressing the flexure 314 may physically deform the flexure 314 and the inlet valve seat 310 enough to "smooth out" to some degree any microscopic irregularities which may be present on the mating surfaces of the flexure 314 and the inlet valve seat 310; thereby improving the conformity, and thus the sealing, between the flexure 314 and the inlet valve seat 310. Such improved conformity and sealing between the flexure 314 and the inlet valve seat 310 may greatly reduce, if not eliminate, any back flow of the medication 12 when there is a negative (reverse) driving pressure difference (P) across the one-way membrane valve 300.

In addition, it has also been discovered that prestressing the flexure 314 may reduce, or even eliminate, any back flow of the medication 12 through the one-way membrane valve 300 for the additional reason that the prestressed flexure 314 may tend to automatically seat against the inlet valve seat 310 when there is still a small positive driving pressure difference (P) across the one-way membrane valve 300. Thus, it is very unlikely that there may be any back flow of the medication 12 through the one-way membrane valve 300 as the driving pressure difference (P) is changing from positive to negative.

The second potential problem caused by such co-planar flatness variations is that the forward flow rate (Q) of the medication 12 through the one-way membrane valve 300, as a function of the driving pressure difference (P) of the medication 12 across the one-way membrane valve 300, may differ from valve 300 to valve 300, even if a group of valves 300 is supposedly manufactured to have identical physical parameters. Such differing forward flow characteristics may make certain one-way membrane valves 300 defective for their intended use, or may increase the cost of the one-way membrane valves 300 because each one must be tested in order to determine its actual forward flow rate (Q) characteristic curve. However, it has been discovered that prestressing the flexures 314 may at least partially, if not totally, eliminate this potential problem by making all of the one-way membrane valves 300 which are manufactured identically to have more nearly identical forward flow rates (Q) of the medication 12, as a function of the driving pressure difference (P) of the medication 12 across the one-way membrane valves 300.

The third potential problem caused by such co-planar flatness variations is that under a supposedly zero driving pressure difference (P) across the one-way membrane valve 300, the valve 300 may "bleed" the medication 12. It has been discovered that prestressing the flexures 314 may at least partially, if not totally, eliminate this potential problem because, due to the tension in the prestressed flexure 314, it takes a small, but not an insignificant, positive driving pressure difference across the one-way membrane valve 300, to cause the prestressed flexure 314 to unseat from the valve seat 300. Thus, the prestressed flexure 314 is much less likely to bleed the medication 12 under a supposedly zero driving pressure difference (P) across the one-way membrane valve 300.

The fourth potential problem caused by such co-planar flatness variations is that it may be difficult, if not impossible to accurately "tune" the forward opening characteristics of the one-way membrane valve 300. However, it has been discovered that prestressing the flexure 314 may at least partially, if not totally, eliminate this potential problem because as the amount of the tension in the prestressed flexure 314 is increased, the minimum positive driving pressure difference (P) across the one-way membrane valve 300 which is needed to unseat the flexure 314 from the valve seat 310 also increases (and vice versa). In addition, as the amount of tension in the prestressed flexure 314 is increased, the size of the inlet valve gap 321, and the flow rate (Q) of the medication 12 through the one-way membrane valve 300, for any given driving pressure difference (P) across the one-way membrane valve 300, will decrease (and vice versa). Thus, these factors make it clear that the forward opening characteristics of the one-way membrane valve 300 may be "tuned" by selecting the amount of the tension by which the flexure 314 is prestressed.

It has been further discovered that, as a result of all of the forgoing, such prestressing of the flexure 314 results in a yield approaching 100%, regarding the number of useable one-way membrane valves 300 which are obtained during the manufacture of the one-way membrane valves 300. On the other hand, if the flexure 314 is not prestressed, then as many as about 50%–75% of the valves 300 may be unusable, primarily because of buckling of the flexure 314, due to compressive loading, rather than tensile loading, on the flexure 314. Such buckling of the flexure 314 may render the valve 300 unusable, since it may "bleed" under a nominally zero driving pressure difference (P) across the valve 300, and since the valve 300 may leak when subjected to a negative driving pressure difference (P).

However, even though it may be desirable that the inlet valve seat's top surface 318 is higher than the top surface 320 of the rest of the substrate 302, so that the flexure 310 may be prestressed, such a height difference may interfere with properly securing the membrane 304's mounting portion 312 to the substrate's top surface 320.

Nevertheless, it has been discovered that if suitable materials are selected for the substrate 302 and the membrane 304; if the membrane 304 is formed from a wafer of material which is not reduced to its final thickness until after the substrate 302 and the membrane 304 are secured together; and if the ratio of the inlet cavity 308's maximum diameter to the inlet valve seat 310's height above the inlet cavity 308's bottom 328 is appropriately selected, then anodic bonding may be used to successfully secure the membrane 304 to the substrate 302, despite such a height difference between the top surfaces 318, 320 of the inlet valve seat 310 and the substrate 302.

This is apparently because at the elevated bonding temperatures used during the anodic bonding, the substrate 302 may be relatively elastic, while the membrane 304's wafer may be relatively stiff, or non-elastic. This may permit the relatively stiff membrane 304's wafer to elastically compress the inlet valve seat 310, due to the electrostatic forces that pull the substrate 302 and the membrane 304's wafer together during the anodic bonding process. Then, after the anodic bonding process is complete, and after the membrane 304's wafer has been reduced to its final thickness, the compressed inlet valve seat 310 will rebound to its original, uncompressed condition, thereby automatically restoring the desired height difference between the top surfaces 318, 320 of the inlet valve seat 310 and the substrate 302. This final result may also occur, of course, if both of the wafers for the substrate 302 and the membrane 304 elastically deform during the anodic bonding process. However, if wafers of 7740 Pyrex glass and silicon are used, for example, the majority of the deformation occurs in the lower melting point 7740 Pyrex glass.

Suitable materials for the substrate 302 and the membrane 304 may be 7740 Pyrex glass and silicon, respectively; a suitable anodic bonding temperature may be about 500° C.; and a suitable ratio of the inlet cavity 308's maximum diameter to the inlet valve seat 310's height above the inlet cavity 308's bottom 328 may be at least about 100:1 and preferably about 1000:1. The suitable anodic bonding temperature, and the suitable ratio of the inlet cavity 308's maximum diameter to the inlet valve seat 310's height above the inlet cavity 308's bottom 328 may vary, depending what materials are selected to form the substrate 302 and the membrane 304.

Figure 32:
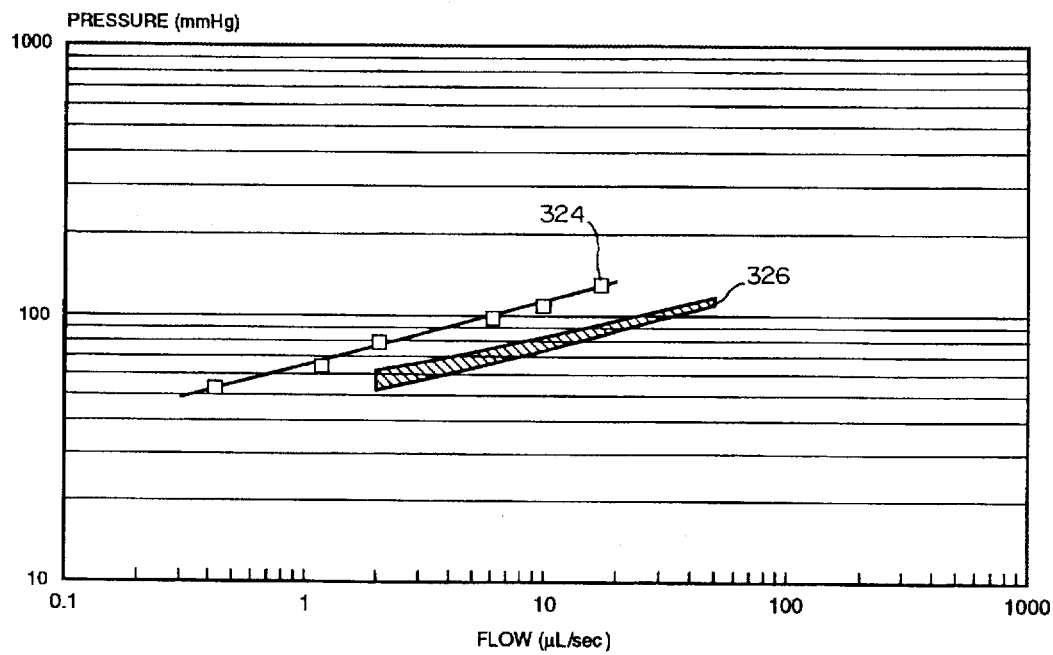
FIG. 32 is a graph depicting certain fluid flow characteristics thereof.
Figure 33:
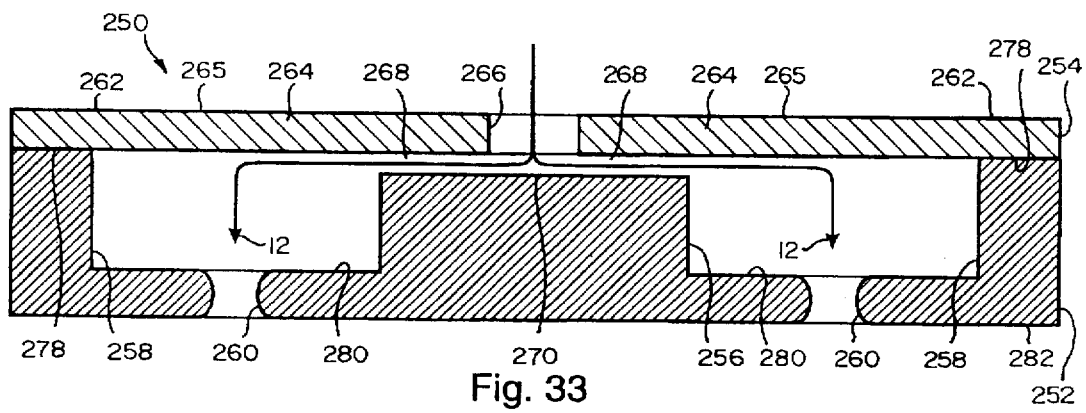
FIG. 33 is a cross-sectional view of the micromachined membrane flow switch 250 of the present invention, taken substantially along line 33—33 of FIG. 34.
Figure 34:
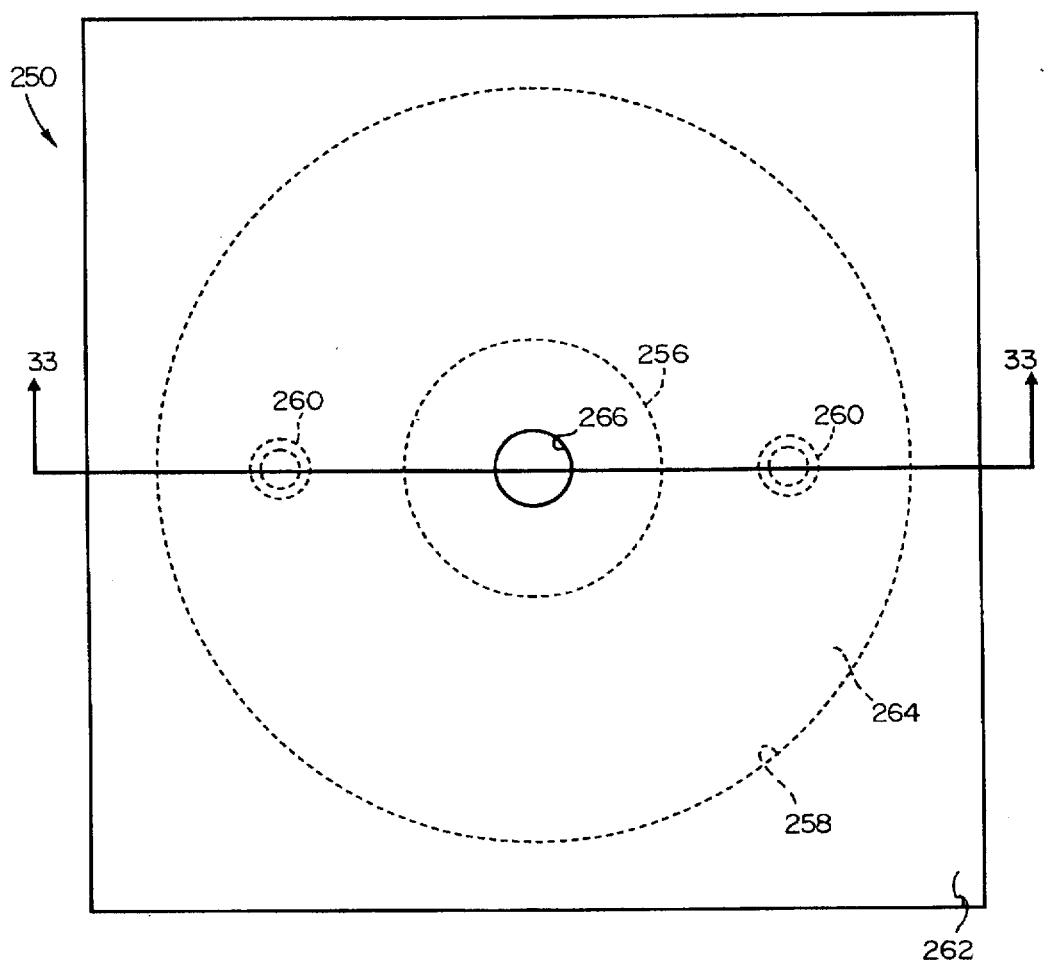
FIG. 34 is a top elevational view thereof.

Referring now to FIG. 32, the six square data points 324 are for the measured flow rate (Q), in microliters per second, of the medication 12 through the example one-way membrane valve 300, whose physical parameters were set forth above; as a function of the driving pressure difference (P), in mm Hg, across the one-way membrane valve 300. The medication 12 was distilled water at about 23° C. The cross-hatched band 326 shown in FIG. 32 is a plot of the predicted performance of the example one-way membrane valve 300, whose physical parameters were set forth above, under a performance theory which will be discussed below. A theoretical band 326 is plotted in FIG. 32, rather than a single line 326, because the band 326 represents a height difference, between the top surface 318 of the inlet valve seat 310 and the top surface 320 of the substrate 302, which ranges from about 2.0 microns to about 4.0 microns.

When the above example one-way membrane valve 300, whose physical parameters were set forth above, was tested in a reverse flow condition, the leak rate at 87.0 mm Hg was less than about 0.01 microliters/second, which corresponds to a forward-to-reverse flow ratio in excess of 200:1.

It should be noted that, as seen in FIG. 30, because the inlet and the outlet ports 306, 316 are located on opposite sides the one-way membrane valve 300, the valve 300 may be used either as a one-way inlet valve 300, or as a one-way outlet valve 300, merely by turning it over.

It should also be noted that, if the valve 300 were mounted in its intended location of use so that the top surface of the flexure 314 was in close proximity to a flat surface, and so that at least some of the medication 12 exiting from the outlet port 316 had to pass through the gap between the flat surface and the top surface of the flexure 314, then the flexure 314 and the flat surface would, in effect, operate as a flow regulator similar to the radial flow regulator 32 of FIGS. 1-2, to regulate the flow of the medication 12 from the valve 300. In such a case, the flat surface would act as a regulator seat, similar to the regulator seat 42; the flexure 314 would act as a regulator flexure, similar to the regulator flexure 36; and the gap between the flexure 314 and the flat surface would act as a regulator gap, similar to the regulator gap 48.

From the disclosures in this document, it is seen that it is possible to selectively design a one-way membrane valve 300 having any particular desired forward flow rate (Q) of the medication 12 as a function of the driving pressure difference (P) across the one-way membrane valve 300. This may be done by selectively adjusting one or more of the pertinent parameters, such as: (a) the stiffness, elasticity, resiliency, width, thickness, shape, and cross-sectional configuration of the flexure 314; (b) the amount the flexure 314 is prestressed, i.e., the height difference between the inlet valve seat 310's top surface 318 and the substrate 302's top surface 320; (c) the number size and shape of the inlet ports 306, the inlet cavity 308, and the outlet port 316; and (d) the driving pressure difference (P) across the one-way membrane valve 300.

MICROMACHINED ONE-WAY MEMBRANE VALVE 300 HAVING A CIRCULAR FLEXURE AND A CIRCULAR INLET VALVE SEAT (FIGS. 30–32): MANUFACTURE

The micromachined one-way membrane valve 300 which is illustrated in FIGS. 30–31 is the same as, or at least similar to, the micromachined one-way membrane valves 210, 240 of FIGS. 23–29 in its manufacture, except for those differences which will be made apparent by an examination of all of the Figures and all of the disclosures in this document.

Among those differences are that the desired height difference between the top surfaces 318, 320 of the inlet valve seat 310 and the substrate 302, respectively, may be obtained in any suitable way. One suitable way may be, before the membrane 304 is manufactured and secured to the substrate 302, to etch all of the substrate 302's top surface 320 (except for the inlet cavity 308 and the inlet valve seat 310), by an amount which is equal to the desired height difference. This etching step may be done in any suitable way, such as by using etching processes which is the same as, or at least similar to, that used to form the radial flow regulator 32's inlet channels 38, inlet cavity 40, regulator seat 42 and outlet port 54 of FIGS. 1-2, except for those differences, if any, which will be made apparent by an examination of all of the Figures and disclosures in this document.

Alternatively, the desired height difference may be obtained by depositing or securing, in any suitable way, a layer of any suitable material of the desired thickness on only the inlet valve seat 310's top surface 318.

MICROMACHINED MEMBRANE FLOW SWITCH 250 (FIGS. 33–38): STRUCTURE

The micromachined membrane flow switch 250 of the present invention is illustrated in FIGS. 33–38. The flow switch 250 may comprise a substrate 252 and a membrane 254.

The substrate 252 may have an inlet switch seat 256, an outlet cavity 258 and a pair of outlet ports 260.

Although the substrate 252 is illustrated as being square, it may have any other suitable size and shape.

Although the inlet switch seat 256 is illustrated as being cylindrical, and as having a flat top surface 270, it may have any other suitable size and shape; and its top surface 270 may not be flat.

Although a single, cylindrical, ring-shaped outlet cavity 258 is illustrated, there could be more than one outlet cavity 258, and each outlet cavity 258 could have any other suitable size and shape.

Although a pair of outlet ports 260, each having a venturi-shaped geometric configuration, for better fluid flow therethrough, are illustrated; there may be fewer or more outlet ports 260, and each outlet port 260 may have any other suitable size and shape.

The flow switch 250's membrane 254 may have a mounting portion 262, which may be secured to the substrate 252; a flexure 264, which extends over the outlet cavity and part of the inlet switch seat 256; and an inlet port 266, which lies over the inlet switch seat 256.

Although the flexure 264 is illustrated as being ring shaped, and as having a uniform thickness, it may have any other suitable size and shape, and its thickness may not be uniform.

Although one, circular inlet port 266 is illustrated, there may be more than one inlet port 266, and each inlet port 266 may have any other suitable size and shape.

A switch gap 268 may be defined between the inlet switch seat 256 and the flexure 264 when there is a zero driving pressure difference (P) of the medication 12 across the flow switch 250, which is the driving pressure difference (P) between the flexure 264's top surface 265 and the outlet ports 260.

By way of example, the flow switch 250 may have the following physical parameters. The substrate 252 may be made from 7740 Pyrex glass, may be a square having sides about 5.0 mm long, and may have a maximum thickness of about 0.5 mm. The outlet cavity 258 may have an inner diameter of about 2.0 mm, an outer diameter of about 3.8 mm, and a depth of about 25 microns as measured from the substrate 252's top surface 278. The outlet ports 260 may have a minimum diameter of about 100 microns, and a length of about 475 microns. The inlet switch seat 256 may have a diameter of about 2.0 mm, and a height above the outlet cavity 258's bottom surface 280 of about 21 microns. The switch gap 268 may be about 4 microns high, when there is a zero driving pressure difference (P) of the medication 12 across the flow switch 250. The membrane 254 may be made from epitaxial silicon, may have a thickness of about 25 microns, and may be a square having sides about 5.0 mm long. The flexure 264 may have an inner diameter of about 250 microns, and an outer diameter of about 3.8 mm. The inlet port 266 may have a diameter of about 250 microns.

The flow characteristics of this example flow switch 250 are illustrated in the graphs of FIGS. 35-38.

MICROMACHINED MEMBRANE FLOW SWITCH 250 (FIGS. 33-38): OPERATION AND THEORY

The flow switch 250 may be installed in its intended location of use in any suitable way. Any suitable medication supply means may be used to connect the flexure 264's top surface 265 and the inlet port 266 to a source of the medication 12; and any suitable medication delivery means may be used to connect the flow switch 250's outlet ports 260 to whatever person, object or thing is to receive the medication 12 from the outlet ports 260.

For example, the flow switch 250 may be installed within any type of reservoir means for the medication 12 by any suitable means, such as by locating the flow switch 250's outlet ports 260 over the reservoir means's outlet, and by using an adhesive face seal between the flow switch 250's bottom surface 282 and the inside of the reservoir means to hold the flow switch 250 in place. As a result, when the reservoir means is filled with the medication 12, the flow switch 250 may be immersed in the medication 12, with its inlet channel 266 and its flexure 264's top surface 265 in fluid communication with the medication 12 within the reservoir means, and with its outlet ports 260 in fluid communication with the reservoir means' outlet. Such an installation for the flow switch 250 may have numerous advantages.

For example, it is quick, easy, reliable and inexpensive, because no additional medication supply means (such as supply conduits) are needed to supply the medication 12 to the inlet port 266 and the flexure 264's top surface 265 (since they are already immersed in the medication 12); and because no additional medication delivery means (such as delivery conduits) are needed to convey the medication 12 away from flow switch 250's outlet ports 260, (since the reservoir means' outlet is used for this purpose). Such additional inlet and outlet conduits may be undesirable since it may be relatively time consuming, difficult and expensive to align and connect them to the flow switch 250, due to the extremely small size of the flexure 264, the inlet port 266, and the outlet ports 260. Such additional inlet conduits may also be undesirable because they may tend to trap a bubble when being filled with a liquid medication 12, which bubble might then be carried into the flow switch 250 and cause it to malfunction.

When there is a zero driving pressure difference (P) of the medication 12 across the flow switch 250, the flexure 264 is not bowed by the medication 12, and is essentially parallel to the inlet switch seat 256's top surface 270.

However, during operation of the flow switch 250, as a driving pressure difference (P) of the medication 12 is applied across the flow switch 250, such as by pressurizing the source of the medication 12 with respect to the flow switch 250's outlet port 260, by any suitable means, the medication 12 flows through the inlet port 266; flows radially outwardly across the inlet valve seat 256's top surface 270 through the switch gap 268; flows through the outlet cavity 258; and flows out through the outlet ports 260.

As the driving pressure difference (P) of the medication 12 across the flow switch 250 is increased from zero, the medication 12 gradually forces the flexure 264 closer to the switch seat 268, thereby gradually decreasing the height of the switch gap 268 (and vice versa).

Then, at a predetermined overpressure of the medication 12, i.e., at a predetermined driving pressure difference switch point ($P_{SW}$), the flexure 264 automatically begins an irreversible collapse that results in the flexure 264 being forced by the medication 12 against the inlet switch seat 256, and being held there by the medication 12, thereby automatically closing the switch gap 268, switching off the flow switch 250, and stopping the flow of the medication 12 through the flow switch 250.

Then, when the driving pressure difference (P) across the flow switch 250 is decreased to less than the predetermined overpressure, i.e., is decreased to less than the predetermined driving pressure difference switch point ($P_{SW}$), the resiliency and elasticity of the flexure 264 cause it to automatically move away from the inlet switch seat 256, thereby automatically opening the switch gap 268, switching the flow switch 250 back on, and permitting the medication 12 to flow through the flow switch 250 once again.

As a result, it is seen that, at a predetermined overpressure of the medication 12, i.e., at a predetermined driving pressure difference switch point ($P_{SW}$), the flow switch 250 is automatically switched off, thereby stopping the flow of the medication 12 through the flow switch 250; and that the flow switch 250 will not switch on again and permit the medication 12 to flow through the flow switch 250 again until the overpressure condition is remedied i.e., until the driving pressure difference (P) is decreased to less than the driving pressure difference switch point ($P_{SW}$).

Figure 35:
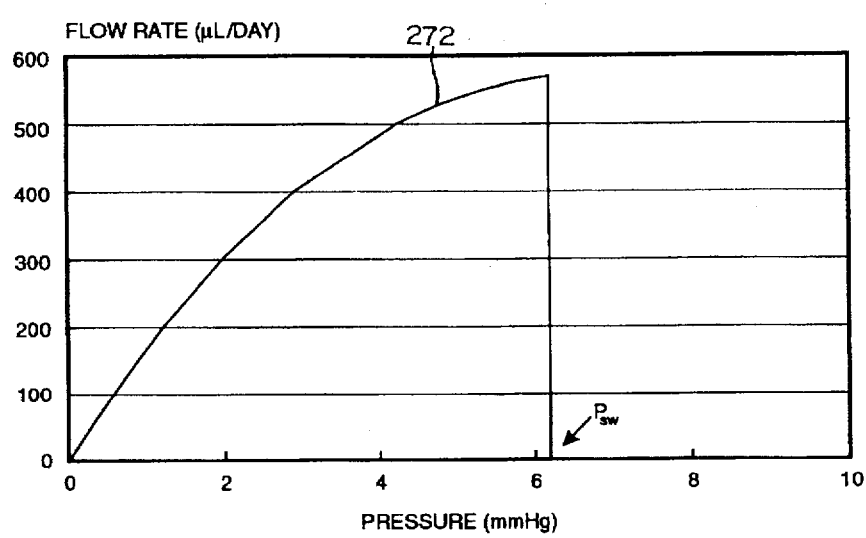
FIGS. 35–38 are graphs depicting certain fluid flow characteristics thereof.

The above operation of the flow switch 250 is illustrated in the graph of FIG. 35, whose flow curve 272 is for the example flow switch 250 having the physical parameters that were set forth above. As seen in FIG. 35, the flow rate (Q) of the medication 12 through the flow switch 250 increases as a function of the driving pressure difference (P) across the flow switch 250, up to the predetermined driving pressure difference switch point ($P_{SW}$) of about 6.2 mm Hg. At the predetermined driving pressure difference switch point ($P_{SW}$) of about 6.2 mm Hg, the flow switch 250 automatically switches off, and the flow rate (Q) drops to zero as the flexure 264 is forced against the inlet switch seat 256, and held there, by the medication 12. When the flow switch 250 has switched off, a high static pressure will occur across the switch 250, since it is now the primary resistance to the flow of the medication 12.

Another way of interpreting the flow curve 272 is that as the flow rate (Q) of the medication 12 through the flow switch 250 increases, the driving pressure difference (P) across the flow switch 250 increases as a function of the flow rate (Q), up to a predetermined flow rate switch point ($Q_{SW}$) of about 575 µL/day. At the predetermined flow rate switch point ($Q_{SW}$) of about 575 µL/day, the flow switch 250 automatically switches off, and the flow rate (Q) drops to zero as the flexure 264 is forced against the inlet switch seat 256, and held there, by the medication 12.

The type of response curve 272 shown in FIG. 35 is highly desirable for many applications where, if the flow rate (Q) or the driving pressure difference (P) of the medication 12 exceeds a predetermined nominal limit, such as due to an overpressure in the supply of the medication 12, there may be undesirable consequences.

For example, if the outlet for a reservoir in a medication delivery device for the medication 12 was equipped with a flow switch 250, then medication delivery device may be designed for nominal operation below a predetermined flow rate switch point ($Q_{SW}$), or below a predetermined driving pressure difference switch point ($P_{SW}$). Then, if either the predetermined medication flow rate switch point ($Q_{SW}$) or the predetermined driving pressure difference switch point ($P_{SW}$) is exceeded, such as if a medical person accidentally overfilled the medication delivery device's reservoir, the flow switch 250 would switch off the flow of the medication 12 from the medication delivery device until the excessive driving pressure difference (P) was rectified. That would significantly reduce the possibility of injury or death to the patient due to an overdose of the medication 12 which might otherwise occur.

Figure 36:
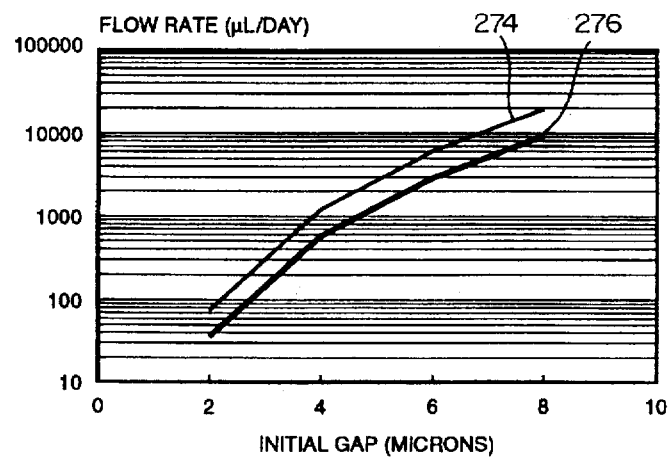
Figure 37:
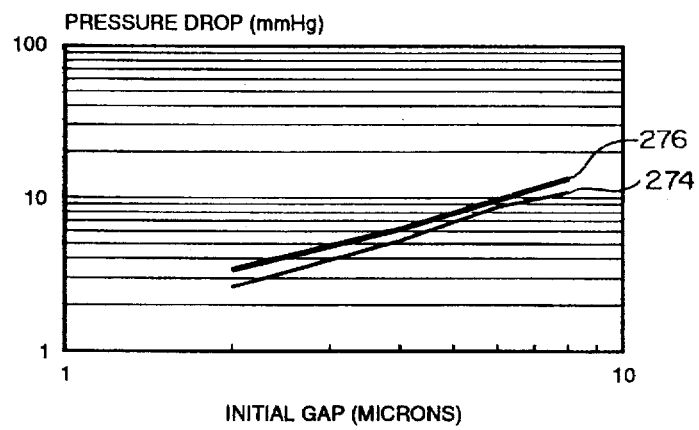
Figure 38:
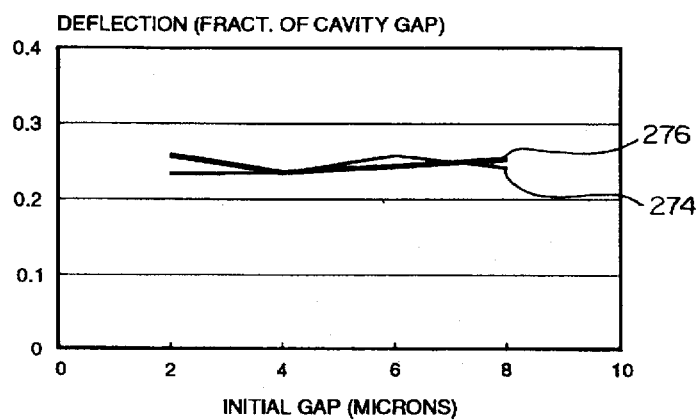

Referring now to the graphs of FIGS. 36–38, the thin plotted line 274 in each graph is for the example flow switch 250, having the physical parameters set forth above, except that its initial switch gap (at a zero driving pressure difference (P) across the flow switch 250), is as indicated on the horizontal axis. The thick plotted line 276 in FIGS. 36–38 is for the example flow switch 250, having the physical parameters set forth above, except that its inlet switch seat 256 has a diameter of 0.5 mm, and its initial switch gap (at a zero driving pressure difference (P) across the flow switch 250), is as indicated on the horizontal axis.

In FIG. 36, the lines 274, 276 are the plots of the flow rate switch points ($Q_{SW}$) for the flow switches 250 as a function of the initial switch gap 268 (at a zero driving pressure difference (P) across the flow switch 250). As seen in FIG. 36, the flow rate switch points ($Q_{SW}$) for the flow switches 250 are primarily set by the initial switch gap 268; but that the diameter of the inlet switch seat 256 is also significant, even though not as important.

FIG. 37 shows the driving pressure difference switch point ($P_{SW}$) for the flow switches 250 as a function of the initial switch gap 268 (at a zero driving pressure difference (P) across the flow switch 250). As seen in FIG. 37, the driving pressure difference switch points ($P_{SW}$) for the flow switches 250 are primarily set by the initial switch gap 268; but that the diameter of the inlet switch seat 256 is also significant, even though not as important.

FIG. 38 shows the switch point deflection of the flexure 264 at its inlet port 266 ($D_{SW}$) for the flow switches 250 as a function of the initial switch gap 268 (at a zero driving pressure difference (P) across the flow switch 250). The switch point deflection ($D_{SW}$) is measured as a fraction of the initial switch gap 268 (at a zero driving pressure difference (P) across the flexure 264). As seen in FIG. 38, the switch point deflection ($D_{SW}$) is relatively constant over a range of values for the initial switch gap 268.

The theory of operation of the flow switch 250, with its flow of the medication 12 through its switch gap 268 between its inlet switch seat 256 and its flexure 264, is similar to the theory of operation set forth above regarding the radial flow regulator 32 of FIGS. 1–2, and the flow of the medication 12 through its regulator gap 48 between its regulator seat 42 and its flexure 28, except for those differences which will be made apparent by an examination of all of the Figures and all of the disclosures in this document.

For example, the curvature boundary conditions on the flexure 264 differ from the curvature boundary conditions on the flexure 28, due to the flexure 264's inlet port 266.

In addition, the switch action of the flow switch 250's flexure 264 may be attributable to the destabilization of the flexure 264 caused by at least two things acting in concert. First, the destabilization of the flexure 264 may be caused by the fact that the outlet cavity 258 is at one of the lowest pressures in the flow switch 250. Since the flexure 264's incremental face area over the outlet cavity 258 is a function of the square of the radius of the flexure 264, the flexure 264's incremental face area is the greatest over the outlet cavity 258. Thus, there is a destabilizing leverage action exerted by the medication 12 on the flexure 264 due to the driving pressure difference of the medication 12 between the flexure's top surface 265 and the inside of the outlet cavity 258. Second, the destabilization of the flexure 264 may also be assisted by the free rim of the flexure's inlet hole 266, which helps to permit the flexure 264 to change its position and snap against the inlet switch seat 256. On the other hand, in the radial flow regulator 32 the medication 12 is at a relatively higher pressure in the inlet channels 38 and in the inlet cavity 40, as compared to the pressure of the medication in the regulator gap 48 and the outlet cavity 52, where the incremental face area of the flexure 28 is the least. So the regulator 32's flexure 28 tends to not exhibit the snap action of the flow switch 250's flexure 264.

From the disclosures in this document, it is possible to selectively design a flow switch 250 having any particular desired characteristic curve 272, 274, or 276; having any desired predetermined flow rate switch point rate ($Q_{SW}$) for the medication 12; and having any desired predetermined driving pressure difference switch point ($P_{SW}$) for the medication 12. This may be done by selectively adjusting one or more of the pertinent parameters, such as: (a) the stiffness, elasticity, resiliency, thickness, size and shape of the flexure 264; (b) the number, size and shape of inlet port 266; (c) the size and shape of the inlet switch seat 256 and its top surface 270; (d) the size, shape and number of the outlet cavity 158 and the outlet ports 260; (e) the height of the switch gap 268, when the driving pressure difference (P) across the flow switch 250 is zero; and (f) the driving pressure difference (P) across the flow switch 250.

MICROMACHINED MEMBRANE FLOW SWITCH 250 (FIGS. 33–38): MANUFACTURE

The manufacture of the flow switch 250 is similar to the manufacture of the one-way valve 300 of FIGS. 30–31, except for those differences which will be made apparent by an examination of all of the Figures and all of the disclosures in this document.

For example, the desired initial switch gap 268 (at a zero driving pressure difference (P) across the flexure 264), may be obtained by using an etching process in which the inlet switch seat 256 is etched by an amount equal to the desired initial switch gap 268, while the substrate 252's top surface 278 is not etched at all.

MICROMACHINED RADIAL ARRAY FILTER 340 (FIGS. 39–40): STRUCTURE

Figure 39:
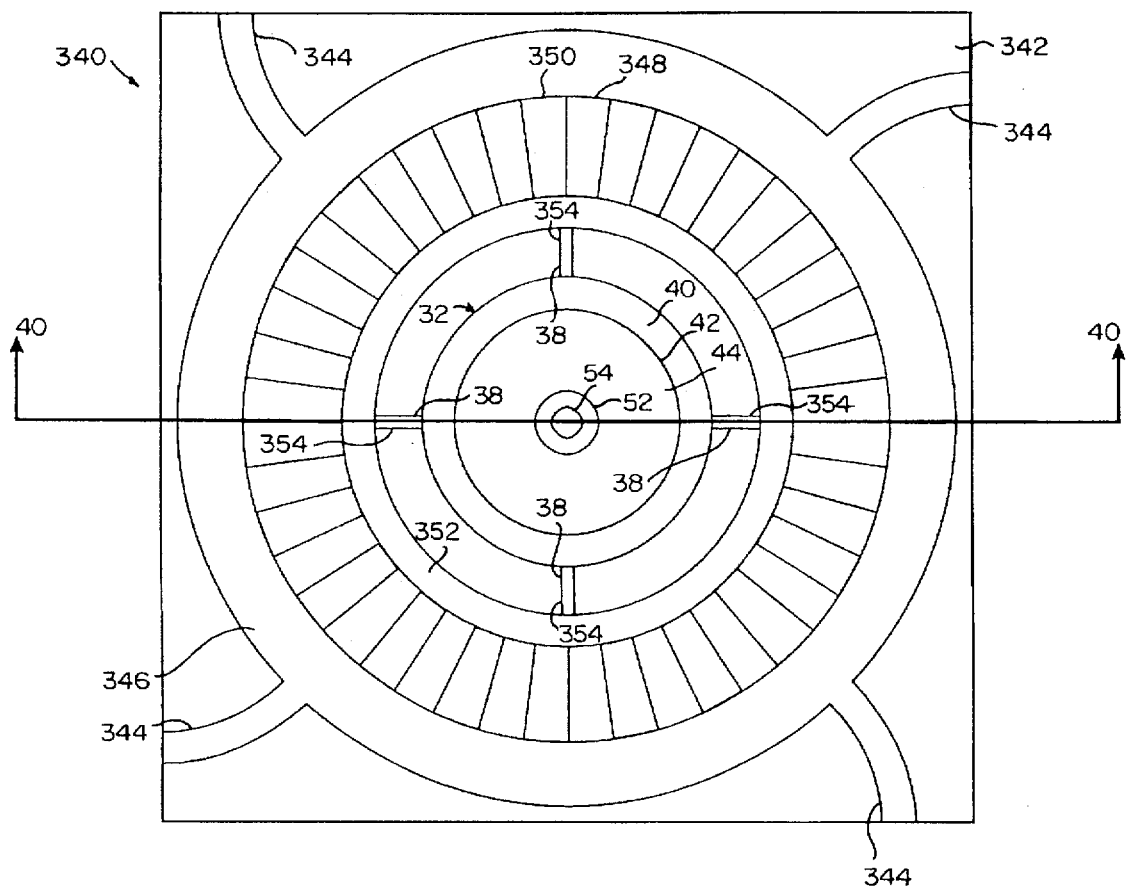
FIG. 39 is a top elevational view of the substrate of the micromachined radial array filter of the present invention.
Figure 40:
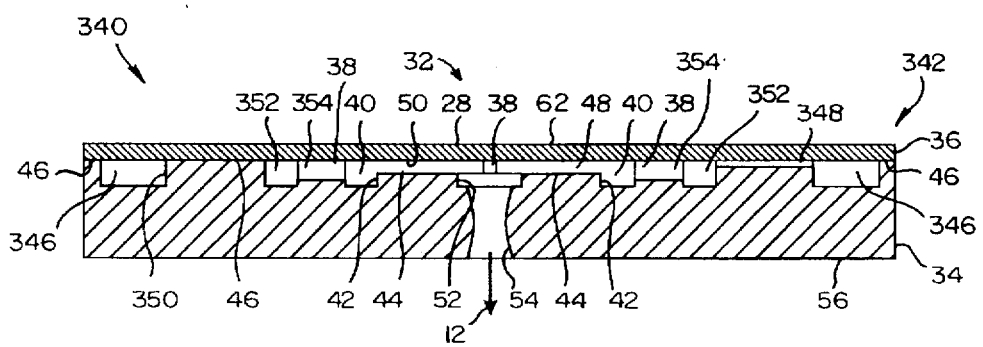
FIG. 40 is a cross-sectional view thereof, taken substantially along line 40—40 of FIG. 39.

The micromachined radial array filter 340 of the present invention is illustrated in FIGS. 39–40 as having been manufactured with a radial flow regulator 32 on the same chip 342. The chip 342 may be disposable, in that it may discarded and replaced by a new chip 342 if the filter 340 becomes clogged with filtered particles from the medication 12, or if the regulator 32 does not function properly.

Although the filter 340 and the regulator 32 are illustrated as having a geometric relationship in which the regulator 32 is nested inside of the filter 340, for an unusually compact and space-saving configuration; the filter 340 and the regulator 32 may have any other suitable geometric relationship with respect to each other on the chip 342; and the filter 340 and the regulator 32 may be located on separate chips. Although the filter 340 is described as being used in conjunction with a regulator 32, it may be used in conjunction with any other device, to supply filtered medication 12 to that device.

For clarity, the corresponding parts of the regulator 32 of FIGS. 39–40 have been given the same reference numerals as the regulator 32 of FIGS. 1–2, since the regulator 32 of FIGS. 39–40 has the same structure, operation, theory and manufacture as the regulator 32 of FIGS. 1–2, except for those differences which will be made apparent by an examination of all of the Figures and all of the disclosures in this document.

The filter 340 may comprise a substrate 34 and a membrane 36 which is secured to the substrate 34's top surface 46. The substrate 34 may have four inlet ports 344; an inlet cavity 346; a radial array of twenty-two filter slots 348, which alternate with twenty-two ribs 350; an outlet cavity 352; and four outlet ports 354. The membrane 36 may form the top surface of the inlet ports 344, the inlet cavity 346, the filter slots 348, the outlet cavity 352, and the outlet ports 354.

Although four equally spaced inlet ports 344 are illustrated, each having a rectangular cross-sectional configuration and following an arcuate path, there may be fewer or more inlet ports 344, the inlet ports 344 may not be equally spaced, each inlet port 344 may have any other suitable size and shape, and each inlet port 344 may follow any other suitable path, whether or not that path is straight. The functions of each inlet port 344 may include transporting the medication 12 from a source of medication 12 to at least one inlet cavity 346.

Although only a single inlet cavity 346 is illustrated, having a rectangular cross-sectional configuration, and following a ring-shaped path, there may be more than one inlet cavity 346, each communicating with at least one inlet port 344 and at least one filter slot 348, each inlet cavity 346 may have any other suitable size and shape, and each inlet cavity 346 may follow any other suitable path, whether or not that path is straight. The functions of each inlet cavity 346 may include transporting the medication 12 from at least one inlet port 344 to at least one filter slot 348.

Although the inlet ports 344 and the inlet cavity 346 are illustrated as being discrete elements of the filter 340, they may be merged partially or wholly together, such as by enlarging the inlet ports 344 until they perform some or all of the functions of the inlet cavity 346, or by enlarging the inlet cavity 346 until it performs some or all of the functions of the inlet ports 344.

Although a radial array of twenty-two identical filter slots 348 is illustrated, each filter slot 348 having a generally rectangular cross-sectional configuration, and a generally trapezoidal shape, the filter slots 348 may be arranged in any other suitable way or array with respect to each other, there may be fewer or more filter slots 348, each filter slot 348 may have any other suitable size, cross-sectional configuration, and shape, and all of the filter slots 348 need not be identical. The functions of the filter slots 348 may include removing undesired particles from the incoming medication 12; and guiding the medication 12 to the outlet cavity 352.

Although a radial array of twenty-two ribs 350 is illustrated, each having a generally rectangular cross-sectional configuration and a generally trapezoidal shape, the ribs 350 may be arranged in any other suitable way or array with respect to each other, there may be fewer or more ribs 350, and each rib 350 may have any other suitable size, cross-sectional configuration, and shape. The functions of the ribs 350 may include helping to define the filter slots 348; and supporting the membrane 36.

Although a only a single outlet cavity 352 is illustrated, having a square cross-sectional configuration, and following a ring-shaped path, there may be more than one outlet cavity 352, each communicating with at least one filter slot 348 and at least one outlet port 354, each outlet cavity 352 may have any other suitable size and shape, and each outlet cavity 352 may follow any other suitable path, whether or not that path is straight. The functions of each outlet cavity 352 may include transporting the medication 12 from at least one filter slot 348 to at least one outlet port 354.

Although four equally spaced outlet ports 354 are illustrated, each having a rectangular cross-sectional configuration, and following a straight path, there may be fewer or more outlet ports 354, the outlet ports 354 may not be equally spaced, each outlet port 354 may have any other suitable size and shape, and each outlet port 354 may follow any other suitable path, whether or not that path is straight. The functions of each outlet port 354 may include transporting the medication 12 away from at least one outlet cavity 352, and delivering the medication 12 to whatever person, animal or thing may be receiving the medication 12 from the outlet port 354.

Although the outlet ports 354 and the outlet cavity 352 are illustrated as being discrete elements of the filter 340, they may be merged partially or wholly together, such as by enlarging the outlet ports 354 until they perform some or all of the functions of the outlet cavity 352, or by enlarging the outlet cavity 352 until it performs some or all of the functions of the outlet ports 354.

Although the outlet ports 354 are illustrated as forming the regulator 32's inlet ports 38, the outlet ports 354 and the inlet ports 38 may be discrete elements which may be fluidly connected in any suitable way by any suitable means.

By way of example, the filter 340 may have the following physical parameters. The substrate 34 may be manufactured from 7740 Pyrex glass, may be a square having sides with a length of about 0.635 cm, and may have a maximum thickness of about 0.5 mm. Each inlet port 344 may have a width of about 0.5 mm, a depth of about 10 microns, and a length of about 250 microns. The inlet cavity 346 may have a width of about 0.0127 cm, a depth of about 10 microns, and an internal diameter of about 0.58 cm. There may be 22 filter slots 348 and 22 ribs 350, and the sides of each filter slot 348 and each rib 350 may lay on a respective radial ray emanating from the center of the filter 340. Each filter slot 348 may be about 0.10 to about 5.0 microns high. Each filter slot 348 and each rib 350 may lie between an inner circle having a diameter of about 0.33 cm, and an outer circle having a diameter of about 0.58 cm. The outlet cavity 352 may have a width of about 0.0254 cm, a depth of about 10 microns, and an outer diameter of 0.33 cm. Each outlet port 354 may have a depth of about 10 microns, a width of about 250 microns, and a length of about 250 microns. The membrane 36 may be manufactured from silicon and may have a thickness of about 25 microns.

MICROMACHINED RADIAL ARRAY FILTER 340 (FIGS. 39–40): OPERATION AND THEORY

The chip 342, with its filter 340 and regulator 32, may be installed in its desired location of intended use in any suitable way. Any suitable medication supply means may be used to connect the filter 340's inlet ports 344 to a source of the medication 12; and any suitable medication delivery means may be used to connect the regulator 32's outlet port 54 to whatever person, animal or thing is to receive the medication 12 from the outlet port 54. The medication supply means may also be used to supply the medication 12 to the flexure 28's top surface 62, at a pressure which may or may not be the same as the pressure at which the medication 12 is supplied to the inlet ports 344.

For example, the chip 342 may be installed within any type of reservoir means for the medication 12 by any suitable means, such as by locating the regulator 32's outlet port 54 over the reservoir means's outlet, and by using an adhesive face seal between the substrate 34's bottom surface 56 and the inside of the reservoir means to hold the chip 342 in place. As a result, when the reservoir means is filled with the medication 12, the chip 342 will be immersed in the medication 12, with the filter 340's inlet ports 344 and the flexure 28's top surface 62 in fluid communication with the medication 12 within the reservoir means, and with the regulator 32's outlet port 54 in fluid communication with the reservoir means' outlet. Such an installation for the chip 342 has numerous advantages.

For example, it is quick, easy, reliable and inexpensive, because no additional medication supply means (such as supply conduits) are needed to supply the medication 12 to the filter 340's inlet ports 344 and to the flexure 28's top surface 62 (since they are already immersed in the medication 12); and because no additional medication delivery means (such as delivery conduits) are needed to convey the medication 12 away from the regulator 32's outlet port 54 (since the reservoir means' outlet is used for this purpose). Such additional inlet and outlet conduits may be undesirable since it may be relatively time consuming, difficult and expensive to align and connect them to the chip 342, due to the extremely small size of the filter 340's inlet ports 344, the flexure 28, and the regulator 32's outlet port 54. Such additional inlet conduits may also be undesirable because they may tend to trap a bubble when being filled with a liquid medication 12, which bubble might then be carried into the filter 340 and the regulator 32 and cause them to malfunction.

Alternatively, if the chip 342 did not have a regulator 32, but had only a filter 340, then such a chip 342 may be installed in its intended location of use in any suitable way. Any suitable medication supply means may be used to connect the filter 340's inlet ports 344 to a source of the medication 12; and any suitable medication delivery means may be used to connect the filter 340's outlet ports 354 to whatever person, animal or thing is to receive the medication 12 from the outlet ports 354.

The driving pressure difference (P) across the filter 340 may be defined as the driving pressure difference (P) between the flexure 28's top surface 62 and the outlet port 54. During operation, as a driving pressure difference (P) is applied across the filter 340 in any suitable way, such as by pressurizing the source of medication 12 with respect to the outlet port 54, the medication 12 will flow sequentially through the filter 340's inlet ports 344, inlet cavity 346, filter slots 348, outlet cavity 352, and outlet ports 354. From the filter 340's outlet ports 354, the medication 12 will then flow sequentially through the regulator 32 from its inlet ports 38 to its outlet port 54 in the manner which has been described previously regarding the regulator 32 of FIGS. 1–2.

The size of the filter 340's filter slots 348 is selected to be such that the filter slots 348 will be able trap the smallest particle which the filter 340 is designed to remove from the medication 12. The size of the filter slots 348 may depend on the size of the smallest particle which can be tolerated by the person, animal or thing which is to receive the filtered medication 12 from the filter 340. For example, if the filter 340 is intended to deliver the medication 12 to a regulator 32, as illustrated in FIGS. 39–40, then preferably the filter 340's filter slots 348 may be chosen to have a size which is at least slightly smaller than the size of the smallest fluid path dimension in the regulator 32, namely its regulator gap 48. In this way, the filter slots 348 will be able to trap all of the particles in the medication 12 which might otherwise clog the smallest fluid path dimension in the regulator 32.

It should be noted that the micromachining process for manufacturing the filter slots 348 in the substrate 34 may easily manufacture filter slots 348 which have a depth of from about 0.10 microns, or less, to about 10.00 microns, or greater.

Any pressure exerted by the medication 12 on the membrane 36's top surface 62 may be prevented from reducing the desired height or cross-sectional configuration of the inlet ports 344, the inlet cavity 346, the filter slots 348, the outlet cavity 352 and the outlet ports 354 in any suitable way, such as by selectively adjusting one or more of the pertinent parameters, such as: (a) the stiffness, elasticity, resiliency, thickness, size, shape and cross-sectional configuration of the membrane 36; and (b) the length, width, size and shape of the inlet ports 344, the inlet cavity 346, the filter slots 348, the outlet cavity 352 and the outlet ports 354.

For the longest, most effective life of the filter 340, it may be preferred that all of the filter slots 348 be utilized an approximately equal amount. This goal may be at least partially achieved in any suitable way, such as by selectively adjusting one or more of the pertinent parameters, such as: (a) selecting the cross-sectional area of the filter 340's inlet cavity 346 to be large enough so that the pressure drop of the medication 12 in the inlet cavity 346 between the adjacent inlet ports 344 may be reduced, or minimized, to the point that the flow of the medication 12 from the inlet ports 344 is distributed at least approximately equally by the inlet cavity 346 to each of the filter slots 348; (b) selecting the cross-sectional area of the filter 340's outlet cavity 352 to be large enough so that the pressure drop of the medication 12 in the outlet cavity 346 between adjacent outlet ports 354 may be reduced, or minimized, to the point that the outgoing flow of medication 12 is distributed at least approximately equally by the outlet cavity 352 to each of the outlet ports 354; and (c) selecting the cross-sectional areas of the filter 340's inlet cavity 346 and outlet cavity 352 so that the pressure drop of the medication 12 across each of the filter slots 348 may be at least approximately equal.

The fluid resistance of the filter 340 to the medication 12 may be selectively adjusted in any suitable way, such as by selectively adjusting at least one of the pertinent parameters, such as the number, length, size, shape and path followed by the inlet ports 344, the inlet cavity 246, the outlet cavity 352, the outlet ports 354, and the filter slots 348.

The filter 340 may be designed to have a small, or negligible, fluid flow resistance to the medication 12 when new, in order to provide a margin for an accumulation of filtered particles in the filter slots 348. That is, the filter 340 may be designed so that after a predetermined quantity of particles have been trapped by the filter slots 348, a predetermined minimum fluid flow rate (Q) of the medication 12, at a predetermined driving pressure difference (P) across the filter 340, will still be permitted to flow through the filter 340. If this is done, and if the filter 340 is used in conjunction with a regulator 32, such as is seen in FIGS. 39–40, then any fluid flow resistance of the medication 12 within the regulator 32 which is needed for proper pressure bias of the flexure 28 may be provided by the regulator 32's inlet ports 38 and inlet cavity 40.

Alternatively, the fluid flow resistance of the filter 340 may be selected to have a significant fluid flow resistance to the medication 12 when new, in order to provide for proper pressure bias of the regulator 32's flexure 28. In other words, such a filter 340 may provide the dual functions of: (a) filtering out undesired particles from the medication 12; and (b) defining the flow rate operating point of the regulator 32, i.e., defining the maximum flow rate (Q) of the medication 12 through the regulator 32. In this case, the flow rate (Q) of the medication 12 through the filter 340 may fall as its filter slots 348 become clogged with filtered particles during use, and it may be prudent to provide some level of medication pre-filtering.

In general, it may be advantageous to provide the filter 340 with medication 12 which has been pre-filtered to a substantial degree to remove undesired particles from the medication 12 which are larger than the smallest particles which the filter 340 is intended to trap. By such pre-filtering of large particles from the medication 12, the useful life of the filter 340 may be greatly extended, since the filter 340 is a precision filter for filtering very small particles, and thus it may take only a relatively small number of large particles to clog it.

MICROMACHINED RADIAL ARRAY FILTER 340 (FIGS. 39–40): MANUFACTURE

The substrate 34 may be manufactured from any suitable strong, durable material which is compatible with the medication 12; in which the filter 340's inlet ports 346, inlet cavity 346, filter slots 358, outlet cavity 352 and outlet ports 354 may be manufactured in any suitable way; and in which the regulator 32's inlet channels 38, inlet cavity 40, regulator seat 42, outlet cavity 52, and outlet port 54 may be manufactured in any suitable way. Suitable ways may include using any suitable etching, molding, stamping and machining process. Such a machining process may include the use of physical tools, such as a drill; the use of electromagnetic energy, such as a laser; and the use of a water jet.

The membrane 36 may be manufactured from any suitable strong, durable, flexible, material which is compatible with the medication 12.

If the filter 340 and the regulator 32 are intended to regulate a medication 12 which is to be supplied to a human or an animal, then any part of the filter 340 and the regulator 32 which is exposed to the medication 12 should be manufactured from, and assembled or bonded with, non-toxic materials. Alternatively, any toxic material which is used to manufacture the filter 340 and the regulator 32, and which is exposed to the medication 12 during use of the filter 340 and the regulator 32, may be provided with any suitable non-toxic coating which is compatible with the medication 12.

Suitable materials for the substrate 34 and the membrane 36 may be metals (such as titanium), glasses, ceramics, plastics, polymers (such as polyimides), elements (such as silicon), various chemical compounds (such as sapphire, and mica), and various composite materials.

The substrate 34 and the membrane 36 may be assembled together in any suitable leak-proof way. Alternatively, the substrate 34 and the membrane 36 may be bonded together in any suitable leak-proof way, such as by anodically bonding them together; such as by fusing them together (as by the use of heat or ultrasonic welding); and such as by using any suitable bonding materials, such as adhesive, glue, epoxy, solvents, glass solder, and metal solder.

Anodically bonding the substrate 34 and the membrane 36 together may be preferable for at least four reasons; which reasons were discussed previously regarding the regulator 32 of FIGS. 1–2.

One example of how the chip 342, with its filter 340 and regulator 32, may be manufactured will now be given. The starting point may be a 76.2 mm diameter wafer of Corning 7740 Pyrex glass, which will form the substrate 34.

The filter 340's inlet ports 344, inlet cavity 346, filter slots 348, outlet cavity 352, and outlet ports 354; and the FIGS. 39–40 regulator 32's inlet channels 38, inlet cavity 40, regulator seat 42 and outlet cavity 52 may be manufactured in the substrate 34 in any suitable way. One suitable way may be to use an etching process which is the same as, or at least similar to, that used to manufacture the FIGS. 1–2 regulator 32's inlet channels 38, inlet cavity 40, regulator seat 42 and outlet cavity 52, except for those differences, if any, which will be made apparent by an examination of all of the Figures and disclosures in this document.

The FIGS. 39–40 outlet port 54 may then be manufactured in the substrate 34 in any suitable way. One suitable way may be use a laser drilling process which is the same as, or at least similar to, that used to manufacture the FIGS. 1–2 regulator 32's outlet port 54, except for those differences, if any, which will be made apparent by an examination of all of the Figures and disclosures in this document.

A layer of corrosion-resistant material(s) may then be applied to all of the surfaces of the filter 340's inlet ports 344, inlet cavity 346, filter slots 348, outlet cavity 352 and outlet ports 354; and to all of the surfaces of the FIGS. 39–40 regulator 32's inlet channels 38, inlet cavity 40, regulator seat 42, outlet cavity 52, and outlet port 54 in any suitable way. One suitable way may be to use an application process which is the same as, or at least similar to, that used to apply a layer of corrosion-resistant material(s) to the FIGS. 1–2 regulator 32's inlet channels 38, inlet cavity 40, regulator seat 42, outlet cavity 52, and outlet port 54, except for those differences, if any, which will be made apparent by an examination of all of the Figures and disclosures in this document.

The FIGS. 39–40 membrane 36 may be manufactured from a silicon wafer, and secured to the glass wafer (which is the FIGS. 39–40 substrate 34), in any suitable way. One suitable way may be to use a manufacturing and securing process which is the same as, or at least similar to, that used to manufacture the FIGS. 1–2 membrane 36, and to secure it to the FIGS. 1–2 substrate 34, except for those differences, if any, which will be made apparent by an examination of all of the Figures and disclosures in this document.

As was mentioned above, although the filter 340 is illustrated in FIGS. 39–40 as being manufactured on the chip 342 with a regulator 32, the filter 340 may be manufactured by itself on the chip 342, without a regulator 32.

In such a case, all or part of the filter 340's outlet ports 354 may extend from the outlet cavity 352 down through the substrate 34 (in a fashion similar to the regulator 32's outlet port 54). Such downwardly extending outlet ports 354 for the filter 340 may have any suitable shape, such as a venturi shape; and may be manufactured in any suitable way. One suitable way may be use a laser drilling process which is the same as, or at least similar to, that used to manufacture the FIGS. 1–2 regulator 32's outlet port 54, except for those differences, if any, which will be made apparent by an examination of all of the Figures and disclosures in this document.

The manufacture of only one filter 340, and the manufacture of only one filter 340/regulator 32 combination were described above. However, it will be appreciated that on any pair of glass and silicon wafers the substrates 34 and the membranes 36 for a large number of filters 340, or filter 340/regulator 32 combinations could be manufactured simultaneously in a manner similar to that described above. If such is the case, an array of substrates 34 may be simultaneously etched in the glass wafer; their outlet ports 54 may be drilled, and the layer of one or more corrosion-resistant substances may be applied to the substrates 34. Then the silicon and glass wafers for the substrates 34 and the membranes 36 may be aligned and secured together. Then, all of the membranes 36 may be manufactured simultaneously by grinding and etching the silicon wafer to its desired final thickness. The silicon/glass substrate 34/membrane 36 sandwich may then be divided by any suitable means (such as dicing) into individual chips, each chip bearing at least one filter 340 or filter 340/regulator 32 combination.

One of the advantages of using etching and anodic bonding processes to manufacture the filter 340, and the filter 340/regulator 32 combination, is that such processes enable high quality, very reliable filters 340, and filter 340/regulator 32 combinations, to be mass produced in great numbers at a cost so low that the filters 340 and the filter 340/regulator 32 combinations may be considered to be disposable.

Further, it should also be noted that the filter 340 and the filter 340/regulator 32 combination are stunning in their simplicity since they both have only two basic parts, i.e. their substrates 34 and their membranes 36; and since the regulator 32 has only one moving part, i.e., its flexure 28, which merely bows during operation of the filter 340/regulator 32 combination. In addition, because the raw materials from which the filter 340 and the filter 340/regulator 32 combination may be manufactured may be very inexpensive, such as glass and silicon, the cost of the filter 340 and the filter 340/regulator 32 combination may held to a very low level.

MICROMACHINED SLAB FILTER 380 (FIGS. 41–43): STRUCTURE

Figure 41:
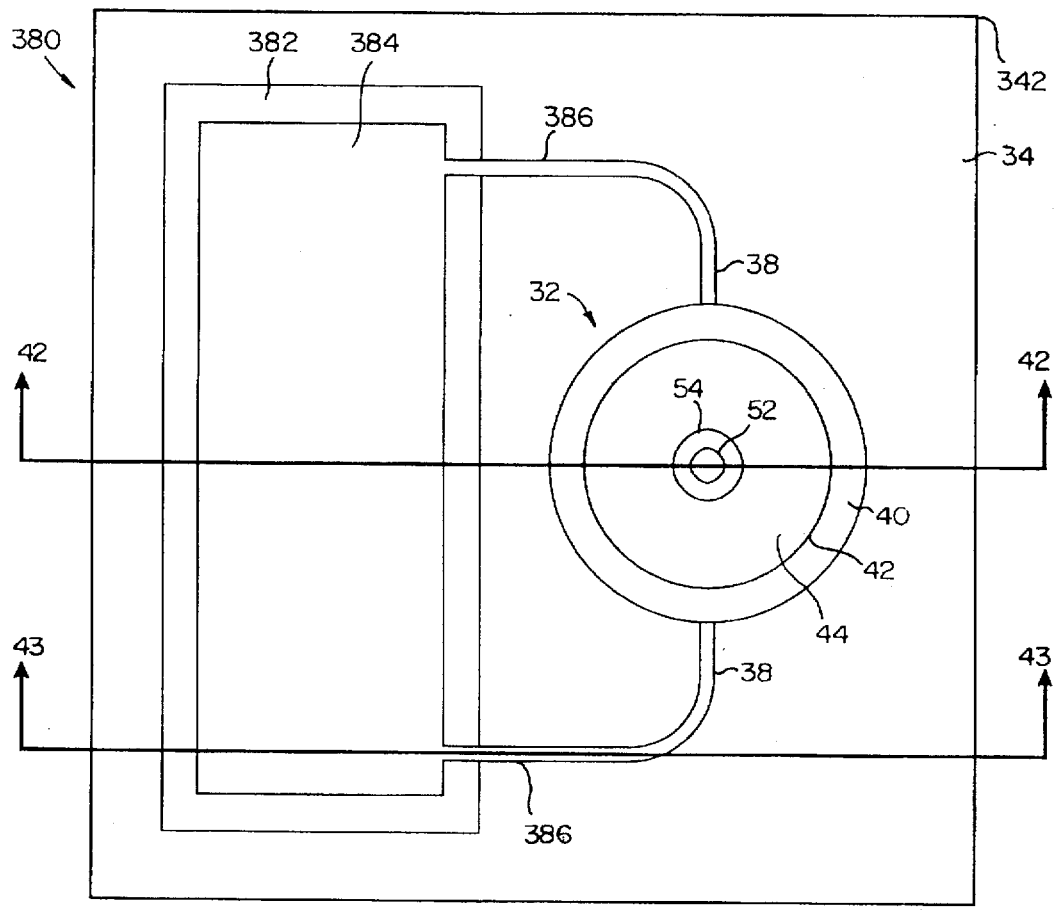
FIG. 41 is a top elevational view of the substrate of a first embodiment of the micromachined slab filter of the present invention.
Figure 42:
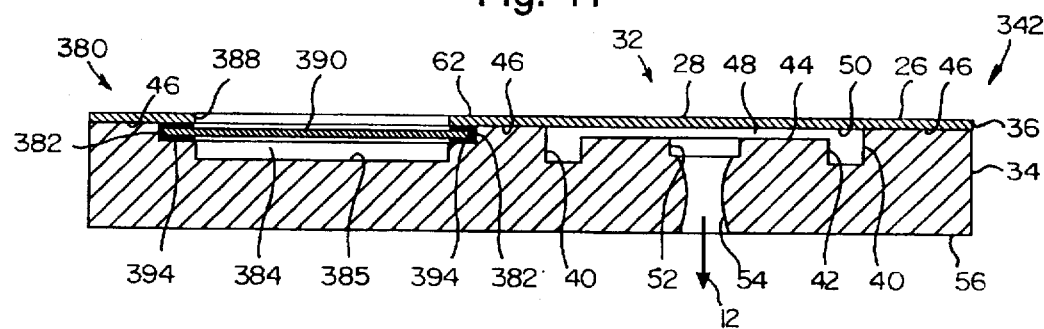
FIG. 42 is a cross-sectional view thereof, taken substantially along line 42—42 of FIG. 41.
Figure 43:
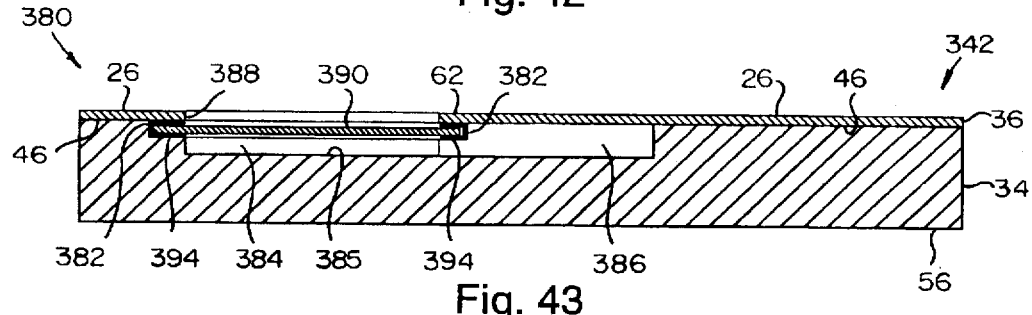
FIG. 43 is a cross-sectional view thereof, taken substantially along line 43—43 of FIG. 41.

The micromachined slab filter 380 of the present invention is illustrated in FIGS. 41–43 as having been manufactured with a radial flow regulator 32 on the same chip 342. The chip 342 may be disposable, in that it may discarded and replaced by a new chip 342 if the filter 380 becomes clogged with filtered particles from the medication 12, or if the regulator 32 does not function properly.

Although the filter 380 and the regulator 32 are illustrated as having a geometric relationship in which the filter 380 is along side of the regulator 32, the filter 380 and the regulator 32 may have any other suitable geometric relationship with respect to each other on the chip 342. For example, the filter 380 may be ring-shaped and sized so that the regulator 32 may be nested inside of the ring-shaped filter 380 (similar to the arrangement of the radial array filter 340 and the regulator 32 of FIGS. 39–40).

Although the filer 380 and the regulator 32 are illustrated as being on the same chip 342, the filter 380 and the regulator 32 may be located on separate chips.

Although the filter 380 is described as being used in conjunction with a regulator 32, it may be used in conjunction with any other device, to supply filtered medication 12 to that device.

For clarity, the corresponding parts of the regulator 32 of FIGS. 41–43 have been given the same reference numerals as the regulator 32 of FIGS. 1–2, since the regulator 32 of FIGS. 41–43 has the same structure, operation, theory and manufacture as the regulator 32 of FIGS. 1–2, except for those differences which will be made apparent by an examination of all of the Figures and all of the disclosures in this document.

The filter 380 may comprise a substrate 34; a filter element 390; and a membrane 36, which is secured to the substrate 34's top surface 46.

The membrane 36 may have an inlet port 388.

The substrate 34 may have a recessed filter mounting lip 382, for receiving the filter element 390's edges; an outlet cavity 384, which is at least partially surrounded by the recessed filter mounting lip 382; and a pair of outlet ports 386.

Although only one, rectangular inlet port 388, filter mounting lip 382, filter element 390, and outlet cavity 384 are illustrated, there may be more than one of any of these elements, and any of these elements may have any other suitable size and shape. And although only two, straight outlet ports 386 are illustrated, each having a rectangular cross-sectional configuration, there may be fewer or more outlet ports 386, each outlet port 386 may have any other suitable size and shape, and each outlet port 386 may follow any suitable path, whether or not that path is straight. For example, there may be an array of filter mounting lips 383, filter elements 390, and outlet cavities 384; each communicating, directly or indirectly, with at least one inlet port 388 and at least one outlet port 386.

The filter element 390's edges may be held in place by being sandwiched between the filter mounting lip 382 and the membrane 36. In such a case, the depth of the filter mounting lip 382 may be selected to be about the same as the thickness of the filter element 390's edges.

An adhesive 394, which is compatible with the medication 12, may be used to help hold the filter element 390's edges in place between the filter mounting lip 382 and the membrane 36; and to provide a seal between the filter mounting lip 382, the filter element 390's edges, and the membrane 36. In such a case, the depth of the filter mounting lip 382 may be selected to be greater than the thickness of the filter element 390's edges, in order to provide room for the adhesive 394.

The seal between the filter mounting lip 382, the filter element 390's edges, and the membrane 36 may help to prevent any leakage of the unfiltered medication 12 around the filter element 390's edges, and into the outlet cavity 384. However, such a seal may not be needed if the tolerances of the filter 380 are such that the largest gap between the filter mounting lip 382, the filter element 390's edges, and the membrane 36 is smaller than the smallest particle in the medication 12 which the filter 380 is designed to filter out of the medication 12.

Alternatively, the filter mounting lip 382 may be eliminated and the filter element 390's edges may be mounted either on top of, or under, the membrane 36 by any suitable means, such as by using any suitable adhesive or bonding process.

The outlet cavity 384 may be provided with at least one filter element support (not illustrated, for clarity). The functions of each filter element support may include helping to prevent those portions of the filter element 390 which lie over the outlet cavity 384 from collapsing down into the outlet cavity 384, while simultaneously not unduly interfering with the flow of the medication 12 through the outlet cavity 384 to the outlet ports 386. Each filter element support may have any suitable size and shape, such as like the pump 130's radial spine type membrane supports 148 (see FIGS. 16–17), or the pump 180's cylindrical pin type membrane supports 148 (see FIGS. 18–19).

By way of example, the filter 380 may have the following physical parameters. The substrate 34 may be manufactured from 7740 Pyrex glass, may be a square having sides with a length of about 0.635 cm, and may have a maximum thickness of about 1.0 mm. The filter mounting lip 382 may have a length of about 4.6 mm; a width of about 1.8 mm; and a depth of about 65 microns, as measured from the substrate 34's top surface 46. The outlet cavity may have a length of about 4.0 mm; a width of about 1.5 mm; and a depth of about 25 microns, as measured from the substrate 34's top surface 46. The outlet ports 386 may have a length of about 3.0 mm; a width of about 250 microns; and a depth of about 25 microns, as measured from the substrate 34's top surface 46. The filter element 390 may be made from Anopore inorganic membrane having a maximum pore size of about 0.1 microns, (the Anopore inorganic membrane is described in more detail below). The filter element 390 may have a filter area about 1.5 mm wide and about 4.0 mm long. The membrane 36 may be made from silicon, and may have a thickness of about 25 microns.

When the medication 12 is distilled water, the example filter 380, having the physical parameters set forth, may have a flow rate of about 1.0 cc/day, with a pressure drop across the filter element 290 of about 5.15 mm Hg.

MICROMACHINED SLAB FILTER 380 (FIGS. 41–43): OPERATION AND THEORY

The chip 342, with its filter 380 and regulator 32, may be installed in its desired location of intended use in any suitable way. Any suitable medication supply means may be used to connect the filter 380's inlet port 388 to a source of the medication 12; and any suitable medication delivery means may be used to connect the regulator 32's outlet port 54 to whatever person, animal or thing is to receive the medication 12 from the outlet port 54. The medication supply means may also be used to supply the medication 12 to the flexure 28's top surface 62, at a pressure which may or may not be the same as the pressure at which the medication 12 is supplied to the inlet port 388.

For example, the chip 342 may be installed within any type of reservoir means for the medication 12 by any suitable means, such as by locating the regulator 32's outlet port 54 over the reservoir means's outlet, and by using an adhesive face seal between the substrate 34's bottom surface 56 and the inside of the reservoir means to hold the chip 342 in place. As a result, when the reservoir means is filled with the medication 12, the chip 342 will be immersed in the medication 12, with the filter 380's inlet port 388 and the flexure 28's top surface 62 in fluid communication with the medication 12 within the reservoir means, and with the regulator 32's outlet port 54 in fluid communication with the reservoir means' outlet. Such an installation for the chip 342 has numerous advantages.

For example, it is quick, easy, reliable and inexpensive, because no additional medication supply means (such as supply conduits) are needed to supply the medication 12 to the filter 380's inlet port 388 and to the flexure 28's top surface 62 (since they are already immersed in the medication 12); and because no additional medication delivery means (such as delivery conduits) are needed to convey the medication 12 away from the regulator 32's outlet port 54 (since the reservoir means' outlet is used for this purpose). Such additional inlet and outlet conduits may be undesirable since it may be relatively time consuming, difficult and expensive to align and connect them to the chip 342, due to the extremely small size of the filter 380's inlet port 388, the flexure 28, and the regulator 32's outlet port 54. Such additional inlet conduits may also be undesirable because they may tend to trap a bubble when being filled with a liquid medication 12, which bubble might then be carried into the filter 380 and the regulator 32 and cause them to malfunction.

Alternatively, if the chip 342 did not have a regulator 32, but had only a filter 380, then such a chip 342 may be installed in its intended location of use in any suitable way. Any suitable medication supply means may be used to connect the filter 380's inlet port 388 to a source of the medication 12; and any suitable medication delivery means may be used to connect the filter 380's outlet ports 386 to whatever person, animal or thing is to receive the medication 12 from the outlet ports 386.

The driving pressure difference (P) across the filter 380 may be defined as the driving pressure difference (P) between the flexure 28's top surface 62 and the outlet port 54. During operation, as a driving pressure difference (P) is applied across the filter 380 in any suitable way, such as by pressurizing the source of medication 12 with respect to the outlet port 54, the medication 12 will flow sequentially through the filter 380's inlet port 388, filter element 390, outlet cavity 384, and outlet ports 386. From the filter 380's outlet ports 386, the medication will then flow sequentially through the radial flow regulator 32 from its inlet ports 38 to its outlet port 54 in the manner which has been described previously regarding the radial flow regulator 32 of FIGS. 1–2.

The pore size of the filter element 390 is selected to be such that the filter element 390 will be able trap the smallest particle which the filter 380 is designed to remove from the medication 12. The pore size of the filter element 390 may depend on the size of the smallest particle which can be tolerated by the person, animal or thing which is to receive the filtered medication 12 from the filter 380. For example, if the filter 380 is intended to deliver the medication 12 to a regulator 32, as illustrated in FIGS. 41–43, then preferably the pore size of the filter element 390 may be chosen to have a size which is at least slightly smaller than the size of the smallest fluid path dimension in the regulator 32, namely its regulator gap 48. In this way, the filter element 390 will be able to trap all of the particles in the medication 12 which might otherwise clog the smallest fluid path dimension in the regulator 32.

The flow rate (Q) of the medication 12 through the filter element 390 may selected in any suitable way, such as by selectively adjusting one or more of the pertinent parameters, such as: (a) the driving pressure difference (P) across the filter 390; (b) the filter area of the filter element 390, that is the portion of the filter element 390 which is exposed to the medication 12 during use; and (c) the filter element 390's pore size.

The useful life of the filter 380 is over when so many of the filter element 390's pores have been clogged by particles filtered from the medication 12 that, at the maximum desired driving pressure difference (P) across the filter 380, the minimum desired flow rate (Q) of the medication 12 through the filter 380 can no longer be achieved. Thus, both the flow rate (Q) and the useful life of the filter 380 is a function of how many of the filter element 390's pores have been clogged by particles filtered from the medication 12. For any given pore size of the filter element 390, the useful life of the filter 380 may be selectively increased or decreased, respectively, by selectively increasing or decreasing the filter area of the filter element 390.

In general, it may be advantageous to provide the filter 380 with medication 12 which has been pre-filtered to a substantial degree to remove undesired particles from the medication 12 which are larger than the smallest particles which the filter 380 is intended to trap. By such pre-filtering of large particles from the medication 12, the useful life of the filter 380 may be greatly extended, since the filter 380 is a precision filter for filtering very small particles, and thus it may take only a relatively small number of large particles to clog it.

The driving pressure difference (P) across the filter 380 may tend to cause portions of the filter element 390 to bow towards the outlet cavity 384's bottom surface 385. A problem may arise if any portions of the filter element 390 are forced against the cavity 384's bottom 385, since those portions of the filter element 390 would no longer be able to perform their intended filtering function. This problem may be addressed in any suitable way, such as by selectively adjusting one or more of the pertinent parameters, such as (a) the number, size, shape and location of any filter element supports for the filter element 390 which may be provided in the outlet cavity 384; (b) the size, shape and depth of the outlet cavity 384; and (c) the stiffness, elasticity, resiliency, thickness, cross-sectional configuration, size and shape of the filter element 390.

The fluid resistance of the filter 380 to the medication 12 may be selectively adjusted in any suitable way, such as by selectively adjusting at least one of the pertinent parameters, such as: (a) the number, size, and shape of the inlet port 388; (b) the number, size, shape, thickness and pore size of the filter element 390; (c) the number, size, shape, and depth of the outlet cavity 384; (d) the number, size, shape and location of any filter element supports in the outlet cavity 384 for the filter element 390; and (e) the number, length, size, shape, and path followed by each of the outlet ports 386.

The filter 380 may be designed to have a small, or negligible, fluid flow resistance to the medication 12 when new, in order to provide a margin for an accumulation of filtered particles in the filter element 390's pores. That is, the filter 380 may be designed so that after a predetermined quantity of particles have been trapped in the filter element 390's pores, a predetermined minimum fluid flow rate (Q) of the medication 12, at a predetermined driving pressure difference (P) across the filter 380, will still be permitted to flow through the filter 380. If this is done, and if the filter 380 is used in conjunction with a radial flow regulator 32, such as is seen in FIGS. 41–43, then any fluid flow resistance of the medication 12 within the radial flow regulator 32 which is needed for proper pressure bias of the regulator portion 58 of the regulator 32's membrane 36, may be provided by the regulator 32's inlet ports 38 or inlet cavity 40.

Alternatively, the fluid flow resistance of the filter 380 may be selected to have a significant fluid flow resistance to the medication 12 when new, in order to provide for proper pressure bias of the regulator portion 58 of the regulator 32's membrane 36. In other words, such a filter 380 may provide the dual functions of: (a) filtering out undesired particles from the medication 12; and (b) defining the flow rate operating point of the radial flow regulator 32, that is, defining the maximum flow rate (Q) of the medication 12 through the radial flow regulator 32. In this case, the flow of the medication 12 through the filter 380 may fall as the filter element 390's pores become clogged with filtered particles during use, and it may be prudent to provide some level of the pre-filtering for the medication 12 which was discussed above.

MICROMACHINED SLAB FILTER 380 (FIGS. 41–43): MANUFACTURE

The substrate 34 may be manufactured from any suitable strong, durable material which is compatible with the medication 12; in which the filter 380's mounting lip 382, outlet cavity 384, filter element supports (if any), and outlet ports 386 may be manufactured in any suitable way; and in which the regulator 32's inlet channels 38, inlet cavity 40, regulator seat 42, outlet cavity 52, and outlet port 54 may be manufactured in any suitable way. Suitable ways may include using any suitable etching, molding, stamping and machining process. Such a machining process may include the use of physical tools, such as a drill; the use of electromagnetic energy, such as a laser; and the use of a water jet.

The membrane 36 may be manufactured from any suitable strong, durable, flexible, material which is compatible with the medication 12, and in which the inlet port 388 may be manufactured in any suitable way, such as by using any suitable etching, molding, stamping and machining process. Such a machining process may include the use of physical tools, such as a drill or saw; the use of electromagnetic energy, such as a laser; and the use of a water jet.

The filter element 390 may be manufactured from any suitable strong, durable material which is compatible with the medication 12, which will permit the desired flow rate (Q) of the medication 12, which can withstand the desired driving pressure (P) across the filter 380, which has a pore size smaller than the smallest particle which is desired to be filtered from the medication 12, and which will not generate particles which may contaminate the medication 12. The filter element 390 may be designed to filter out any particular size of particle from the medication 12, depending on the intended use of the filter 380.

If the filter 380 and the regulator 32 are intended to regulate a medication 12 which is to be supplied to a human or an animal, then any part of the filter 380 and the regulator 32 which is exposed to the medication 12 should be manufactured from, and assembled or bonded with, non-toxic materials. Alternatively, any toxic material which is used to manufacture the filter 380 and the regulator 32, and which is exposed to the medication 12 during use of the filter 380 and the regulator 32, may be provided with any suitable non-toxic coating which is compatible with the medication 12.

Suitable materials for the substrate 34 and the membrane 36 may be metals (such as titanium), glasses, ceramics, plastics, polymers (such as polyimides), elements (such as silicon), various chemical compounds (such as sapphire, and mica), and various composite materials.

Suitable materials for the filter element 390 may be any suitable organic material having suitably sized pores in it, such as a thin polymer which has pores generated in it by using nuclear particle bombardment. Such a filter element 390 may be Nuclepore material made by the Nuclepore Corporation of Pleasanton, Calif., which may have a maximum pore size selected to be in the 0.03 to 12.0 micron range.

Alternatively, the filter element 390 may be manufactured from any suitable inorganic material, such as glass, ceramic or metal which has suitably sized pores in it. For example, the filter element 390 may be made from electrolytically etched aluminum. Such a filter element 390 may be Anopore inorganic membrane, made by Whatman, Inc. of Clifton, N.J., which may have a maximum pore size selected to be in the 0.02 to 0.2 micron range.

Alternatively The filter 380's membrane 36 may be manufactured from the same materials which were used to manufacture the membrane 36.

The substrate 34, the membrane 36 and the filter element 390 may be assembled together in any suitable leak-proof way. Alternatively, the substrate 34, the membrane 36, and the filter element 390 may be bonded together in any suitable leak-proof way, such as by anodically bonding them together; such as by fusing them together (as by the use of heat or ultrasonic welding); and such as by using any suitable bonding materials, such as adhesive, glue, epoxy, solvents, glass solder, and metal solder. The substrate 34 and the membrane 36 may not necessarily be assembled or bonded together with each other in the same way in which the substrate 34, the membrane 36 and the filter element 390 are assembled or bonded together with each other.

Anodically bonding the substrate 34, the membrane 36 and the filter element 390 together may be preferable for at least four reasons; which reasons are the same as, or at least similar to the reasons discussed previously regarding anodically bonding together the substrate 34 and the membrane 36 of the regulator 32 of FIGS. 1–2.

One example of how the chip 342, with its filter 380 and regulator 32, may be manufactured will now be given. The starting point may be a 76.2 mm diameter wafer of Corning 7740 Pyrex glass, which will form the substrate 34.

The filter 380's mounting lip 382, outlet cavity 384, filter element supports (if any), and outlet ports 386; and the FIGS. 41–43 regulator 32's inlet channels 38, inlet cavity 40, regulator seat 42 and outlet cavity 52 may be manufactured in the substrate 34 in any suitable way. One suitable way may be to use an etching process which is the same as, or at least similar to, that used to manufacture the FIGS. 1–2 regulator 32's inlet channels 38, inlet cavity 40, regulator seat 42 and outlet cavity 52, except for those differences, if any, which will be made apparent by an examination of all of the Figures and disclosures in this document.

The FIGS. 41–43 outlet port 54 may then be manufactured in the substrate 34 in any suitable way. One suitable way may be use a laser drilling process which is the same as, or at least similar to, that used to manufacture the FIGS. 1–2 regulator 32's outlet port 54, except for those differences, if any, which will be made apparent by an examination of all of the Figures and disclosures in this document.

A layer of corrosion-resistant material(s) may then be applied to all of the surfaces of the filter 340's mounting lip 382, outlet cavity 384, filter element supports (if any), and outlet ports 386; and to all of the surfaces of the FIGS. 41–43 regulator 32's inlet channels 38, inlet cavity 40, regulator seat 42, outlet cavity 52, and outlet port 54 in any suitable way. One suitable way may be to use an application process which is the same as, or at least similar to, that used to apply a layer of corrosion-resistant material(s) to the FIGS. 1–2 regulator 32's inlet channels 38, inlet cavity 40, regulator seat 42, outlet cavity 52, and outlet port 54, except for those differences, if any, which will be made apparent by an examination of all of the Figures and disclosures in this document.

The filter element 390 then be placed on the substrate 34 with its edges being supported by the filter mounting lip 382 and with its central portions being supported by the filter element supports (if any).

The membrane 36, with its inlet port 388, may be manufactured from a silicon wafer, and secured to the glass wafer (which is the substrate 34) in any suitable way. The structure, operation, theory and manufacture of the filter 380's membrane 36, with its inlet port 388, the securing of the membrane 36 to its substrate 34 is the same as, or at least similar to, the manufacturing of the linear flow regulator 80's membrane 84, with its inlet port 88, and the securing of its membrane 84 to its substrate 86, except for those differences, if any, which will be made apparent by an examination of all of the Figures and disclosures in this document.

It may be preferred that the filter element 390 be made from an inorganic membrane, such as the etched aluminum membrane which was described above, if the filter 380's substrate 34 and membrane 36 are bonded together by using a high temperature process, such as the anodic bonding process which was described above regarding the FIGS. 1–2 regulator 32's substrate 34 and membrane 36. That would offer several advantages, such as allowing the filter element 390 to be simultaneously incorporated into the filter 380 during the manufacture of the regulator 32 on the chip 342; allowing the edges of the filter element 390 to be simultaneously anodically bonded to the substrate 34 and membrane 36 (thereby eliminating the need for any other bonding and sealing materials for this purpose); and permitting the high anodic bonding temperature, to simultaneously burn out or volatilize any organic debris which may be located within the filter 380 and regulator 32.

As was mentioned above, although the filter 380 is illustrated in FIGS. 41–43 as being manufactured on the chip 342 with a regulator 32, the filter 380 may be manufactured by itself on the chip 342, without a regulator 32.

In such a case, all or part of the filter 380's outlet ports 386 may extend from the outlet cavity 384 down through the substrate 34 (in a fashion similar to the regulator 32's outlet port 54). Such downwardly extending outlet ports 386 for the filter 380 may have any suitable shape, such as a venturi shape; and may be manufactured in any suitable way. One suitable way may be use a laser drilling process which is the same as, or at least similar to, that used to manufacture the FIGS. 1–2 regulator 32's outlet port 54, except for those differences, if any, which will be made apparent by an examination of all of the Figures and disclosures in this document.

The manufacture of only one filter 380, and the manufacture of only one filter 380/regulator 32 combination were described above. However, it will be appreciated that on any pair of glass and silicon wafers the substrates 34 and the membranes 36 for a large number of filters 380, or filter 380/regulator 32 combinations could be manufactured simultaneously in a manner similar to that described above. If such is the case, an array of substrates 34 may be simultaneously etched in the glass wafer; their outlet ports 54 may be drilled, and the layer of one or more corrosion-resistant substances may be applied to the substrates 34. Then an array of inlet ports 288 may be simultaneously etched in the silicon wafer. Then the silicon and glass wafers for the substrates 34 and the membranes 36 may be aligned and secured together. Then, all of the membranes 36 may be manufactured simultaneously by grinding and etching the silicon wafer to its desired final thickness. The silicon/glass substrate 34/membrane 36 sandwich may then be divided by any suitable means (such as dicing) into individual chips, each chip bearing at least one filter 380 or filter 380/regulator 32 combination.

One of the advantages of using etching and anodic bonding processes to manufacture the filter 380, and the filter 380/regulator 32 combination, is that such processes enable high quality, very reliable filters 380, and filter 380/regulator 32 combinations, to be mass produced in great numbers at a cost so low that the filters 380 and the filter 380/regulator 32 combinations may be considered to be disposable.

Further, it should also be noted that the filter 380 and the filter 380/regulator 32 combination are stunning in their simplicity since they both have only two basic parts, i.e. their substrates 34 and their membranes 36; and since the regulator 32 has only one moving part, i.e., its flexure 28, which merely bows during operation of the filter 380/regulator 32 combination. In addition, because the raw materials from which the filter 380 and the filter 380/regulator 32 combination may be manufactured may be very inexpensive, such as glass and silicon, the cost of the filter 380 and the filter 380/regulator 32 combination may held to a very low level.

MICROMACHINED SLAB FILTER 400 (FIG. 44) : STRUCTURE, OPERATION, THEORY AND MANUFACTURE

Figure 44:
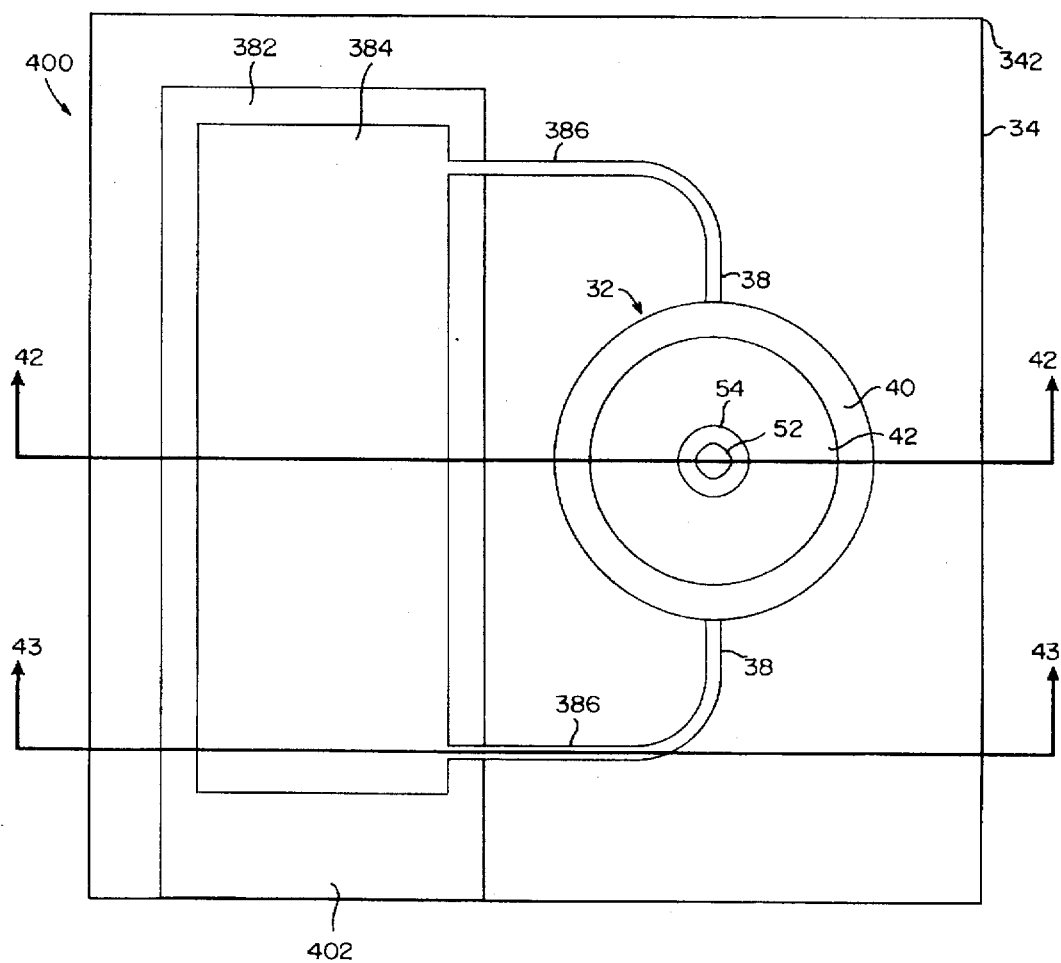
FIG. 44 is a top elevational view of the substrate of a second embodiment of the micromachined slab filter of the present invention.

The micromachined slab filter 400 which is illustrated in FIG. 44 is the same as, or at least similar to, the micromachined slab filter 340 of FIGS. 41–43 in its structure, operation, theory and manufacture, except for those differences which will be made apparent by an examination of all of the Figures and all of the disclosures in this document. Accordingly, the respective parts of the filter 400 of FIG. 44 has been given the same reference numerals as the corresponding parts of the filter 340 of FIGS. 41–43, for clarity and simplicity.

Turning again to FIG. 44, it is seen that the substrate 34 may be provided with a filter element entrance 402, which may extend from the filter mounting lip 382 to the edge of the substrate 34. The filter element entrance 402 and the filter mounting lip 382 may be recessed below the substrate 34's top surface by about the same amount.

As a result, after the slab filter 400's substrate 34 and membrane 36 are bonded together, the filter element entrance 402 and the overlaying portion of the membrane 36 form a slot through which the filter element 390 may be inserted into position on the filter mounting lip 382. After the filter element 390 is in place on the filter mounting lip 382, the filter element may be bonded and sealed in place in any suitable way, such as by using a bonding and sealing process which is the same as, or at least similar to, the bonding and sealing process which was used to bond and seal the FIGS. 41–43 substrate 34, filter element 390 and membrane 36 together, except for those differences which will be made apparent by an examination of all of the Figures and disclosures in this document.

It is understood that the foregoing forms of the invention were described and/or illustrated strictly by way of non-limiting example.

In view of all of the disclosures herein, these and further modifications, adaptations and variations of the present invention will now be apparent to those skilled in the art to which it pertains, within the scope of the following claims.

What is claimed is:

1. A method for manufacturing a fluid flow regulator for maintaining a fluid flow from a source of a fluid within a predetermined fluid flow range, wherein said regulator comprises: a substrate, a membrane, a regulator gap, fluid inlet means for permitting said fluid to enter said regulator and said regulator gap, and fluid outlet means for permitting said fluid to exit from said regulator gap; wherein said substrate comprises a regulator seat and a mounting portion; wherein said membrane comprises a mounting portion and a moveable flow regulating flexure; wherein said regulator gap is located between said moveable flow regulating flexure and said regulator seat; wherein said regulator has an input pressure of said fluid; wherein said moveable flow regulating flexure tends to move closer to said regulator seat as said input pressure increases, to reduce the size of said regulator gap and to maintain said fluid flow within said predetermined fluid flow range despite said increase of said input pressure; wherein said moveable flow regulating flexure tends to move further away from said regulator seat as said input pressure decreases, to increase the size of said regulator gap and to maintain said fluid flow within said predetermined fluid flow range despite said decrease of said input pressure; and wherein said method comprises the steps of:

etching at least a portion of said fluid inlet means, said regulator seat, and said fluid outlet means into said substrate;

locating said moveable flow regulating flexure over said regulator seat; and securing said membrane's mounting portion to said substrate's mounting portion.

2. The method for manufacturing a fluid flow regulator according to claim 1, wherein said securing step comprises anodically bonding said membrane's mounting portion to said substrate.

3. The method for manufacturing a fluid flow regulator according to claim 1, wherein said method further comprises the steps of applying at least one layer of at least one corrosion-resistant material to at least a portion of said regulator; and then securing said layer of at least one corrosion-resistant material to said regulator by using anodic bonding.

4. The method for manufacturing a fluid flow regulator according to claim 3, wherein said steps of securing said membrane to said substrate and of securing said at least one layer of at least one corrosion-resistant material to said regulator occur simultaneously and both of said steps of securing comprise anodic bonding.

5. The method for manufacturing a fluid flow regulator according to claim 1, wherein said micromachining step further comprises the steps of etching said portion of said fluid inlet means into said substrate a first amount; and then simultaneously etching said portion of said fluid inlet means and a regulator seat portion of said substrate an additional, second amount, to simultaneously form said portion of said fluid inlet means and said regulator seat.

6. The method for manufacturing a fluid flow regulator according to claim 1, wherein said method further comprises the step of automatically forming at least a portion of said fluid outlet means into a venturi-like shape by using a laser drill to drill at least a portion of said fluid outlet means into said substrate.

7. The method for manufacturing a fluid flow regulator according to claim 6, wherein said method further comprises the step of heating said substrate to about the anneal point of said substrate before performing said step of using a laser drill, to improve the quality of said fluid outlet means, and to help prevent said substrate from cracking during said step of using a laser drill.

8. The method for manufacturing a fluid flow regulator according to claim 1, wherein said method further comprises forming said membrane by the steps of providing a wafer of material having a first layer which is etchable by an etchant, and having a second layer which is not etchable by said etchant, wherein said second layer has a thickness about equal to the desired final thickness of said membrane, and wherein a mounting portion of said second layer comprises said membrane's mounting portion; securing said second layer's mounting portion to said substrate's mounting portion during said step of securing said membrane's mounting portion to said substrate's mounting portion; and etching away at least a portion of said first layer with said etchant, to leave a remaining portion of said wafer; wherein said membrane then comprises said remaining portion of said wafer.

* * * * *